US009132200B2

(12) United States Patent
Ren et al.

(10) Patent No.: US 9,132,200 B2
(45) Date of Patent: Sep. 15, 2015

(54) OLIGOMER-CALCIUM CHANNEL BLOCKER CONJUGATES

(71) Applicant: NEKTAR THERAPEUTICS, San Francisco, CA (US)

(72) Inventors: Zhongxu Ren, Foster City, CA (US); Bo-Liang Deng, San Ramon, CA (US); Jennifer Riggs-Sauthier, San Francisco, CA (US); Micah Harvey, Madison, AL (US)

(73) Assignee: Nektar Therapeutics, San Francisco, CA (US)

( * ) Notice: Subject to any disclaimer, the term of this patent is extended or adjusted under 35 U.S.C. 154(b) by 0 days.

(21) Appl. No.: 14/266,317

(22) Filed: Apr. 30, 2014

(65) Prior Publication Data

US 2014/0323529 A1  Oct. 30, 2014

Related U.S. Application Data

(63) Continuation of application No. 12/674,139, filed as application No. PCT/US2008/010385 on Sep. 3, 2008, now Pat. No. 8,748,648.

(60) Provisional application No. 60/967,764, filed on Sep. 6, 2007, provisional application No. 61/069,071.

(51) Int. Cl.
| | |
|---|---|
| *A61K 31/44* | (2006.01) |
| *C07D 213/80* | (2006.01) |
| *A61K 47/48* | (2006.01) |
| *C07C 255/43* | (2006.01) |
| *C07D 211/90* | (2006.01) |
| *C07D 281/10* | (2006.01) |
| *C07D 413/04* | (2006.01) |
| *C07D 417/04* | (2006.01) |
| *A61K 31/4418* | (2006.01) |

(52) U.S. Cl.
CPC ....... *A61K 47/48215* (2013.01); *A61K 31/4418* (2013.01); *C07C 255/43* (2013.01); *C07D 211/90* (2013.01); *C07D 281/10* (2013.01); *C07D 413/04* (2013.01); *C07D 417/04* (2013.01)

(58) Field of Classification Search
CPC ................... A61K 47/48215; A61K 31/4418
USPC ........................................ 546/321; 514/356
See application file for complete search history.

(56) References Cited

U.S. PATENT DOCUMENTS

| | | | |
|---|---|---|---|
| 3,261,859 A | 7/1966 | Dengel | |
| 3,485,847 A | 12/1969 | Bossert et al. | |
| 3,562,257 A | 2/1971 | Kugita et al. | |
| 3,962,238 A | 6/1976 | Mauvernay et al. | |
| 3,985,758 A | 10/1976 | Murakami et al. | |
| 4,154,839 A | 5/1979 | Wehinger et al. | |
| RE30,577 E | 4/1981 | Busch et al. | |
| 4,264,611 A | 4/1981 | Berntsson et al. | |
| 4,327,725 A * | 5/1982 | Cortese et al. | 424/427 |
| 4,406,906 A | 9/1983 | Meyer et al. | |
| 4,466,972 A | 8/1984 | Neumann | |
| 4,552,695 A | 11/1985 | Igarashi et al. | |
| 4,572,909 A | 2/1986 | Campbell et al. | |
| 4,878,303 A * | 11/1989 | Banniza et al. | 40/606.14 |
| 4,879,303 A | 11/1989 | Davison et al. | |
| 5,672,662 A | 9/1997 | Harris et al. | |
| 8,748,648 B2 | 6/2014 | Ren et al. | |
| 2005/0136031 A1 | 6/2005 | Bentley et al. | |
| 2008/0021005 A1 | 1/2008 | Cheu et al. | |
| 2011/0098273 A1 | 4/2011 | Ren et al. | |

FOREIGN PATENT DOCUMENTS

| | | |
|---|---|---|
| BE | 615861 | 10/1962 |
| JP | 2005-148174 | 6/2005 |
| WO | WO 02/098949 | 12/2002 |
| WO | WO 03/084926 | 10/2003 |
| WO | WO 2005/058367 | 6/2005 |
| WO | WO 2008/112286 | 9/2008 |

OTHER PUBLICATIONS

Skrap, S. Justus Liebigs Annalen der Chemie 1919, 419, 1-92—abstract.*
Hinkel et al Journal of the Chemical Society 1929, 750-754—abstract.*
Mumm et al Berichte der Deutschen Chemischen Gesellschaft 1926, 59B, 1605-1616—abstract.*
Petrow, V. A. Journal of the Chemical Society 1946, 884-888—abstract.*
Kamal et al Pakistan Journal of Scientific Research 1963, 15, 35-42—abstract.*
Murakami et al US 4,021,434 (1977)—abstract.*
Chennat et al Journal of the Chemical Society, Perkins Trans 1: Organic and Bio-Organic Chemistry 1975, 10, 926-929—abstract.*
So et al JP 2005148174—abstract (2005).*
Angeles, et al., "Rearrangement of o-Nitrobenzaldehyde in the Hantzsch Reaction", Molecules, vol. 6, pp. 683-693, (2001).
Berntsson, et al., "Felodipine Analogs: Structure-Activity Relationships", Journal of Cardiovascular Pharmacology, vol. 10, (Supp. 1), pp. S60-S65, (1987).
Chen, et al., "Synthesis and Properties of ABA Amphiphiles," J. Org. Chem., vol. 64, pp. 6870-6873, (1999).
Clemens, et al., "Acetoacetylation with 2,2,6-Trimethyl-4H-1,3-dioxin-4-one: A Convenient Alternative to Diketene", J. Org. Chem., vol. 50, pp. 2431-2435, (1985).
Ertl, et al., "Fast Calculation of Molecular Polar Surface Area as a Sum of Fragment-Based Contributions and Its Application to the Prediction of Drug Transport Properties," J. Med. Chem., vol. 43, pp. 3714-3717, (2000).

(Continued)

*Primary Examiner* — John Mabry
(74) *Attorney, Agent, or Firm* — Timothy A. Marquart; Mark A. Wilson

(57) ABSTRACT

The invention provides small molecule drugs that are chemically modified by covalent attachment of a water soluble oligomer. A conjugate of the invention, when administered by any of a number of administration routes, exhibits characteristics that are different from the characteristics of the small molecule drug not attached to the water soluble oligomer.

6 Claims, No Drawings

(56) References Cited

OTHER PUBLICATIONS

Fassihi, et al., "Synthesis and Evaluation of Calcium Channel Antagonist Activity of New 1, 4-dihydropyridines Containing Phenylamineimidazolyl Substitute in Guinea-Pig Ileal Smooth Muscle", Journal of Research in Medical Sciences, vol. 1, pp. 5-10, (2004).

Fleckenstein, "Calcium Heart", Proc. Meet. Eur. Sect. Int. Study Group Res. Cardiac Metab, 1971, Meeting date 1970, 135-88—abstract.

Kappe, "4-Aryldihydropyrimidines via the Biginelli Condensation: Aza-Analogs of Nifedipine-Type Calcium Channel Modulators", Molecules, vol. 3, pp. 1-9, (1998).

Kelder, et al., "Polar Molecular Surface as a Dominating Determinant for Oral Absorption and Brain Penetration of Drugs," Pharm. Res., vol. 16, No. 10, pp. 1514-1519, (1999).

Kellogg, et al., "The Hantzsch 1,4-Dihydropyridine Synthesis as a Route to Bridged Pyridine and Dihydropyridine Crown Ethers", J. Org. Chem., vol. 45, pp. 2854-2861, (1980).

Kim, et al., "Synthesis of Amlodipine Using Aza Diels-Alder Reaction", Bull. Korean Chem. Soc., vol. 23, No. 1, pp. 143-144, (2002).

Soldatov, "Molecular Tools of Calcium Channel Studying: Synthesis and Evaluation of Biological Activity of Novel Dihydrophyridine Calcium Entry Blockers," Bioorg. Chem., vol. 17, pp. 141-158, (1989).

Triggle, "Calcium-Channel Drugs: Structure-Function Relationships and Selectivity of Action", Journal of Cardiovascular Pharmacology, vol. 18, (Suppl. 10), pp. S1-S6, (1991).

Walles, et al., "Verapamil: new insight into the molecular mechanism of drug oxidation in the human heart", Journal of Chromatography A., vol. 970, pp. 117-130, (2002).

PCT International Search Report and Written Opinion corresponding to PCT Application No. PCT/US2008/010385 date of mailing Jan. 11, 2012.

PCT International Preliminary Report on Patentability corresponding to PCT Application No. PCT/US2008/010385 date of mailing Dec. 15, 2011.

Enzon Pharmaceuticals, Macromolecular Engineering Technologies, pp. 1-14, (2004).

Nektar™—Transforming Therapeutics, Nektar Molecule Engineering: Polyethylene Glycol and Derivatives for Advanced PEGylation, pp. 1-20, Catalog—2003, (Jul. 2003).

Nektar™—Transforming Therapeutics, Nektar Advanced PEGylation: Polyethylene Glycol and Derivatives for Advanced PEGylation, pp. 1-24, Catalog—2004, (Jul. 2004).

Nektar™—Transforming Therapeutics, Nektar Advanced PEGylation: Polyethylene Glycol and Derivatives for Advanced PEGylation, pp. 1-30, (Catalog 2005-2006).

NOF Corporation, "PEG Derivatives, Phospholipid and Drug Delivery Materials for Pharmaceuticals", pp. 1-46, Catalogue 2003-1st, (Jan. 2003).

NOF Corporation, "PEG Derivatives, Phospholipid and Drug Delivery Materials for Pharmaceuticals", pp. 1-50, Catalogue 2003-2nd, (Mar. 2004).

NOF Corporation, "PEG Derivatives, Phospholipids and Drug Delivery Materials for Pharmaceutical Products and Formulations", pp. 1-59, Catalogue Ver. 8, (Apr. 2006).

Polypure, Products; PEG amines; PEG acids and amino acids; PEG thiols and disulfides; BIOTINS, (Apr. 2004).

Polypure, Products; PEG amines; PEG acids and amino acids; PEG thiols and disulfides; BIOTINS, (Apr. 2005).

Quanta Biodesign, Labeling, Derivatization and Crosslinking Reagents for Biological and Related Materials with dPEG™, pp. 1-38, (Mar. 12, 2004).

Quanta Biodesign, Labeling, Modification and Crosslinking Reagents incorporating our unique monodispersed dPEG™ Technology, pp. 1-31, (Nov. 5, 2004).

Quanta Biodesign, Ltd., Leading innovator, producer and provider of monodisperse discrete PEG™ (dPEG™) derivatives, (Product Catalog), pp. 1-51, (Updated: Jul. 18, 2005).

Quanta Biodesign, Ltd., Leading innovator, producer and provider of monodisperse discrete PEG™ (dPEG™) derivatives, (Product Catalog), pp. 1-51, (Updated: Nov. 17, 2005).

Shearwater Polymers, Inc., Polyethylene Glycol and Derivatives, pp. 1-49, (Catalog—Mar. 1995).

Shearwater Polymers, Inc., Polyethylene Glycol and Derivatives, pp. 1-53, (Catalog—Jul. 1997).

Shearwater Polymers, Inc., Polyethylene Glycol and Derivatives: Functionalized Biocompatible Polymers for Research and Pharmaceuticals, pp. 1-50, (Catalog—Jan. 2000).

Shearwater Corporation, Polyethylene Glycol and Derivatives for Biomedical Applications, pp. 1-17, (Catalog—Jul. 2001).

Chennat, et al., "A New Synthesis of 1,4-Dihydropyridines", Journal of the Chemical Society Perkin Transactions 1: Organic and Bio-Organic Chemistry, vol. 10, pp. 926-929, (1975).

Hinkel, et al., "Substituted Aromatic Aldehydes in Hantzsch's Pyridine Condensation. Part I. Methoxy-Chloro-, and Hydroxy-benzaldehydes", Journal of the Chemical Society, pp. 750-754, (1929).

Mumm, et al., "N,N'-Dialkyl-[tetrahydrodipyridyls]", Berichte der Deutschen Chemischen Gesellschaft [Albteilung] B: Abhandlungen, 59B, pp. 1605-1616, (1926). (With English abstract). (With English abstract).

Petrow, "New Syntheses of Heterocyclic Compounds. Part VII. 9-Amino-6: 8-dimethyl-7: 10-diazaphenanthrenes", Journal of the Chemical Society, pp. 884-888.

Skraup, "Additionsreaktionen und Ringspaltungen einiger heterocyclischer Verbindungen", Justus Liebigs Annalen der Chemie, 419, pp. 1-92, (1919). (With English abstract).

\* cited by examiner

OLIGOMER-CALCIUM CHANNEL BLOCKER CONJUGATES

CROSS REFERENCE TO RELATED APPLICATIONS

This application is a continuation of U.S. patent application Ser. No. 12/674,139, filed 05 Jan. 2011, now U.S. Pat. No. 8,748,648, which is a 35 U.S.C. §371 application of International Application No. PCT/US2008/010385, filed 03 Sep. 2008, designating the U.S., which claims the benefit of priority under 35 U. S. C. §119(e) to Provisional Application Ser. Nos. 60/967,764, filed 06 Sep. 2007, and 61/069,071, filed 12 Mar. 2008, all of which are incorporated herein by reference in their entireties.

FIELD OF THE INVENTION

This invention provides (among other things) chemically modified calcium channel blockers that possess certain advantages over calcium channel blockers lacking the chemical modification. The chemically modified calcium channel blockers described herein relate to and/or have application(s) in (among others) the fields of drug discovery, pharmacotherapy, physiology, organic chemistry and polymer chemistry.

BACKGROUND OF THE INVENTION

Drugs currently known as calcium channel blockers (CCB) (also called calcium antagonists), among other actions, inhibit calcium-evoked contractions in depolarized smooth muscles. Blocking the entry of calcium reduces the active tone of vascular smooth muscle and produces vasodilatation. This pharmacological property has, at a minimum, been one of the bases for the use of CCBs in the management of hypertension and coronary heart disease. CCBs may have other effects that help prevent the primary complications of hypertension, such as atherosclerosis, stroke, peripheral arterial disease, heart failure and end-state renal disease. CCBs are prescribed for the treatment and/or prophylaxis of vasospastic angina, including spontaneous coronary artery spasm presenting as Prinzmetal's angina, chronic stable angina, unstable angina, arrhythmias, such as arrhythmias associated with digitalis therapy, and arrhythmias associated with stress in chronic arterial flutter or arterial fibrillation, supraventricular tachyrrhythmias, paroxysmal supraventricular tachycardia, and subarachnoid hemorrhage. In addition, CCBs are prescribed for treatment and/or prevention of reinfarction of non-Q-wave myocardial infarction, tardive dyskinesia, Raynaud's syndrome, coronary heart disease, migraine, pulmonary hypertension, asthma, preterm labor, severe pregnancy-associated hypertension, esophageal disorders, biliary and renal colic, cardiomyopathy, coronary artery disease, and depression. As a class, CCBs represent an important and useful tool in pharmacotherapy.

Many CCBs can be divided into three categories based on their chemical structure; these three categories are diphenylalkylamines, benzothiazepines, and dihydropyridines.

With respect to the diphenylalkylamines, verapamil (described in U.S. Pat. No. 3,261,859) is one member of this category of CCBs, along with 2-(3,4-dimethoxyphenyl)-5-[2-(3,4-dimethoxyphenyl)ethyl-methyl-amino]-2-(1-methylethyl)pentanenitrile, the structure of which is shown immediately below.

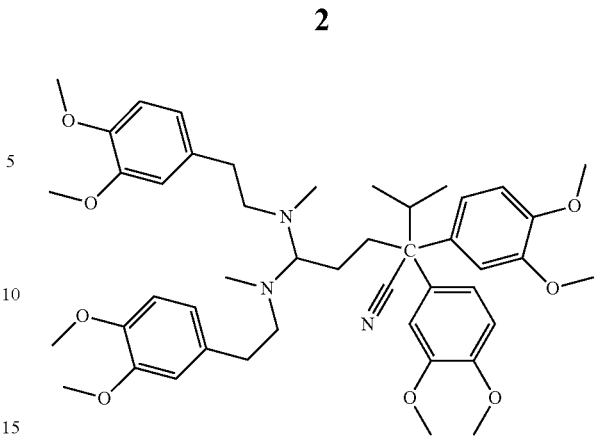

2-(3,4-dimethoxyphenyl)-5-[2-(3,4-dimethoxyphenyl) ethyl-methyl-amino]-2-(1-methylethyl)pentanenitrile With respect to benzothiazepines, diltiazem (described in U.S. Pat. No. 3,562,257) is one member of this category of CCBs. The chemical name of diltiazem is [2-(2-dimethylaminoethyl)-5-(4-methoxyphenyl)-3-oxo-6-thia-2-azabicyclo[5.4.0]undeca-7,9,11-trien-4-yl]ethanoate. The structure of diltiazem is shown immediately below.

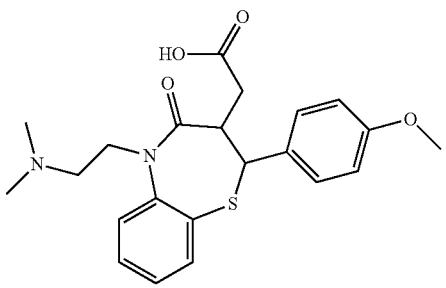

Diltiazem

With respect to the dihydropyridines, amlodipine (described in U.S. Pat. No. 4,572,909), felodipine (described in U.S. Pat. No. 4,264,611), isradipine (described in U.S. Pat. No. 4,466,972), nicardipine (described in U.S. Pat. No. 3,985,758), nifedipine (described in U.S. Pat. No. 3,485,847), nimodipine (described in U.S. Pat. No. 4,406,906), and nisoldipine (described in U.S. Pat. No. 4,154,839) are each members of this category of CCBs. The structure of each of the aforementioned dihydropyridines is shown immediately below.

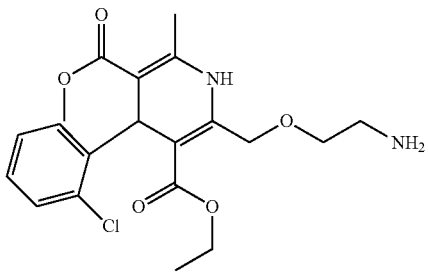

Amlodipine

-continued

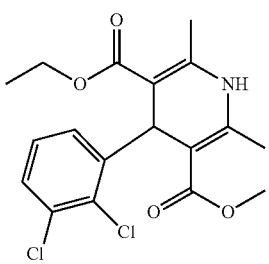

Felodipine

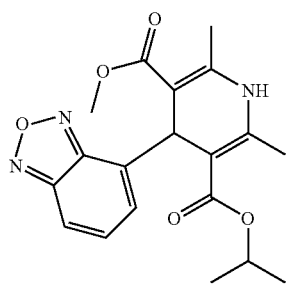

Isradipine

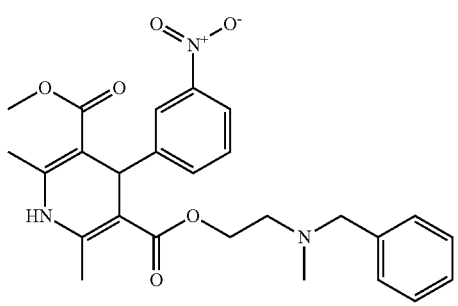

Nicardipine

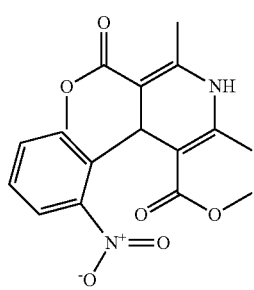

Nifedipine

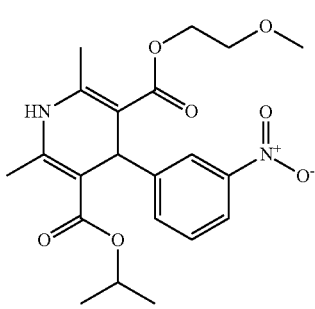

Nimodipine

-continued

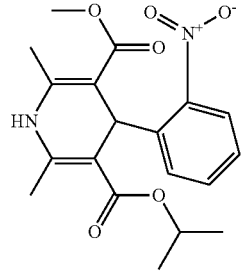

Nisoldipine

Although not easily placed within any of the three previously mentioned categories of CCB's, bepridil (described in U.S. Pat. No. 3,962,238 and RE 30,577) is another CCB. The structure of bepridil is shown immediately below

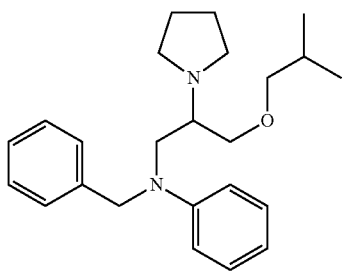

Bepridil

Although CCBs serve an important role in treating patients, their use is sometimes associated with (among other things) extensive metabolism, often resulting in inactive metabolites and thus lower bioavailability. CCBs also exhibit several side effects of the cardiovascular and central nervous systems, as well as dermatologic, gastrointestinal, and hematological adverse effects. Research is ongoing to improve the bioavailability of CCBs and to reduce side effects associated with CCB therapy. Thus, there is a need to provide CCBs with improved pharmacological properties.

The present invention seeks to address these and other needs in the art by providing (among other things) a conjugate of a water-soluble and non-peptidic oligomer and calcium channel blocker.

SUMMARY OF THE INVENTION

In one or more embodiments of the invention, a compound is provided, the compound comprising a residue of a calcium channel blocker covalently attached via a stable or degradable linkage to a water-soluble and non-peptidic oligomer.

In one or more embodiments of the invention, a compound is provided, the compound comprising a residue of a calcium channel blocker covalently attached via a stable or degradable linkage to a water-soluble and non-peptidic oligomer, wherein the calcium channel blocker has a structure encompassed by the following formula:

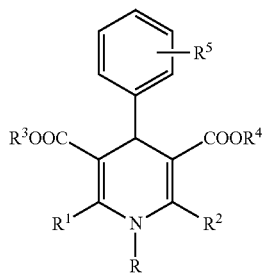

Formula I wherein (with respect to this Formula I):

R is hydrogen or lower alkyl;

$R^1$ and $R^2$ are each independently selected from the group consisting of hydrogen, substituted lower alkyl, unsubstituted lower alkyl, and —YOYNR$^6$R$^7$, where each Y is independently lower alkylene and $R^6$ and $R^7$ are each independently selected from group consisting of hydrogen, unsubstituted lower alkyl, substituted lower alkyl, cycloalkyl, aryl and alkylaryl;

$R^3$ and $R^4$ are each independently selected from the group consisting of hydrogen, unsubstituted lower alkyl, substituted lower alkyl, and —YNR$^6$R$^7$, where Y is lower alkylene and $R^6$ and $R^7$ are each independently selected from group consisting of hydrogen, unsubstituted lower alkyl, substituted lower alkyl, cycloalkyl, aryl and alkylaryl; and each $R^5$ is independently selected from group consisting of hydrogen, unsubstituted lower alkyl, substituted lower alkyl, chloro, fluoro and nitro, and optical isomers, diastereomers, and enantiomers thereof. Optionally, the compound can be combined with a pharmaceutically acceptable excipient to form a composition.

In one embodiment, R is hydrogen. In another embodiment, R is methylethyl. In another embodiment, R is methylpropyl.

In one embodiment $R^1$ is methyl. In another embodiment $R^1$ is CH$_2$OCH$_2$CH$_2$NH$_2$.

In one embodiment $R^2$ is methyl. In another embodiment $R^2$ is CH$_2$OCH$_2$CH$_2$NH$_2$.

In one embodiment $R^3$ is hydrogen. In another embodiment $R^3$ is methyl. In another embodiment $R^3$ is ethyl. In another embodiment $R^3$ is methylethyl. In another embodiment $R^3$ is methoxyethyl. In another embodiment $R^3$ is 2-(benzyl-methyl-amino)ethyl.

In one embodiment $R^4$ is hydrogen. In another embodiment $R^4$ is methyl. In another embodiment $R^4$ is ethyl. In another embodiment $R^4$ is methylethyl. In another embodiment $R^4$ is methoxyethyl. In another embodiment $R^4$ is 2-(benzyl-methyl-amino)ethyl.

In one embodiment $R^5$ is hydrogen. In another embodiment $R^5$ is chloro. In another embodiment one $R^5$ is 2-chloro and another $R^5$ is 3-chloro. In another embodiment $R^5$ is nitro.

In one or more embodiments of the invention, a dosage form is provided, the dosage form comprising a compound comprising a residue of a calcium channel blocker covalently attached via a stable or degradable linkage to a water-soluble and non-peptidic oligomer.

In one or more embodiments of the invention, a method is provided, the method comprising covalently attaching a water-soluble and non-peptidic oligomer to a calcium channel blocker.

In one or more embodiments of the invention, a method is provided, the method comprising administering a compound comprising a residue of a calcium channel blocker covalently attached via a stable or degradable linkage to a water-soluble and non-peptidic oligomer.

These and other objects, aspects, embodiments and features of the invention may become more fully apparent when read in conjunction with the following detailed description.

BRIEF DESCRIPTION OF THE FIGURES

This paragraph intentionally left blank.

DETAILED DESCRIPTION OF THE INVENTION

It must be noted that, as used in this specification, the singular forms "a," "an," and "the" include plural referents unless the context clearly dictates otherwise.

In describing and claiming the present invention, the following terminology will be used in accordance with the definitions described below.

"Water soluble and non-peptidic oligomer" indicates an oligomer that is at least 35% (by weight) soluble, and preferably greater than 95% soluble, in water at room temperature. An unfiltered aqueous preparation of a "water-soluble" oligomer transmits at least 75%, more preferably at least 95%, of the amount of light transmitted by the same solution after filtering. On a weight basis, a "water soluble" oligomer is preferably at least 35% (by weight) soluble in water, more preferably at least 50% (by weight) soluble in water, still more preferably at least 70% (by weight) soluble in water, and still more preferably at least 85% (by weight) soluble in water. It is preferred, however, that the water-soluble oligomer is at least 95% (by weight) soluble in water or completely soluble in water.

The terms "monomer," "monomeric subunit" and "monomeric unit" are used interchangeably herein and refer to one of the basic structural units of a polymer or oligomer. In the case of a homo-oligomer, this is defined as a structural repeating unit of the oligomer. In the case of a co-oligomer, a monomeric unit is more usefully defined as the residue of a monomer which was oligomerized to form the oligomer, since the structural repeating unit may include more than one type of monomeric unit. Preferred oligomers of the invention are homo-oligomers.

An "oligomer" is a molecule possessing from about 1 to about 30 monomers. Specific oligomers for use in the invention include those having a variety of geometries such as linear, branched, or forked, to be described in greater detail below.

"PEG" or "polyethylene glycol," as used herein, is meant to encompass any water-soluble poly(ethylene oxide). Unless otherwise indicated, a "PEG oligomer" or an oligoethylene glycol is one in which substantially all (preferably all) monomeric subunits are ethylene oxide subunits, though the oligomer may contain distinct end capping moieties or functional groups, e.g., for conjugation. PEG oligomers for use in the present invention may comprise of following structures: "—(CH$_2$CH$_2$O)$_n$—" or "—(CH$_2$CH$_2$O)$_{n-1}$CH$_2$CH$_2$—," depending upon whether or not the terminal oxygen(s) has been displaced, e.g., during a synthetic transformation. As stated above, for the PEG oligomers, the variable (n) ranges from 1 to 30, and the terminal groups and architecture of the overall PEG can vary. When PEG further comprises a functional group, A, for linking to, e.g., a small molecule drug, the functional group when covalently attached to a PEG oligomer, does not result in formation of (i) an oxygen-oxygen bond (—O—O—, a peroxide linkage), or (ii) a nitrogen-oxygen bond (N—O, O—N).

The terms "end-capped" or "terminally capped" are interchangeably used herein to refer to a terminal or endpoint of a polymer having an end-capping moiety. Typically, although not necessarily, the end-capping moiety comprises a hydroxy or $C_{1-20}$ alkoxy group. Thus, examples of end-capping moieties include alkoxy (e.g., methoxy, ethoxy and benzyloxy), as well as aryl, heteroaryl, cyclo, heterocyclo, and the like. In addition, saturated, unsaturated, substituted and unsubstituted forms of each of the foregoing are envisioned. Moreover, the end-capping group can also be a silane. The end-capping group can also advantageously comprise a detectable label. When the polymer has an end-capping group comprising a detectable label, the amount or location of the polymer and/or the moiety (e.g., active agent) of interest to which the polymer is coupled, can be determined by using a suitable detector. Such labels include, without limitation, fluorescers, chemiluminescers, moieties used in enzyme labeling, colorimetric moieties (e.g., dyes), metal ions, radioactive moieties, and the like. Suitable detectors include photometers, films, spectrometers, and the like.

"Branched", in reference to the geometry or overall structure of an oligomer, refers to an oligomer having two or more polymer "arms" extending from a branch point.

"Forked" in reference to the geometry or overall structure of an oligomer, refers to an oligomer having two or more functional groups (through one or more atoms) extending from a branch point.

A "branch point" refers to a bifurcation point comprising one or more atoms at which an oligomer branches or forks from a linear structure into one or more additional arms.

The term "reactive" or "activated" refers to a functional group that reacts readily or at a practical rate under conventional conditions of organic synthesis. This is in contrast to those groups that either do not react or require strong catalysts or impractical reaction conditions in order to react (i.e., a "nonreactive" or "inert" group).

"Not readily reactive," with reference to a functional group present on a molecule in a reaction mixture, indicates that the group remains largely intact under conditions effective to produce a desired reaction in the reaction mixture.

A "protecting group" is a moiety that prevents or blocks reaction of a particular chemically reactive functional group in a molecule under certain reaction conditions. The protecting group may vary depending upon the type of chemically reactive group being protected as well as the reaction conditions to be employed and the presence of additional reactive or protecting groups in the molecule. Functional groups which may be protected include, by way of example, carboxylic acid groups, amino groups, hydroxyl groups, thiol groups, carbonyl groups and the like. Representative protecting groups for carboxylic acids include esters (such as a p-methoxybenzyl ester), amides and hydrazides; for amino groups, carbamates (such as tert-butoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protecting Groups in Organic Synthesis*, Third Edition, Wiley, New York, 1999, and references cited therein.

A functional group in "protected form" refers to a functional group bearing a protecting group. As used herein, the term "functional group" or any synonym thereof is meant to encompass protected forms thereof.

A "physiologically cleavable" or "hydrolyzable" or "degradable" bond is a relatively labile bond that reacts with water (i.e., is hydrolyzed) under physiological conditions. The tendency of a bond to hydrolyze in water may depend not only on the general type of linkage connecting two central atoms but also on the substituents attached to these central atoms. Appropriate hydrolytically unstable or weak linkages include but are not limited to carboxylate ester, phosphate ester, anhydrides, acetals, ketals, acyloxyalkyl ether, imines, orthoesters, peptides, oligonucleotides, thioesters, thiolesters, and carbonates.

An "enzymatically degradable linkage" means a linkage that is subject to degradation by one or more enzymes.

A "stable" linkage or bond refers to a chemical bond that is substantially stable in water, that is to say, does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, urethanes, amines, and the like. Generally, a stable linkage is one that exhibits a rate of hydrolysis of less than about 1-2% per day under physiological conditions. Hydrolysis rates of representative chemical bonds are found in standard chemistry textbooks.

"Substantially" or "essentially" means nearly totally or completely, for instance, 95% or greater, more preferably 97% or greater, still more preferably 98% or greater, even more preferably 99% or greater, yet still more preferably 99.9% or greater, yet still more preferably with 99.99% or greater of some given quantity.

"Monodisperse" refers to an oligomer composition wherein substantially all of the oligomers in the composition have a well-defined, single (i.e., the same) molecular weight and defined number of monomers, as determined by chromatography or mass spectrometry. Monodisperse oligomer compositions are in one sense pure, that is, substantially having a single and definable number (as a whole number) of monomers rather than a large distribution. A monodisperse oligomer composition possesses a MW/Mn value of 1.0005 or less, and more preferably, a MW/Mn value of 1.0000. By extension, a composition comprised of monodisperse conjugates means that substantially all oligomers of all conjugates in the composition have a single and definable number (as a whole number) of monomers rather than a large distribution and would possess a MW/Mn value of 1.0005, and more preferably, a MW/Mn value of 1.0000 if the oligomer were not attached to the moiety derived from a small molecule drug. A composition comprised of monodisperse conjugates may, however, include one or more nonconjugate substances such as solvents, reagents, excipients, and so forth.

"Bimodal," in reference to an oligomer composition, refers to an oligomer composition wherein substantially all oligomers in the composition have one of two definable and different numbers (as whole numbers) of monomers rather than a large distribution, and whose distribution of molecular weights, when plotted as a number fraction versus molecular weight, appears as two separate identifiable peaks. Preferably, for a bimodal oligomer composition as described herein, each peak is symmetric about its mean, although the size of the two peaks may differ. Ideally, the polydispersity index of each peak in the bimodal distribution, Mw/Mn, is 1.01 or less, more preferably 1.001 or less, and even more preferably 1.0005 or less, and even more preferably a MW/Mn value of 1.0000. By extension, a composition comprised of bimodal conjugates means that substantially all oligomers of all conjugates in the composition have one of two definable and different numbers (as whole numbers) of monomers rather than a large distribution and would possess a MW/Mn value of 1.01 or less, more preferably 1.001 or less and even more preferably 1.0005 or less, and even more preferably a MW/Mn value of 1.0000 if the oligomer were not attached to the moiety derived from a small molecule drug. A composition comprised of bimodal conjugates may, however, include one or more nonconjugate substances such as solvents, reagents, excipients, and so forth A "calcium channel blocker" refers to an organic, inorganic, or organometallic compound having a molecular weight of less than about 1000 Daltons and having some degree of activity as an antagonist of calcium channels. A calcium channel blocker is also referred to as a calcium channel blocking agent. Calcium channel blockers of the invention encompass oligopeptides and other biomolecules having a molecular weight of less than about 1000.

A "biological membrane" is any membrane made of cells or tissues, that serves as a barrier to at least some foreign entities or otherwise undesirable materials. As used herein a "biological membrane" includes those membranes that are associated with physiological protective barriers including, for example: the blood-brain barrier; the blood-cerebrospinal fluid barrier; the blood-placental barrier; the blood-milk barrier; the blood-testes barrier; and mucosal barriers including the vaginal mucosa, urethral mucosa, anal mucosa, buccal mucosa, sublingual mucosa, and rectal mucosa. Unless the context clearly dictates otherwise, the term "biological membrane" does not include those membranes associated with the middle gastro-intestinal tract (e.g., stomach and small intestines).

A "biological membrane crossing rate," provides a measure of a compound's ability to cross a biological barrier, such as the blood-brain barrier ("BBB"). A variety of methods may be used to assess transport of a molecule across any given biological membrane. Methods to assess the biological membrane crossing rate associated with any given biological barrier (e.g., the blood-cerebrospinal fluid barrier, the blood-placental barrier, the blood-milk barrier, the intestinal barrier, and so forth), are known, described herein and/or in the relevant literature, and/or may be determined by one of ordinary skill in the art.

A "reduced rate of metabolism" refers to a measurable reduction in the rate of metabolism of a water-soluble oligomer-small molecule drug conjugate as compared to rate of metabolism of the small molecule drug not attached to the water-soluble oligomer (i.e., the small molecule drug itself) or a reference standard material. In the special case of "reduced first pass rate of metabolism," the same "reduced rate of metabolism" is required except that the small molecule drug (or reference standard material) and the corresponding conjugate are administered orally. Orally administered drugs are absorbed from the gastro-intestinal tract into the portal circulation and may pass through the liver prior to reaching the systemic circulation. Because the liver is the primary site of drug metabolism or biotransformation, a substantial amount of drug may be metabolized before it reaches the systemic circulation. The degree of first pass metabolism, and thus, any reduction thereof, may be measured by a number of different approaches. For instance, animal blood samples may be collected at timed intervals and the plasma or serum analyzed by chromatography/mass spectrometry for metabolite levels. Other techniques for measuring a "reduced rate of metabolism" associated with the first pass metabolism and other metabolic processes are known, described herein and/or in the relevant literature, and/or may be determined by one of ordinary skill in the art. Preferably, a conjugate of the invention can provide a reduced rate of metabolism reduction satisfying at least one of the following values: at least about 5%; at least about 10%; at least about 15%; least about 20%; at least about 25%; at least about 30%; at least about 40%; at least about 50%; at least about 60%; at least about 70%; at least about 80%; and at least about 90%.

A compound (such as a small molecule drug or conjugate thereof) that is "orally bioavailable" is one that possesses a bioavailability when administered orally of greater than 1%, and preferably greater than 10%, where a compound's bioavailability is the fraction of administered drug that reaches the systemic circulation in unmetabolized form.

"Alkyl" refers to a hydrocarbon chain, ranging from about 1 to 20 atoms in length. Such hydrocarbons are preferably but not necessarily saturated and may be branched or straight chain. Exemplary alkyl groups include methyl, ethyl, propyl, butyl, pentyl, 2-methylbutyl, 2-ethylpropyl, 3-methylpentyl, and the like. As used herein, "alkyl" includes cycloalkyl when three or more carbon atoms are referenced.

"Lower alkyl" refers to an alkyl group containing from 1 to 6 carbon atoms, and may be straight chain or branched, as exemplified by methyl, ethyl, n-butyl, i-butyl, t-butyl.

"Non-interfering substituents" are those groups that, when present in a molecule, are non-reactive with other functional groups contained within the molecule.

"Alkoxy" refers to an —O—R group, wherein R is alkyl or substituted alkyl, preferably $C_1$-$C_{20}$ alkyl (e.g., methoxy, ethoxy, propyloxy, etc.), preferably $C_1$-$C_7$.

"Electrophile" refers to an ion, atom, or an ionic or neutral collection of atoms having an electrophilic center, i.e., a center that is electron seeking, capable of reacting with a nucleophile.

"Nucleophile" refers to an ion or atom or an ionic or neutral collection of atoms having a nucleophilic center, i.e., a center that is seeking an electrophilic center, and capable of reacting with an electrophile.

"Pharmaceutically acceptable excipient" or "pharmaceutically acceptable carrier" refers to an excipient that may be included in the compositions of the invention and that causes no significant adverse toxicological effects to the patient.

"Pharmacologically effective amount," "physiologically effective amount," and "therapeutically effective amount" are used interchangeably herein to mean the amount of a water-soluble oligomer-small molecule drug conjugate present in a composition that is needed to provide a desired level of active agent and/or conjugate in the bloodstream or in the target tissue. The precise amount may depend upon numerous factors, e.g., the particular active agent, the components and physical characteristics of the composition, intended patient population, patient considerations, and may readily be determined by one skilled in the art, based upon the information provided herein and available in the relevant literature.

A "difunctional" oligomer is an oligomer having two functional groups contained therein, typically at its termini. When the functional groups are the same, the oligomer is said to be homodifunctional. When the functional groups are different, the oligomer is said to be heterobifunctional.

A basic or acidic reactant described herein includes neutral, charged, and any corresponding salt forms thereof.

The term "patient," refers to a living organism suffering from or prone to a condition that may be prevented or treated by administration of a conjugate as described herein and includes both humans and animals.

"Optional" or "optionally" means that the subsequently described circumstance may or may not occur, so that the description includes instances where the circumstance occurs and instances where it does not.

As indicated above, the present invention is directed to (among other things) a compound comprising a residue of a calcium channel blocker covalently attached via a stable or degradable linkage to a water-soluble and non-peptidic oligomer.

In one or more embodiments of the invention, a compound is provided, the compound comprising a residue of a calcium channel blocker covalently attached via a stable or degradable linkage to a water-soluble and non-peptidic oligomer, wherein the calcium channel blocker has a structure encompassed by the following formula:

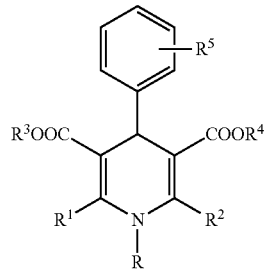

Formula I wherein (with respect to this Formula I):

R is hydrogen or lower alkyl;

$R^1$ and $R^2$ are each independently selected from the group consisting of hydrogen, substituted lower alkyl, unsubstituted lower alkyl, and —YOYNR$^6$R$^7$, where each Y is independently lower alkylene and $R^6$ and $R^7$ are each independently selected from group consisting of hydrogen, unsubstituted lower alkyl, substituted lower alkyl, cycloalkyl, aryl and alkylaryl;

$R^3$ and $R^4$ are each independently selected from the group consisting of hydrogen, unsubstituted lower alkyl, substituted lower alkyl, and —YNR$^6$R$^7$, where Y is lower alkylene and $R^6$ and $R^7$ are each independently selected from group consisting of hydrogen, unsubstituted lower alkyl, substituted lower alkyl, cycloalkyl, aryl and alkylaryl; and each $R^5$ is independently selected from group consisting of hydrogen, unsubstituted lower alkyl, substituted lower alkyl, chloro, fluoro and nitro. Pharmaceutically acceptable salts of the compounds are also contemplated. Optionally, the compound can be combined with a pharmaceutically acceptable excipient to form a composition.

In one embodiment, R is hydrogen. In another embodiment, R is methylethyl. In another embodiment, R is methylpropyl.

In one embodiment $R^1$ is methyl. In another embodiment $R^1$ is CH$_2$OCH$_2$CH$_2$NH$_2$.

In one embodiment $R^2$ is methyl. In another embodiment $R^2$ is CH$_2$OCH$_2$CH$_2$NH$_2$.

In one embodiment $R^3$ is hydrogen. In another embodiment $R^3$ is methyl. In another embodiment $R^3$ is ethyl. In another embodiment $R^3$ is methylethyl. In another embodiment $R^3$ is methoxyethyl. In another embodiment $R^3$ is 2-(benzyl-methyl-amino)ethyl.

In one embodiment $R^4$ is hydrogen. In another embodiment $R^4$ is methyl. In another embodiment $R^4$ is ethyl. In another embodiment $R^4$ is methylethyl. In another embodiment $R^4$ is methoxyethyl. In another embodiment $R^4$ is 2-(benzyl-methyl-amino)ethyl.

In one embodiment $R^5$ is hydrogen. In another embodiment $R^5$ is chloro. In another embodiment one $R^5$ is 2-chloro and another $R^5$ is 3-chloro. In another embodiment $R^5$ is nitro.

In one or more embodiments of the invention, a compound is provided, the compound comprising a residue of a calcium channel blocker covalently attached via a stable or degradable linkage to a water-soluble and non-peptidic oligomer, wherein the calcium channel blocker has a structure encompassed by the following formula:

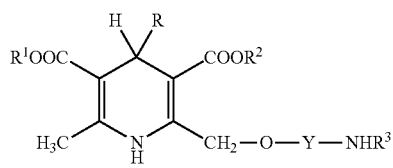

Formula II wherein (with respect to this Formula II):

Y is selected from the group consisting of —(CH$_2$)$_2$—, —(CH$_2$)$_3$—, —CH$_2$CH(CH$_3$) and —CH$_2$C(CH$_3$)$_2$—;

R is aryl;

$R^1$ and $R^2$ are each independently C$_1$-C$_4$ alkyl or 2-methoxyethyl; and $R^3$ is selected from the group consisting of hydrogen, C$_1$-C$_4$ alkyl, 2-(C$_1$-C$_4$ alkoxy)ethyl, cyclopropylmethyl, benzyl, and —(CH$_2$)$_m$COR$^4$ where m is 1, 2, or 3 and $R^4$ is hydroxyl, C$_1$-C$_4$ alkoxy or NR$^5$R$^6$ where $R^5$ and $R^6$ are independently hydrogen or C$_1$-C$_4$ alkyl. Preferably, aryl is: phenyl; phenyl substituted by one or two of nitro, halo, C$_1$-C$_4$ alkyl, C$_1$-C$_4$ alkoxy, hydroxy, trifluoromethyl or cyano; 1-naphthyl; or 2-naphthyl. Pharmaceutically acceptable salts (such as acid addition salts) of the compounds are also contemplated. Optionally, the compound can be combined with a pharmaceutically acceptable excipient to form a composition. CCBs encompassed by Formula II may be synthesized using processes known to one skilled in the art and are also disclosed in U.S. Pat. No. 4,572,909.

In one or more embodiments of the invention, a compound is provided, the compound comprising a residue of a calcium channel blocker covalently attached via a stable or degradable linkage to a water-soluble and non-peptidic oligomer, wherein the calcium channel blocker has a structure encompassed by the following formula:

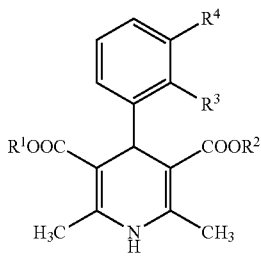

Formula III wherein (with respect to this Formula III):

$R^1$ is selected from the group consisting of —CH$_3$, —C$_2$H$_5$, —CH$_2$CH$_2$OCH$_3$ and CH$_2$CH$_2$OC$_2$H$_5$;

$R^2$ is selected from the group consisting of —CH$_2$CH$_3$, —CH(CH$_3$)$_2$, —C(CH$_3$)$_3$, —CH(CH$_3$)CH$_2$OCH$_3$, —C(CH$_3$)$_2$CH$_2$OCH$_3$ and —CH$_2$C(CH$_3$)═CH$_2$. In some instances, it is preferred that $R^1$ and $R^2$ are not the same, $R^3$ is chloro and $R^4$ is selected from the group consisting of chloro and methyl. Pharmaceutically acceptable salts of the compounds are also contemplated. Optionally, the compound can be combined with a pharmaceutically acceptable excipient to form a composition. CCBs encompassed by Formula III may be synthesized using processes known to one skilled in the art and are also disclosed in U.S. Pat. No. 4,264,611.

In one or more embodiments of the invention, a compound is provided, the compound comprising a residue of a calcium channel blocker covalently attached via a stable or degradable linkage to a water-soluble and non-peptidic oligomer, wherein the calcium channel blocker has a structure encompassed by the following formula:

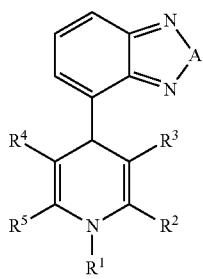

Formula IV wherein (with respect to Formula IV):
$R^1$ is hydrogen or $C_{1-6}$ alkyl;
$R^2$ and $R^5$ are independently hydrogen or $C_{1-6}$ alkyl;
$R^3$ and $R^4$ are independently are $COOR^7$ or —OOC-A-$NR^8R^9$, wherein $R^7$ is independently $C_{1-6}$ alkyl, $C_{3-7}$ cycloalkyl, $C_{7-10}$ phenylalkyl or $C_{3-6}$ alkoxyalkyl, A is $C_{1-6}$ alkylene, and $R^8$ and $R^9$ are independently, is $C_{1-6}$ alkyl or $C_{7-10}$ phenylalkyl; and
A is oxygen or sulphur.

Pharmaceutically acceptable salts (such as acid addition salts) of the compounds are also contemplated. Optionally, the compound can be combined with a pharmaceutically acceptable excipient to form a composition. CCBs encompassed by Formula IV may be synthesized using processes known to one skilled in the art and are also disclosed in U.S. Pat. No. 4,466,972.

In one or more embodiments of the invention, a compound is provided, the compound comprising a residue of a calcium channel blocker covalently attached via a stable or degradable linkage to a water-soluble and non-peptidic oligomer, wherein the calcium channel blocker has a structure encompassed by the following formula:

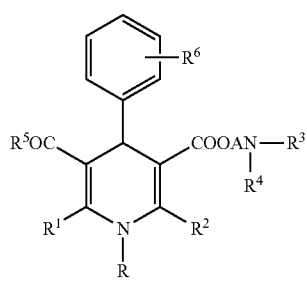

Formula V wherein (with respect to Formula V):
R is hydrogen or lower alkyl;
$R^1$ and $R^2$ are each methyl;
$R^3$ is selected from the group consisting of phenyl, benzyl, halobenzyl, lower alkoxy-benzyl;
$R^4$ is selected from the group consisting of hydrogen, methyl and ethyl;
A is lower alkylene;

$R^5$ is selected from the group consisting of methyl, lower alkoxy, lower alkoxy substituted lower alkoxy and O-A-$NR^3R^4$, where $R^3$ and $R^4$ have the same meaning as above; and
$R^6$ is nitro or trifluoromethyl.

Pharmaceutically acceptable salts of the compounds are also contemplated. Optionally, the compound can be combined with a pharmaceutically acceptable excipient to form a composition. CCBs encompassed by Formula V may be synthesized using processes known to one skilled in the art and are also disclosed in U.S. Pat. No. 3,985,758.

In one or more embodiments of the invention, a compound is provided, the compound comprising a residue of a calcium channel blocker covalently attached via a stable or degradable linkage to a water-soluble and non-peptidic oligomer, wherein the calcium channel blocker has a structure encompassed by the following formula:

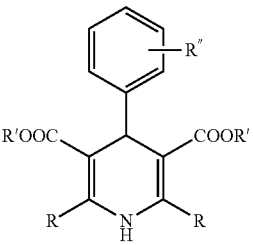

Formula VI wherein (with respect to Formula VI):
each R is independently selected from hydrogen and lower alkyl;
each R' is independently selected from lower alkyl; and
R" is selected from the group consisting of hydrogen, 2,4-dinitro, amino, di-lower alkylamino, 3-amino-4-chloro, 3-amino-6-chloro, 3-nitro-4-dilower alkylamino, 3-nitro-4-chloro and 3-nitro-6-chloro. Pharmaceutically acceptable salts of the compounds are also contemplated. Optionally, the compound can be combined with a pharmaceutically acceptable excipient to form a composition. CCBs encompassed by Formula VI may be synthesized using processes known to one skilled in the art and are also disclosed in U.S. Pat. No. 3,485,847.

In one or more embodiments of the invention, a compound is provided, the compound comprising a residue of a calcium channel blocker covalently attached via a stable or degradable linkage to a water-soluble and non-peptidic oligomer, wherein the calcium channel blocker has a structure encompassed by the following formula:

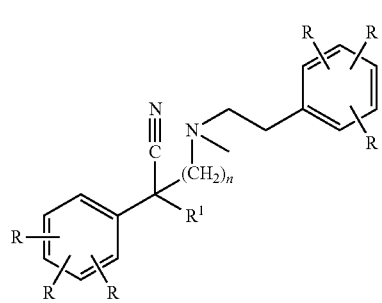

Formula VII wherein (with respect to Formula VII):
$R^1$ is a member selected from the group consisting of lower alkyl, cyclohexyl, and phenyl;

each R is independently selected from the group consisting of hydrogen, chlorine, lower alkoxy and lower alkyl (and preferably at least one R is chlorine, lower alkoxy and lower alkyl); and (n) is an integer from 2 to 3, inclusive.

Pharmaceutically acceptable salts (such as acid addition salts) of the compounds are also contemplated. Optionally, the compound can be combined with a pharmaceutically acceptable excipient to form a composition. CCBs encompassed by Formula VII may be synthesized using processes known to one skilled in the art and are also disclosed in U.S. Pat. No. 3,261,859.

In one or more embodiments of the invention, a compound is provided, the compound comprising a residue of a calcium channel blocker covalently attached via a stable or degradable linkage to a water-soluble and non-peptidic oligomer, wherein the calcium channel blocker has a structure encompassed by the following formula:

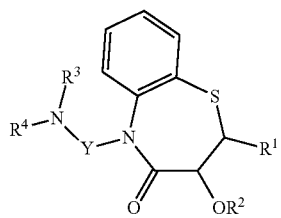

Formula VIII wherein (with respect to Formula VIII):

$R^1$ is a phenyl group optionally substituted with 1 to 3 substituents selected from the group consisting of lower alkyl groups, lower alkoxy groups and halogen atoms;

$R^2$ is a hydrogen atom or a lower alkanoyl group;

$R^3$ and $R^4$ are each independently a lower alkyl group;

X is hydrogen or a halogen atom; and

Y is an alkylene group of 2 or 3 carbon atoms.

Pharmaceutically acceptable salts of the compounds are also contemplated. Optionally, the compound can be combined with a pharmaceutically acceptable excipient to form a composition. CCBs encompassed by Formula VIII may be synthesized using the processes known to one skilled in the art and are also disclosed in U.S. Pat. Nos. 3,562,257 and 4,552,695.

In one or more embodiments of the invention, a compound is provided, the compound comprising a residue of a calcium channel blocker covalently attached via a stable or degradable linkage to a water-soluble and non-peptidic oligomer, wherein the calcium channel blocker has a structure encompassed by the following formula:

Formula IX

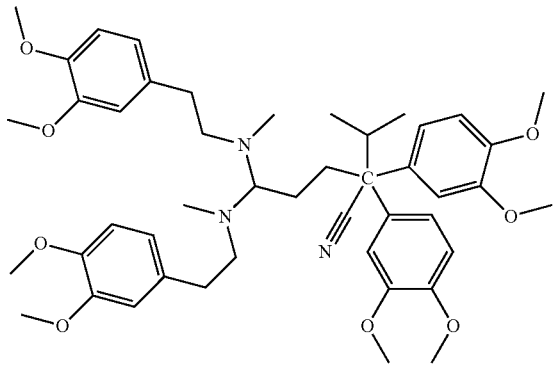

Pharmaceutically acceptable salts of the compounds are also contemplated. Optionally, the compound can be combined with a pharmaceutically acceptable excipient to form a composition. The CCB of Formula LX may be synthesized using processes known to one skilled in the art and are also disclosed in U.S. Pat. No. 3,261,859.

In one or more embodiments of the invention, a compound is provided, the compound comprising a residue of a calcium channel blocker covalently attached via a stable or degradable linkage to a water-soluble and non-peptidic oligomer, wherein the calcium channel blocker has a structure encompassed by the following formula:

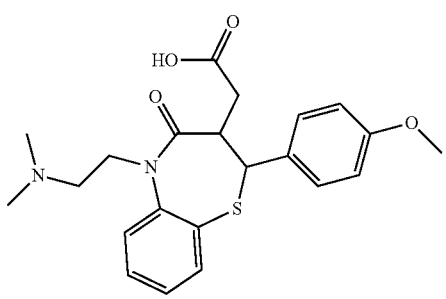

Pharmaceutically acceptable salts of the compounds are also contemplated. Optionally, the compound can be combined with a pharmaceutically acceptable excipient to form a composition.

In one or more embodiments of the invention, a compound is provided, the compound comprising a residue of a calcium channel blocker covalently attached via a stable or degradable linkage to a water-soluble and non-peptidic oligomer, wherein the calcium channel blocker has a structure encompassed by the following formula:

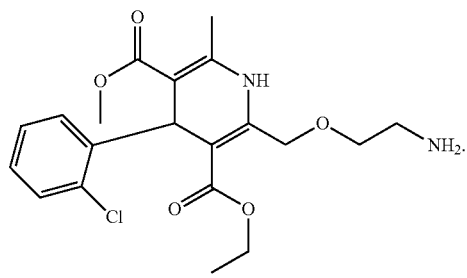 [SMILES: CCOC(=O)C1=C(COCCN)NC(C)=C(C(=O)OC)C1c1ccccc1Cl]

Pharmaceutically acceptable salts of the compounds are also contemplated. Optionally, the compound can be combined with a pharmaceutically acceptable excipient to form a composition.

In one or more embodiments of the invention, a compound is provided, the compound comprising a residue of a calcium channel blocker covalently attached via a stable or degradable linkage to a water-soluble and non-peptidic oligomer, wherein the calcium channel blocker has a structure encompassed by the following formula:

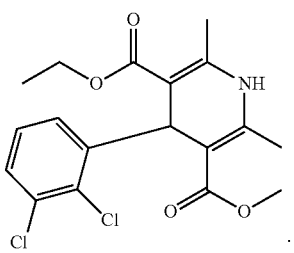 [SMILES: CCOC(=O)C1=C(C)NC(C)=C(C(=O)OC)C1c1cccc(Cl)c1Cl]

Pharmaceutically acceptable salts of the compounds are also contemplated. Optionally, the compound can be combined with a pharmaceutically acceptable excipient to form a composition.

In one or more embodiments of the invention, a compound is provided, the compound comprising a residue of a calcium channel blocker covalently attached via a stable or degradable linkage to a water-soluble and non-peptidic oligomer, wherein the calcium channel blocker has a structure encompassed by the following formula:

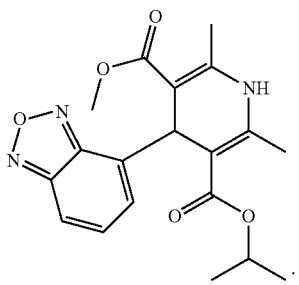 [SMILES: COC(=O)C1=C(C)NC(C)=C(C(=O)OC(C)C)C1c1cccc2nonc12]

Pharmaceutically acceptable salts of the compounds are also contemplated. Optionally, the compound can be combined with a pharmaceutically acceptable excipient to form a composition.

In one or more embodiments of the invention, a compound is provided, the compound comprising a residue of a calcium channel blocker covalently attached via a stable or degradable linkage to a water-soluble and non-peptidic oligomer, wherein the calcium channel blocker has a structure encompassed by the following formula:

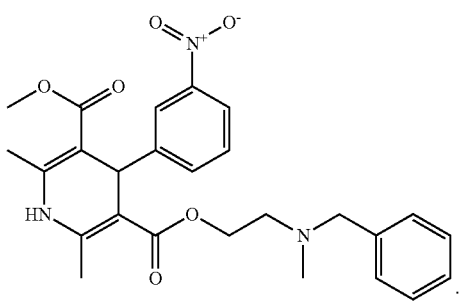 [SMILES: COC(=O)C1=C(C)NC(C)=C(C(=O)OCCN(C)Cc2ccccc2)C1c1cccc([N+](=O)[O-])c1]

Pharmaceutically acceptable salts of the compounds are also contemplated. Optionally, the compound can be combined with a pharmaceutically acceptable excipient to form a composition.

In one or more embodiments of the invention, a compound is provided, the compound comprising a residue of a calcium channel blocker covalently attached via a stable or degradable linkage to a water-soluble and non-peptidic oligomer, wherein the calcium channel blocker has a structure encompassed by the following formula:

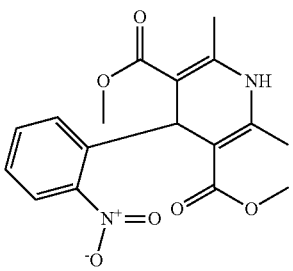

Pharmaceutically acceptable salts of the compounds are also contemplated. Optionally, the compound can be combined with a pharmaceutically acceptable excipient to form a composition.

In one or more embodiments of the invention, a compound is provided, the compound comprising a residue of a calcium channel blocker covalently attached via a stable or degradable linkage to a water-soluble and non-peptidic oligomer, wherein the calcium channel blocker has a structure encompassed by the following formula:

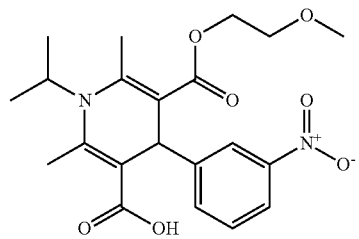 [SMILES: COCCOC(=O)C1=C(C)N(C(C)C)C(C)=C(C(=O)O)C1c1cccc([N+](=O)[O-])c1]

Pharmaceutically acceptable salts of the compounds are also contemplated. Optionally, the compound can be combined with a pharmaceutically acceptable excipient to form a composition.

In one or more embodiments of the invention, a compound is provided, the compound comprising a residue of a calcium channel blocker covalently attached via a stable or degradable linkage to a water-soluble and non-peptidic oligomer, wherein the calcium channel blocker has a structure encompassed by the following formula:

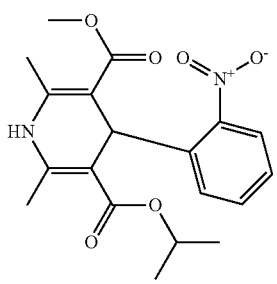

Pharmaceutically acceptable salts of the compounds are also contemplated. Optionally, the compound can be combined with a pharmaceutically acceptable excipient to form a composition.

In one or more embodiments of the invention, a compound is provided, the compound comprising a residue of a calcium channel blocker covalently attached via a stable or degradable linkage to a water-soluble and non-peptidic oligomer, wherein the calcium channel blocker has a structure encompassed by the following formula:

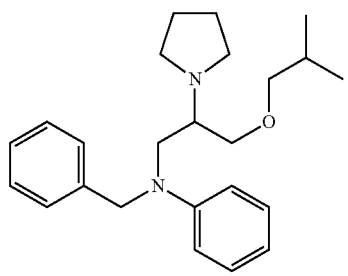

Pharmaceutically acceptable salts of the compounds are also contemplated. Optionally, the compound can be combined with a pharmaceutically acceptable excipient to form a composition. This CCB may be synthesized using the processes known to one skilled in the art and is also disclosed in U.S. Pat. No. 3,962,238 and RE 30,577.

Examples of calcium channel blockers include, but are not limited to, amlodipine, bepridil, diltiazem, felodipine, isradipine, nicardipine, nifedipine, nimodipine, nisoldipine and verapamil.

It is believed that an advantage of the conjugates of the present invention is their ability to retain some degree of calcium channel blocker activity while also exhibiting a decrease in metabolism. Although not wishing to be bound by theory, it is believed that the oligomer-containing conjugates described herein, in contrast to the unconjugated "original" calcium channel blocker, are not metabolized as readily because the oligomer serves to reduce the overall affinity of the compound to substrates that may metabolize calcium channel blockers. In addition (and again, not wishing to be bound by theory), the extra size introduced by the oligomer, in contrast to the unconjugated "original" calcium channel blocker, reduces the ability of the compound to cross the blood-brain barrier. Even should the linkage between the residue of the calcium channel blocker and the oligomer be degradable, the compound still offers advantages (such as avoiding first-pass metabolism upon initial absorption).

Use of discrete oligomers (e.g., from a monodisperse or bimodal composition of oligomers, in contrast to relatively impure compositions) to form conjugates may advantageously alter certain properties associated with the corresponding small molecule drug. For instance, a conjugate of the invention, when administered by any of a number of suitable administration routes, such as parenteral, oral, transdermal, buccal, pulmonary, or nasal, exhibits reduced penetration across the blood-brain barrier. It is preferred that the conjugates exhibit slowed, minimal or effectively no crossing of the blood-brain barrier, while still crossing the gastrointestinal (GI) walls and into the systemic circulation if oral delivery is intended. Moreover, the conjugates of the invention maintain a degree of bioactivity as well as bioavailability in their conjugated form.

With respect to the blood-brain barrier ("BBB"), this barrier restricts the transport of drugs from the blood to the brain. This barrier consists of a continuous layer of unique endothelial cells joined by tight junctions. The cerebral capillaries, which comprise more than 95% of the total surface area of the BBB, represent the principal route for the entry of solutes and drugs into the central nervous system.

For compounds whose degree of blood-brain barrier crossing ability is not known, the ability may be determined using a suitable animal model such as an in situ rat brain perfusion ("RBP") model as described herein. Briefly, the RBP technique involves cannulation of the carotid artery followed by perfusion with a compound solution under controlled conditions, followed by a wash out phase to remove compound remaining in the vascular space. (Such analyses may be conducted, for example, by contract research organizations such as Absorption Systems, Exton, Pa.). More specifically, in the RBP model, a cannula is placed in the left carotid artery and the side branches are tied off. A physiologic buffer containing the compound (5 micromolar) is perfused at a flow rate of 10 mL/min in a single pass perfusion experiment. After 30 seconds, the perfusion is stopped and the brain vascular contents are washed out with compound-free buffer for an additional 30 seconds. The brain tissue is then removed and analyzed for compound concentrations via liquid chromatograph with tandem mass spectrometry detection (LC/MS/MS). Alternatively, blood-brain barrier permeability can be estimated based upon a calculation of the compound's molecular polar surface area ("PSA"), which is defined as the sum of surface contributions of polar atoms (usually oxygens, nitrogens and attached hydrogens) in a molecule. The PSA has been shown to correlate with compound transport properties such as blood-brain barrier transport. Methods for determining a compound's PSA can be found, e.g., in, Ertl, P., et al., *J. Med. Chem.* 2000, 43, 3714-3717; and Kelder, J., et al., *Pharm. Res.* 1999, 16, 1514-1519.

With respect to the blood-brain barrier, the water-soluble oligomer-small molecule drug conjugate exhibits a blood-brain barrier crossing rate that is reduced as compared to the crossing rate of the small molecule drug not attached to the water-soluble oligomer. Exemplary reductions in blood-brain barrier crossing rates for the conjugates described herein include reductions of: at least about 5%; at least about 10%; at least about 25%; at least about 30%; at least about 40%; at least about 50%; at least about 60%; at least about 70%; at least about 80%; or at least about 90%, when compared to the blood-brain barrier crossing rate of the small molecule drug not attached to the water-soluble oligomer. A preferred reduction in the blood-brain barrier crossing rate for a conjugate is at least about 20%.

As indicated above, the compounds of the invention include a residue of a calcium channel blocker. Assays for determining whether a given compound may block calcium channel stimuli are described infra.

Exemplary calcium channel blockers have the following formula:

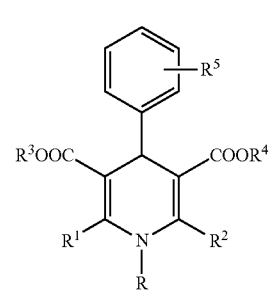

Formula I wherein (with respect to this Formula I):

R is hydrogen or lower alkyl;

$R^1$ and $R^2$ are each independently selected from the group consisting of hydrogen, substituted lower alkyl, unsubstituted lower alkyl, and —YOYNR$^6$R$^7$, where each Y is independently lower alkylene and $R^6$ and $R^7$ are each independently selected from group consisting of hydrogen, unsubstituted lower alkyl, substituted lower alkyl, cycloalkyl, aryl and alkylaryl;

$R^3$ and $R^4$ are each independently selected from the group consisting of hydrogen, unsubstituted lower alkyl, substituted lower alkyl, and —YNR$^6$R$^7$, where Y is lower alkylene and $R^6$ and $R^7$ are each independently selected from group consisting of hydrogen, unsubstituted lower alkyl, substituted lower alkyl, cycloalkyl, aryl and alkylaryl; and each $R^5$ is independently selected from group consisting of hydrogen, unsubstituted lower alkyl, substituted lower alkyl, chloro, fluoro and nitro. Pharmaceutically acceptable salts of the compounds are also contemplated. Optionally, the compound can be combined with a pharmaceutically acceptable excipient to form a composition.

In one embodiment, R is hydrogen. In another embodiment, R is methylethyl. In another embodiment, R is methylpropyl.

In one embodiment $R^1$ is methyl. In another embodiment $R^1$ is $CH_2OCH_2CH_2NH_2$.

In one embodiment $R^2$ is methyl. In another embodiment $R^2$ is $CH_2OCH_2CH_2NH_2$.

In one embodiment $R^3$ is hydrogen. In another embodiment $R^3$ is methyl. In another embodiment $R^3$ is ethyl. In another embodiment $R^3$ is methylethyl. In another embodiment $R^3$ is methoxyethyl. In another embodiment $R^3$ is 2-(benzyl-methyl-amino)ethyl.

In one embodiment $R^4$ is hydrogen. In another embodiment $R^4$ is methyl. In another embodiment $R^4$ is ethyl. In another embodiment $R^4$ is methylethyl. In another embodiment $R^4$ is methoxyethyl. In another embodiment $R^4$ is 2-(benzyl-methyl-amino)ethyl.

In one embodiment $R^5$ is hydrogen. In another embodiment $R^5$ is chloro. In another embodiment one $R^5$ is 2-chloro and another $R^5$ is 3-chloro. In another embodiment $R^5$ is nitro.

In some instances, calcium channel blockers may be obtained from commercial sources. In addition, calcium channel blockers may be obtained through chemical synthesis. Synthetic approaches for preparing calcium channel blockers is described in the literature and in, for example, U.S. Pat. Nos. 4,466,972, 4,552,695, 3,562,257, RE30,577, 3,261,859, 4,406,906, 3,985,758, 3,485,847, 4,264,611, and 4,572,909.

Each of these (and other) calcium channel blockers can be covalently attached (either directly or through one or more atoms) to a water-soluble and non-peptidic oligomer.

The calcium channel blockers used in the conjugates are small molecule drugs, that is to say, pharmacologically active compounds having a molecular weight of less than about 1000 Daltons. Small molecule drugs, for the purpose of the invention, include oligopeptides, oligonucleotides, and other biomolecules having a molecular weight of less than about 1000 Daltons. Also encompassed in the term "small molecule drug" is any fragment of a peptide, protein or antibody, including native sequences and variants falling within the molecular weight range stated above. In one or more embodiments, however, it is preferred that the small molecule drug satisfies one or more of the following: not an oligopeptide; not an oligonucleotide; not an antibody; and not a fragment of any of the foregoing.

Exemplary molecular weights of small molecule drugs include molecular weights of: less than about 950; less than about 900; less than about 850; less than about 800; less than about 750; less than about 700; less than about 650; less than about 600; less than about 550; less than about 500; less than about 450; less than about 400; less than about 350; and less than about 300.

The small molecule drug used in the invention, if chiral, may be obtained from a racemic mixture, or an optically active form, for example, a single optically active enantiomer, or any combination or ratio of enantiomers. In addition, the small molecule drug may possess one or more geometric isomers. With respect to geometric isomers, a composition may a mixture of two or more geometric isomers. A small molecule drug for use in the present invention may be in its customary active form or may possess some degree of modification. For example, a small molecule drug may have a targeting agent, tag, or transporter attached thereto, prior to or after covalent attachment of an oligomer. Alternatively, the small molecule drug may possess a lipophilic moiety attached thereto, such as a phospholipid (e.g., distearoylphosphatidylethanolamine or "DSPE," dipalmitoylphosphatidylethanolamine or "DPPE," and so forth) or a small fatty acid. In some instances, however, it is preferred that the small molecule drug moiety does not include attachment to a lipophilic moiety.

The calcium channel blocker for coupling to a water-soluble and non-peptidic oligomer possesses a free hydroxyl, carboxyl, thio, amino group, or the like (i.e., "handle") suitable for covalent attachment to the oligomer. In addition, the calcium channel blocker may be modified by introduction of a reactive group, preferably by conversion of one of its existing functional groups to a functional group suitable for formation of a stable covalent linkage between the oligomer and the drug. Both approaches are illustrated in the Experimental section.

The water-soluble and non-peptidic oligomer comprises one or more monomers serially attached to form a chain of monomers. The oligomer may be formed from a single monomer type (i.e., is homo-oligomeric) or two or three monomer types (i.e., is co-oligomeric). Preferably, each oligomer is a co-oligomer of two monomers or, more preferably, is a homo-oligomer.

Accordingly, each oligomer is composed of up to three different monomer types selected from the group consisting of: alkylene oxide, such as ethylene oxide or propylene oxide; olefinic alcohol, such as vinyl alcohol, 1-propenol or 2-propenol; vinyl pyrrolidone; hydroxyalkyl methacrylamide or hydroxyalkyl methacrylate, where alkyl is preferably methyl; α-hydroxy acid, such as lactic acid or glycolic acid; phosphazene, oxazoline, amino acids, carbohydrates such as monosaccharides, saccharide or mannitol; and N-acryloylmorpholine. Preferred monomer types include alkylene oxide, olefinic alcohol, hydroxyalkyl methacrylamide or methacrylate, N-acryloylmorpholine, and α-hydroxy acid. Preferably, each oligomer is, independently, a co-oligomer of two monomer types selected from this group, or, more preferably, is a homo-oligomer of one monomer type selected from this group.

The two monomer types in a co-oligomer may be of the same monomer type, for example, two alkylene oxides, such as ethylene oxide and propylene oxide. Preferably, the oligomer is a homo-oligomer of ethylene oxide. Usually, although not necessarily, the terminus (or termini) of the oligomer that is not covalently attached to a small molecule is capped to render it unreactive. Alternatively, the terminus may include a reactive group. When the terminus is a reactive group, the reactive group is either selected such that it is unreactive under the conditions of formation of the final oligomer or during covalent attachment of the oligomer to a small molecule drug, or it is protected as necessary. One common end-functional group is hydroxyl or —OH, particularly for oligoethylene oxides.

The water-soluble and non-peptidic oligomer (e.g., "POLY" in various structures provided herein) may have any of a number of different geometries. For example, the water-soluble and non-peptidic oligomer may be linear, branched, or forked. The water-soluble and non-peptidic oligomer is linear or is branched, for example, having one branch point. Although much of the discussion herein is focused upon poly(ethylene oxide) as an illustrative oligomer, the discussion and structures presented herein can be readily extended to encompass any of the water-soluble and non-peptidic oligomers described above.

The molecular weight of the water-soluble and non-peptidic oligomer, excluding the linker portion, is generally relatively low. Exemplary values of the molecular weight of the water-soluble polymer include: below about 1500; below about 1450; below about 1400; below about 1350; below about 1300; below about 1250; below about 1200; below about 1150; below about 1100; below about 1050; below about 1000; below about 950; below about 900; below about 850; below about 800; below about 750; below about 700; below about 650; below about 600; below about 550; below about 500; below about 450; below about 400; below about 350; below about 300; below about 250; below about 200; and below about 100 Daltons.

Exemplary ranges of molecular weights of the water-soluble and non-peptidic oligomer (excluding the linker) include: from about 100 to about 1400 Daltons; from about 100 to about 1200 Daltons; from about 100 to about 800 Daltons; from about 100 to about 500 Daltons; from about 100 to about 400 Daltons; from about 200 to about 500 Daltons; from about 200 to about 400 Daltons; from about 75 to 1000 Daltons; and from about 75 to about 750 Daltons.

Preferably, the number of monomers in the water-soluble and non-peptidic oligomer falls within one or more of the following ranges: between about 1 and about 30 (inclusive); between about 1 and about 25; between about 1 and about 20; between about 1 and about 15; between about 1 and about 12; between about 1 and about 10. In certain instances, the number of monomers in series in the oligomer (and the corresponding conjugate) is one of 1, 2, 3, 4, 5, 6, 7, or 8. In additional embodiments, the oligomer (and the corresponding conjugate) contains 9, 10, 11, 12, 13, 14, 15, 16, 17, 18, 19, or 20 monomers in series. In yet further embodiments, the oligomer (and the corresponding conjugate) possesses 21, 22, 23, 24, 25, 26, 27, 28, 29 or 30 monomers in series. Thus, for example, when the water-soluble and non-peptidic polymer includes $CH_3$—$(OCH_2CH_2)_n$—, "n" is an integer that may be 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30, and may fall within one or more of the following ranges: between about 1 and about 25; between about 1 and about 20; between about 1 and about 15; between about 1 and about 12; between about 1 and about 10.

When the water-soluble and non-peptidic oligomer has 1, 2, 3, 4, 5, 6, 7, 8, 9, or 10 monomers, these values correspond to a methoxy end-capped oligo(ethylene oxide) having a molecular weights of about 75, 119, 163, 207, 251, 295, 339, 383, 427, and 471 Daltons, respectively. When the oligomer has 11, 12, 13, 14, or 15 monomers, these values correspond to methoxy end-capped oligo(ethylene oxide) having molecular weights corresponding to about 515, 559, 603, 647, and 691 Daltons, respectively.

When the water-soluble and non-peptidic oligomer is attached to the calcium channel blocker (in contrast to the step-wise addition of one or more monomers to effectively "grow" the oligomer onto the calcium channel blocker), it is preferred that the composition containing an activated form of the water-soluble and non-peptidic oligomer be monodispersed. In those instances, however, where a bimodal composition is employed, the composition will possess a bimodal distribution centering around any two of the above numbers of monomers. Ideally, the polydispersity index of each peak in the bimodal distribution, Mw/Mn, is 1.01 or less, and even more preferably, is 1.001 or less, and even more preferably is 1.0005 or less. More preferably, each peak possesses a MW/Mn value of 1.0000. For instance, a bimodal oligomer may have any one of the following exemplary combinations of monomer subunits: 1-2, 1-3, 1-4, 1-5, 1-6, 1-7, 1-8, 1-9, 1-10, and so forth; 2-3, 2-4, 2-5, 2-6, 2-7, 2-8, 2-9, 2-10, and so forth; 3-4, 3-5, 3-6, 3-7, 3-8, 3-9, 3-10, and so forth; 4-5, 4-6, 4-7, 4-8, 4-9, 4-10, and so forth; 5-6, 5-7, 5-8, 5-9, 5-10, and so forth; 6-7, 6-8, 6-9, 6-10, and so forth; 7-8, 7-9, 7-10, and so forth; and 8-9, 8-10, and so forth.

In some instances, the composition containing an activated form of the water-soluble and non-peptidic oligomer will be trimodal or even tetramodal, possessing a range of monomers units as previously described. Oligomer compositions possessing a well-defined mixture of oligomers (i.e., being bimodal, trimodal, tetramodal, and so forth) can be prepared by mixing purified monodisperse oligomers to obtain a desired profile of oligomers (a mixture of two oligomers differing only in the number of monomers is bimodal; a mixture of three oligomers differing only in the number of monomers is trimodal; a mixture of four oligomers differing only in the number of monomers is tetramodal), or alternatively, can be obtained from column chromatography of a polydisperse oligomer by recovering the "center cut", to obtain a mixture of oligomers in a desired and defined molecular weight range.

It is preferred that the water-soluble and non-peptidic oligomer is obtained from a composition that is preferably unimolecular or monodisperse. That is, the oligomers in the composition possess the same discrete molecular weight value rather than a distribution of molecular weights. Some monodisperse oligomers may be purchased or prepared from commercial sources (e.g., Sigma-Aldrich, St. Louis, Mo.), or alternatively, may be chemically synthesized. Water-soluble and non-peptidic oligomers may be prepared as described in Chen Y., Baker, G. L., J. Org. Chem., 6870-6873 (1999), WO 02/098949, and U.S. Patent Application Publication 2005/0136031.

When present, the linker or linkage (through which the water-soluble and non-peptidic polymer is attached to the calcium channel blocker) may be a single atom, such as an oxygen or a sulfur, two atoms, or a number of atoms. A linker may be linear in nature. The linkage, "X" is hydrolytically stable, and is preferably also enzymatically stable. Preferably, the linkage "X" is one having a chain length of less than about 12 atoms, and preferably less than about 10 atoms, and even more preferably less than about 8 atoms and even more preferably less than about 5 atoms, whereby length is meant the number of atoms in a single chain, not counting substituents. For instance, a urea linkage such as this, $R_{oligomer}$—NH—(C=O)—NH—$R'_{drug}$, is considered to have a chain length of 3 atoms (—NH—C(O)—NH—). In selected embodiments, the linkage does not comprise further spacer groups.

In some instances, the linker "X" comprises an ether, amide, urethane, amine, thioether, urea, or a carbon-carbon bond. Functional groups such as those discussed below, are used for forming the linkages. The linkage may less preferably also comprise (or be adjacent to or flanked by) spacer groups, as described further below. Spacers are useful in instances where the bioactivity of the conjugate is significantly reduced due to the positioning of the oligomer on the parent drug.

More specifically, in selected embodiments, a linker of the invention, X, may be any of the following: "-" (i.e., a covalent bond, that may be stable or degradable, between the residue of the small molecule calcium channel blocker and the water-soluble and non-peptidic oligomer), —O—, —NH—, —S—, —C(O)—, —C(O)O—, —OC(O)—, —CH$_2$—C(O)O—, —CH$_2$—OC(O)—, —C(O)O—CH$_2$—, —OC(O)—CH$_2$—, —C(O)—NH—, —NH—C(O)—NH—, —O—C(O)—NH, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—CH$_2$—C(O)—NH—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$, —CH$_2$—CH$_2$—NH—C(O)—CH$_2$—CH$_2$, —C(O)—NH—CH$_2$—, —C(O)—NH—CH$_2$—CH$_2$—, —O—C(O)—NH—CH$_2$—, —O—C(O)—NH—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—C(O)—CH$_2$—CH$_2$—, —CH$_2$—C(O)—NH—CH$_2$—CH$_2$—NH—, —CH$_2$—CH$_2$—C(O)—NH—CH$_2$—CH$_2$—NH—C(O)—, —CH$_2$—CH$_2$—C(O)—NH—CH$_2$—CH$_2$—NH—C(O)—CH$_2$—, bivalent cycloalkyl group, —N(R)—, R is selected from the group consisting of hydrogen, alkyl, substituted alkyl, alkenyl, substituted alkenyl, alkynyl, substituted alkynyl, aryl and substituted aryl.

For purposes of the present invention, however, a series of atoms is not considered as a linkage when the series of atoms is immediately adjacent to an oligomer segment, and the series of atoms is but another monomer such that the proposed linkage would represent a mere extension of the oligomer chain.

The linkage "X" between the water-soluble and non-peptidic oligomer and the small molecule is formed by reaction of a functional group on a terminus of the oligomer (or one or more monomers when it is desired to "grow" the oligomer onto the calcium channel blocker) with a corresponding functional group within the calcium channel blocker. Illustrative reactions are described briefly below. For example, an amino group on an oligomer may be reacted with a carboxylic acid or an activated carboxylic acid derivative on the small molecule, or vice versa, to produce an amide linkage. Alternatively, reaction of an amine on an oligomer with an activated carbonate (e.g. succinimidyl or benzotriazyl carbonate) on the drug, or vice versa, forms a carbamate linkage. Reaction of an amine on an oligomer with an isocyanate (R—N=C=O) on a drug, or vice versa, forms a urea linkage (R—NH—(C=O)—NH—R'). Further, reaction of an alcohol (alkoxide) group on an oligomer with an alkyl halide, or halide group within a drug, or vice versa, forms an ether linkage. In yet another coupling approach, a small molecule having an aldehyde function is coupled to an oligomer amino group by reductive amination, resulting in formation of a secondary amine linkage between the oligomer and the small molecule.

A particularly preferred water-soluble and non-peptidic oligomer is an oligomer bearing an aldehyde functional group. In this regard, the oligomer may have the following structure: CH$_3$O—(CH$_2$—CH$_2$—O)$_n$—(CH$_2$)$_p$—C(O)H, wherein (n) is one of 1, 2, 3, 4, 5, 6, 7, 8, 9 and 10 and (p) is one of 1, 2, 3, 4, 5, 6 and 7. Preferred (n) values include 3, 5 and 7 and preferred (p) values 2, 3 and 4.

The terminus of the water-soluble and non-peptidic oligomer not bearing a functional group may be capped to render it unreactive. When the oligomer does includes a further functional group at a terminus other than that intended for formation of a conjugate, that group is either selected such that it is unreactive under the conditions of formation of the linkage "X," or it is protected during the formation of the linkage "X."

As stated above, the water-soluble and non-peptidic oligomer includes at least one functional group prior to conjugation. The functional group comprises an electrophilic or nucleophilic group for covalent attachment to a small molecule, depending upon the reactive group contained within or introduced into the small molecule. Examples of nucleophilic groups that may be present in either the oligomer or the small molecule include hydroxyl, amine, hydrazine (—NHNH$_2$), hydrazide (—C(O)NHNH$_2$), and thiol. Preferred nucleophiles include amine, hydrazine, hydrazide, and thiol, particularly amine. Small molecule drugs for covalent attachment to an oligomer may possess a free hydroxyl, amino, thio, aldehyde, ketone, or carboxyl group.

Examples of electrophilic functional groups that may be present in either the oligomer or the small molecule include carboxylic acid, carboxylic ester, particularly imide esters, orthoester, carbonate, isocyanate, isothiocyanate, aldehyde, ketone, thione, alkenyl, acrylate, methacrylate, acrylamide, sulfone, maleimide, disulfide, iodo, epoxy, sulfonate, thiosulfonate, silane, alkoxysilane, and halosilane. More specific examples of these groups include succinimidyl ester or carbonate, imidazoyl ester or carbonate, benzotriazole ester or carbonate, vinyl sulfone, chloroethylsulfone, vinylpyridine, pyridyl disulfide, iodoacetamide, glyoxal, dione, mesylate, tosylate, and tresylate (2,2,2-trifluoroethanesulfonate).

Also included are sulfur analogs of several of these groups, such as thione, thione hydrate, thioketal, is 2-thiazolidine thione, etc., as well as hydrates or protected derivatives of any of the above moieties (e.g. aldehyde hydrate, hemiacetal, acetal, ketone hydrate, hemiketal, ketal, thioketal, thioacetal).

An "activated derivative" of a carboxylic acid refers to a carboxylic acid derivative which reacts readily with nucleophiles, generally much more readily than the underivatized carboxylic acid. Activated carboxylic acids include, for example, acid halides (such as acid chlorides), anhydrides, carbonates, and esters. Such esters include imide esters, of the general form —(CO)O—N[(CO)—]$_2$; for example, N-hydroxysuccinimidyl (NHS) esters or N-hydroxyphthalimidyl esters. Also preferred are imidazolyl esters and benzotriazole esters. Particularly preferred are activated propionic acid or butanoic acid esters, as described in co-owned U.S. Pat. No. 5,672,662. These include groups of the form —(CH$_2$)$_{2-3}$C (=O)O-Q, where Q is preferably selected from N-succinimide, N-sulfosuccinimide, N-phthalimide, N-glutarimide, N-tetrahydrophthalimide, N-norbornene-2,3-dicarboximide, benzotriazole, 7-azabenzotriazole, and imidazole.

Other preferred electrophilic groups include succinimidyl carbonate, maleimide, benzotriazole carbonate, glycidyl ether, imidazoyl carbonate, p-nitrophenyl carbonate, acrylate, tresylate, aldehyde, and orthopyridyl disulfide.

These electrophilic groups are subject to reaction with nucleophiles, e.g. hydroxy, thio, or amino groups, to produce various bond types. Preferred for the present invention are reactions which favor formation of a hydrolytically stable linkage. For example, carboxylic acids and activated derivatives thereof, which include orthoesters, succinimidyl esters, imidazolyl esters, and benzotriazole esters, react with the above types of nucleophiles to form esters, thioesters, and amides, respectively, of which amides are the more hydrolytically stable. As mentioned above, more preferred are conjugates having a hydrolytically stable linkage between the oligomer and the drug. Carbonates, including succinimidyl, imidazolyl, and benzotriazole carbonates, react with amino groups to form carbamates. Isocyanates (R—N=C=O) react with hydroxyl or amino groups to form, respectively, carbamate (RNH—C(O)—OR') or urea (RNH—C(O)—NHR') linkages. Aldehydes, ketones, glyoxals, diones and their hydrates or alcohol adducts (i.e. aldehyde hydrate, hemiacetal, acetal, ketone hydrate, hemiketal, and ketal) are preferably reacted with amines, followed by reduction of the resulting imine, if desired, to provide an amine linkage (reductive amination).

Several of the electrophilic functional groups include electrophilic double bonds to which nucleophilic groups, such as thiols, may be added, to form, for example, thioether bonds. These groups include maleimides, vinyl sulfones, vinyl pyridine, acrylates, methacrylates, and acrylamides. Other groups comprise leaving groups which may be displaced by a nucleophile; these include chloroethyl sulfone, pyridyl disulfides (which include a cleavable S—S bond), iodoacetamide, mesylate, tosylate, thiosulfonate, and tresylate. Epoxides react by ring opening by a nucleophile, to form, for example, an ether or amine bond. Reactions involving complementary reactive groups such as those noted above on the oligomer and the small molecule are utilized to prepare the conjugates of the invention.

In some instances the calcium channel blocker may not have a functional group suited for conjugation. In this instance, it is possible to modify the "original" calcium channel blocker so that it does have a functional group suited for conjugation. For example, if the calcium channel blocker has an amide group, but an amine group is desired, it is possible to modify the amide group to an amine group by way of a Hofmann rearrangement, Curtius rearrangement (once the amide is converted to an azide) or Lossen rearrangement (once amide is concerted to hydroxamide followed by treatment with tolyene-2-sulfonyl chloride/base).

It is possible to prepare a conjugate of small molecule calcium channel blocker bearing a carboxyl group wherein the carboxyl group-bearing small molecule calcium channel blocker is coupled to an amino-terminated oligomeric ethylene glycol, to provide a conjugate having an amide group covalently linking the small molecule calcium channel blocker to the oligomer. This can be performed, for example, by combining the carboxyl group-bearing small molecule calcium channel blocker with the amino-terminated oligomeric ethylene glycol in the presence of a coupling reagent, (such as dicyclohexylcarbodiimide or "DCC") in an anhydrous organic solvent.

Further, it is possible to prepare a conjugate of a small molecule calcium channel blocker bearing a hydroxyl group wherein the hydroxyl group-bearing small molecule calcium channel blocker is coupled to an oligomeric ethylene glycol halide to result in an ether (—O—) linked small molecule conjugate. This can be performed, for example, by using sodium hydride to deprotonate the hydroxyl group followed by reaction with a halide-terminated oligomeric ethylene glycol.

In another example, it is possible to prepare a conjugate of a small molecule calcium channel blocker bearing a ketone group by first reducing the ketone group to form the corresponding hydroxyl group. Thereafter, the small molecule calcium channel blocker now bearing a hydroxyl group can be coupled as described herein.

In still another instance, it is possible to prepare a conjugate of a small molecule calcium channel blocker bearing an amine group. In one approach, the amine group-bearing small molecule calcium channel blocker and an aldehyde-bearing oligomer are dissolved in a suitable buffer after which a suitable reducing agent (e.g., NaCNBH$_3$) is added. Following reduction, the result is an amine linkage formed between the amine group of the amine group-containing small molecule calcium channel blocker and the carbonyl carbon of the aldehyde-bearing oligomer.

In another approach for preparing a conjugate of a small molecule calcium channel blocker bearing an amine group, a carboxylic acid-bearing oligomer and the amine group-bearing small molecule calcium channel blocker are combined, in the presence of a coupling reagent (e.g., DCC). The result is an amide linkage formed between the amine group of the amine group-containing small molecule calcium channel blocker and the carbonyl of the carboxylic acid-bearing oligomer.

Exemplary conjugates of calcium channel blockers include those encompassed by the following structure:

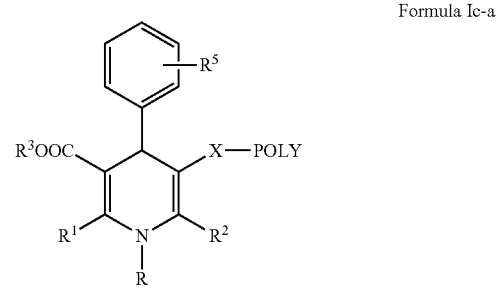

Formula Ic-a wherein (with respect to this Formula Ic-a):

R is hydrogen or lower alkyl;

$R^1$ and $R^2$ are each independently selected from the group consisting of hydrogen, substituted lower alkyl, unsubstituted lower alkyl, and —YOYNR$^6$R$^7$, where each Y is independently lower alkylene and R$^6$ and R$^7$ are each independently selected from group consisting of hydrogen, unsubstituted lower alkyl, substituted lower alkyl, cycloalkyl, aryl and alkylaryl;

$R^3$ is selected from the group consisting of hydrogen, unsubstituted lower alkyl, substituted lower alkyl, and —YNR$^6$R$^7$, where Y is lower alkylene and R$^6$ and R$^7$ are each independently selected from group consisting of hydrogen, unsubstituted lower alkyl, substituted lower alkyl, cycloalkyl, aryl and alkylaryl;

$R^5$ is independently selected from group consisting of hydrogen, unsubstituted lower alkyl, substituted lower alkyl, chloro, fluoro and nitro;

X is a spacer moiety; and

POLY is a water-soluble oligomer. Pharmaceutically acceptable salts of the compounds are also contemplated. Optionally, the compound can be combined with a pharmaceutically acceptable excipient to form a composition.

Additional exemplary conjugates of calcium channel blockers include those encompassed by the following structure:

Formula Ic-b

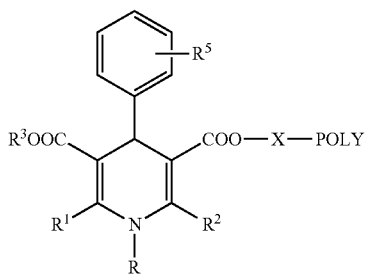

wherein (with respect to this Formula Ic-b):

R is hydrogen or lower alkyl;

$R^1$ and $R^2$ are each independently selected from the group consisting of hydrogen, substituted lower alkyl, unsubstituted lower alkyl, and —YOYNR$^6$R$^7$, where each Y is independently lower alkylene and $R^6$ and $R^7$ are each independently selected from group consisting of hydrogen, unsubstituted lower alkyl, substituted lower alkyl, cycloalkyl, aryl and alkylaryl;

$R^3$ is selected from the group consisting of hydrogen, unsubstituted lower alkyl, substituted lower alkyl, and —YNR$^6$R$^7$, where Y is lower alkylene and $R^6$ and $R^7$ are each independently selected from group consisting of hydrogen, unsubstituted lower alkyl, substituted lower alkyl, cycloalkyl, aryl and alkylaryl;

$R^5$ is independently selected from group consisting of hydrogen, unsubstituted lower alkyl, substituted lower alkyl, chloro, fluoro and nitro;

X is a spacer moiety; and

POLY is a water-soluble oligomer. Pharmaceutically acceptable salts of the compounds are also contemplated. Optionally, the compound can be combined with a pharmaceutically acceptable excipient to form a composition.

Still further exemplary conjugates of calcium channel blockers include those encompassed by the following structure:

Formula Ic-c

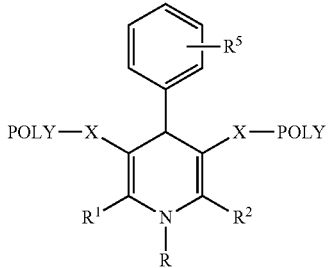

wherein (with respect to this Formula Ic-c):

R is hydrogen or lower alkyl;

$R^1$ and $R^2$ are each independently selected from the group consisting of hydrogen, substituted lower alkyl, unsubstituted lower alkyl, and —YOYNR$^6$R$^7$, where each Y is independently lower alkylene and $R^6$ and $R^7$ are each independently selected from group consisting of hydrogen, unsubstituted lower alkyl, substituted lower alkyl, cycloalkyl, aryl and alkylaryl;

$R^3$ is selected from the group consisting of hydrogen, unsubstituted lower alkyl, substituted lower alkyl, and —YNR$^6$R$^7$, where Y is lower alkylene and $R^6$ and $R^7$ are each independently selected from group consisting of hydrogen, unsubstituted lower alkyl, substituted lower alkyl, cycloalkyl, aryl and alkylaryl;

$R^5$ is independently selected from group consisting of hydrogen, unsubstituted lower alkyl, substituted lower alkyl, chloro, fluoro and nitro;

each X is independently a spacer moiety; and each POLY is independently a water-soluble oligomer. Pharmaceutically acceptable salts of the compounds are also contemplated. Optionally, the compound can be combined with a pharmaceutically acceptable excipient to form a composition.

Still further exemplary conjugates of calcium channel blockers include those encompassed by the following structure:

Formula Ic-d

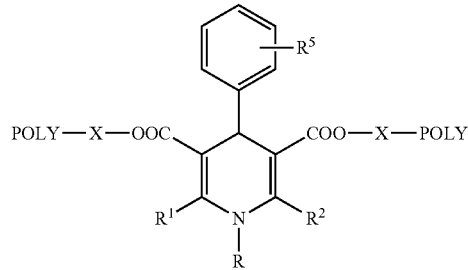

wherein (with respect to this Formula Ic-d):

R is hydrogen or lower alkyl;

$R^1$ and $R^2$ are each independently selected from the group consisting of hydrogen, substituted lower alkyl, unsubstituted lower alkyl, and —YOYNR$^6$R$^7$, where each Y is independently lower alkylene and $R^6$ and $R^7$ are each independently selected from group consisting of hydrogen, unsubstituted lower alkyl, substituted lower alkyl, cycloalkyl, aryl and alkylaryl;

$R^3$ is selected from the group consisting of hydrogen, unsubstituted lower alkyl, substituted lower alkyl, and —YNR$^6$R$^7$, where Y is lower alkylene and $R^6$ and $R^7$ are each independently selected from group consisting of hydrogen, unsubstituted lower alkyl, substituted lower alkyl, cycloalkyl, aryl and alkylaryl;

$R^5$ is independently selected from group consisting of hydrogen, unsubstituted lower alkyl, substituted lower alkyl, chloro, fluoro and nitro;

each X is independently a spacer moiety; and each POLY is independently a water-soluble oligomer. Pharmaceutically acceptable salts of the compounds are also contemplated. Optionally, the compound can be combined with a pharmaceutically acceptable excipient to form a composition.

Exemplary conjugates of calcium channel blockers include those encompassed by the following structure:

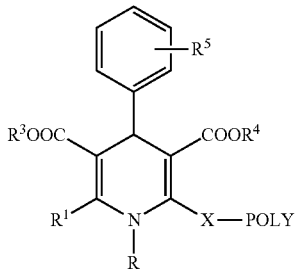

Formula Ic-e wherein (with respect to this Formula Ic-e):

R is hydrogen or lower alkyl;

$R^1$ is selected from the group consisting of hydrogen, substituted lower alkyl, unsubstituted lower alkyl and —YOYNR$^6$R$^7$, where each Y is independently lower alkylene and $R^6$ and $R^7$ are each independently selected from group consisting of hydrogen, unsubstituted lower alkyl, substituted lower alkyl, cycloalkyl, aryl and alkylaryl $R^3$ and $R^4$ are independently selected from the group consisting of hydrogen, unsubstituted lower alkyl, substituted lower alkyl, and —YNR$^6$R$^7$, where Y is lower alkylene and $R^6$ and $R^7$ are each independently selected from group consisting of hydrogen, unsubstituted lower alkyl, substituted lower alkyl, cycloalkyl, aryl and alkylaryl;

$R^5$ is independently selected from group consisting of hydrogen, unsubstituted lower alkyl, substituted lower alkyl, chloro, fluoro and nitro;

X is a spacer moiety; and

POLY is a water-soluble oligomer. Pharmaceutically acceptable salts of the compounds are also contemplated. Optionally, the compound can be combined with a pharmaceutically acceptable excipient to form a composition.

Exemplary conjugates of calcium channel blockers include those encompassed by the following structure:

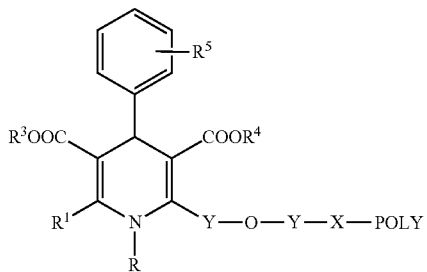

Formula Ic-f wherein (with respect to this Formula Ic-f):

R is hydrogen or lower alkyl;

$R^1$ is selected from the group consisting of hydrogen, substituted lower alkyl, unsubstituted lower alkyl and —YOYNR$^6$R$^7$, where each Y is independently lower alkylene and $R^6$ and $R^7$ are each independently selected from group consisting of hydrogen, unsubstituted lower alkyl, substituted lower alkyl, cycloalkyl, aryl and alkylaryl;

each Y is independently lower alkylene;

$R^3$ and $R^4$ are independently selected from the group consisting of hydrogen, unsubstituted lower alkyl, substituted lower alkyl, and —YNR$^6$R$^7$, where Y is lower alkylene and $R^6$ and $R^7$ are each independently selected from group consisting of hydrogen, unsubstituted lower alkyl, substituted lower alkyl, cycloalkyl, aryl and alkylaryl;

$R^5$ is independently selected from group consisting of hydrogen, unsubstituted lower alkyl, substituted lower alkyl, chloro, fluoro and nitro;

X is a spacer moiety; and

POLY is a water-soluble oligomer.

Pharmaceutically acceptable salts of the compounds are also contemplated. Optionally, the compound can be combined with a pharmaceutically acceptable excipient to form a composition.

Exemplary conjugates of calcium channel blockers include those encompassed by the following structure:

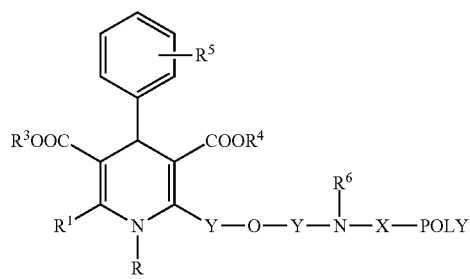

Formula Ic-g wherein (with respect to this Formula Ic-g):

R is hydrogen or lower alkyl;

$R^1$ is selected from the group consisting of hydrogen, substituted lower alkyl, unsubstituted lower alkyl and —YOYNR$^6$R$^7$, where each Y is independently lower alkylene and $R^6$ and $R^7$ are each independently selected from group consisting of hydrogen, unsubstituted lower alkyl, substituted lower alkyl, cycloalkyl, aryl and alkylaryl;

each Y is independently lower alkylene;

$R^3$ and $R^4$ are independently selected from the group consisting of hydrogen, unsubstituted lower alkyl, substituted lower alkyl, and —YNR$^6$R$^7$, where Y is lower alkylene and $R^6$ and $R^7$ are each independently selected from group consisting of hydrogen, unsubstituted lower alkyl, substituted lower alkyl, cycloalkyl, aryl and alkylaryl;

$R^5$ is independently selected from group consisting of hydrogen, unsubstituted lower alkyl, substituted lower alkyl, chloro, fluoro and nitro;

$R^6$ is selected from group consisting of hydrogen, unsubstituted lower alkyl, substituted lower alkyl, cycloalkyl, aryl and alkylaryl;

X is a spacer moiety; and

POLY is a water-soluble oligomer. Pharmaceutically acceptable salts of the compounds are also contemplated. Optionally, the compound can be combined with a pharmaceutically acceptable excipient to form a composition.

The conjugates of the invention can exhibit a reduced blood-brain barrier crossing rate. Moreover, the conjugates maintain at least about 5%, 10%, 20%, 30%, 40%, 50%, 60%, 70%, or more of the bioactivity of the unmodified parent small molecule drug.

The selection of an optimally sized oligomer can be determined as follows.

First, an oligomer (preferably obtained from a monodisperse or bimodal water soluble oligomer) is conjugated to the small molecule drug. Preferably, the drug is orally bioavailable, and on its own in unmodified form, exhibits a blood-brain barrier crossing rate. Next, the ability of the conjugate to cross the blood-brain barrier is determined using an appropriate model and compared to that of the unmodified parent drug. If the results are favorable, that is to say, if, for example, the rate of crossing is significantly reduced, then the bioactivity of conjugate is further evaluated. In one or more embodiments, the drug in conjugated form can be bioactive, and preferably, maintains a significant degree of bioactivity relative to the parent drug, i.e., greater than about 30% of the bioactivity of the parent drug, or even more preferably, greater than about 50% of the bioactivity of the parent drug.

Then, the above steps are repeated using oligomers of the same monomer type but having a different number of subunits.

For each conjugate whose ability to cross the blood-brain barrier is reduced in comparison to the non-conjugated small molecule drug, its oral bioavailability is then assessed. Based upon these results of sequential addition of increasing numbers of discrete monomers to a given small molecule at a given position or location within the small molecule, it is possible to determine the size of the oligomer effective in providing a conjugate having an optimal balance between reduction in biological membrane crossing, oral bioavailability, and bioactivity. The small size of the oligomers may make such screenings feasible, and may allow one to effectively tailor the properties of the resulting conjugate. By making small, incremental changes in oligomer size, and utilizing an experimental design approach, one can effectively identify a conjugate having a favorable balance of reduction in biological membrane crossing rate, bioactivity, and oral bioavailability. In some instances, attachment of an oligomer as described herein is effective to actually increase oral bioavailability of the drug.

For example, one of ordinary skill in the art, using routine experimentation, may determine a best suited molecular size and linkage for improving oral bioavailability by first preparing a series of oligomers with different weights and functional groups and then obtaining the necessary clearance profiles by administering the conjugates to a patient and taking periodic blood and/or urine sampling. Once a series of clearance profiles have been obtained for each tested conjugate, a suitable conjugate can be identified.

Animal models (rodents and dogs) may also be used to study oral drug transport. In addition, non-in vivo methods include rodent everted gut excised tissue and Caco-2 cell monolayer tissue-culture models. These models are useful in predicting oral drug bioavailability.

The ability of the compounds to inhibit the movement of calcium into the cell is shown by their effectiveness in reducing the response of isolated heart tissue to an increase in calcium ion concentration in vitro. The test is performed by mounting spirally cut strips of rat aorta with one end fixed and the other attached to a force transducer. The tissue is immersed in a bath of physiological saline solution containing potassium ions at a concentration of 45 millimolar and no calcium. Calcium chloride is added to the bath with a pipette to give a final calcium ion concentration of 2 millimolar. The change in tension caused by the resulting contraction of the tissue is noted. The bath is drained and replaced with fresh saline solution and, after 45 minutes, the test is repeated with the particular compound under test present in the saline solution. The concentration of compound required to reduce the response by 50% is recorded.

The antihypertensive activity of the compounds is also evaluated after oral administration by measuring the fall in blood pressure in spontaneously hypertensive rats or renally hypertensive dogs.

Alternately, the antihypertensive effect of the compounds may be tested in conscious, unrestrained spontaneously hypertensive rats (SHR) of the Okamoto strain. The animals may be prepared by prior implantation of indwelling catheters in the abdominal aorta via the femoral artery. Mean arterial blood pressure (MABP) and heart rate are continuously monitored. After a 2 hour control period the compound under study is administered by oral intubation at 2 hour intervals, suspended in METHOCEL solution (5 ml/kg bodyweight). The cumulated doses are 1, 5 and 25 µmoles/kg bodyweight. The antihypertensive response, i.e. the BP reduction to each dose, is expressed as a percentage of the initial control BP level and plotted against the dose on a logarithmic scale. The dose which would give 20 percent BP reduction is then determined by interpolation.

The specificity towards smooth muscle relaxation is examined as follows: The isolated portal vein preparation of Wistar rats is mounted in an organ bath together with a paced isolated papillary heart muscle preparation of the same animal. The integrated contractile activity of the portal vein smooth muscle and the peak force amplitude of the papillary, myocardial, preparation are recorded. The respective activities during a 30 min control period are set as 100 percent and the ensuing activities under the influence of an agent under study are expressed as a percentage thereof. The agent is administered at 10 min intervals and the potency for vasodilatation ($-\log ED_{50}$ of portal vein) and that of myocardial depression ($-\log ED_{50}$ of papillary muscle) are determined by interpolation from the concentration-effect relationships determined in each experiment. A "separation" value is determined for each compound by averaging the differences of the $-\log ED_{50}$ values for vasodilatation and myocardial depression, respectively, obtained in the experiments. This logarithmic separation value is transformed into numeric format.

The present invention also includes pharmaceutical preparations comprising a conjugate as provided herein in combination with a pharmaceutical excipient. Generally, the conjugate itself may be in a solid form (e.g., a precipitate), which may be combined with a suitable pharmaceutical excipient that may be in either solid or liquid form.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

The excipient may also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant may be present in the preparation as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant may be present as an excipient. Exemplary surfactants include: polysorbates, such as "TWEEN 20" and "TWEEN 80," and PLURONICs such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Acids or bases may be present as an excipient in the preparation. Nonlimiting examples of acids that may be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the conjugate in the composition may vary depending on a number of factors, but may optimally be a therapeutically effective dose when the composition is stored in a unit dose container. A therapeutically effective dose may be determined experimentally by repeated administration of increasing amounts of the conjugate in order to determine which amount produces a clinically desired endpoint.

The amount of any individual excipient in the composition may vary depending on the activity of the excipient and particular needs of the composition. The optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

The excipient may be present in the composition in an amount of about 1% to about 99% by weight, preferably from about 5%-98% by weight, more preferably from about 15-95% by weight of the excipient, with concentrations less than 30% by weight more preferred.

These foregoing pharmaceutical excipients along with other excipients are described in "Remington: The Science & Practice of Pharmacy", 19$^{th}$ ed., Williams & Williams, (1995), the "Physician's Desk Reference", 52$^{nd}$ ed., Medical Economics, Montvale, N.J. (1998), and Kibbe, A. H., Handbook of Pharmaceutical Excipients, 3$^{rd}$ Edition, American Pharmaceutical Association, Washington, D.C., 2000.

The pharmaceutical compositions may take any number of forms and the invention is not limited in this regard. Exemplary preparations are more preferably in a form suitable for oral administration such as a tablet, caplet, capsule, gel cap, troche, dispersion, suspension, solution, elixir, syrup, lozenge, transdermal patch, spray, suppository, and powder.

Oral dosage forms are preferred for those conjugates that are orally active, and include tablets, caplets, capsules, gel caps, suspensions, solutions, elixirs, and syrups, and may also comprise a plurality of granules, beads, powders or pellets that are optionally encapsulated. Such dosage forms are prepared using conventional methods known to those in the field of pharmaceutical formulation and described in the pertinent texts.

Tablets and caplets, for example, may be manufactured using standard tablet processing procedures and equipment. Direct compression and granulation techniques are preferred when preparing tablets or caplets containing the conjugates described herein. In addition to the conjugate, the tablets and caplets may generally contain inactive, pharmaceutically acceptable carrier materials such as binders, lubricants, disintegrants, fillers, stabilizers, surfactants, coloring agents, and the like. Binders are used to impart cohesive qualities to a tablet, and thus ensure that the tablet remains intact. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and VEEGUM. Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

Capsules are also preferred oral dosage forms, in which case the conjugate-containing composition may be encapsulated in the form of a liquid or gel (e.g., in the case of a gel cap) or solid (including particulates such as granules, beads, powders or pellets). Suitable capsules include hard and soft capsules, and are generally made of gelatin, starch, or a cellulosic material. Two-piece hard gelatin capsules are preferably sealed, such as with gelatin bands or the like.

Included are parenteral formulations in the substantially dry form (as a lyophilizate or precipitate, which may be in the form of a powder or cake), as well as formulations prepared for injection, which are liquid and requires the step of reconstituting the dry form of parenteral formulation. Examples of suitable diluents for reconstituting solid compositions prior to injection include bacteriostatic water for injection, dextrose 5% in water, phosphate-buffered saline, Ringer's solution, saline, sterile water, deionized water, and combinations thereof.

In some cases, compositions intended for parenteral administration may take the form of nonaqueous solutions, suspensions, or emulsions, each being sterile. Examples of nonaqueous solvents or vehicles are propylene glycol, polyethylene glycol, vegetable oils, such as olive oil and corn oil, gelatin, and injectable organic esters such as ethyl oleate.

The parenteral formulations described herein may also contain adjuvants such as preserving, wetting, emulsifying, and dispersing agents. The formulations are rendered sterile by incorporation of a sterilizing agent, filtration through a bacteria-retaining filter, irradiation, or heat.

The conjugate may also be administered through the skin using conventional transdermal patch or other transdermal delivery system, wherein the conjugate is contained within a laminated structure that serves as a drug delivery device to be affixed to the skin. In such a structure, the conjugate is contained in a layer, or "reservoir," underlying an upper backing layer. The laminated structure may contain a single or multiple reservoirs.

The conjugate may also be formulated into a suppository for rectal administration. With respect to suppositories, the conjugate is mixed with a suppository base material which is (e.g., an excipient that remains solid at room temperature but softens, melts or dissolves at body temperature) such as coca butter (theobroma oil), polyethylene glycols, glycerinated gelatin, fatty acids, and combinations thereof. Suppositories may be prepared by, for example, performing the following steps (not necessarily in the order presented): melting the suppository base material to form a melt; incorporating the conjugate (either before or after melting of the suppository base material); pouring the melt into a mold; cooling the melt (e.g., placing the melt-containing mold in a room temperature environment) to thereby form suppositories; and removing the suppositories from the mold.

The invention also provides a method for administering a conjugate as provided herein to a patient suffering from a condition that is responsive to treatment with the conjugate. The method comprises administering, generally orally, a therapeutically effective amount of the conjugate (preferably provided as part of a pharmaceutical preparation). Other modes of administration are also contemplated, such as pulmonary, nasal, buccal, rectal, sublingual, transdermal, and parenteral. As used herein, the term "parenteral" includes subcutaneous, intravenous, intra-arterial, intraperitoneal, intracardiac, intrathecal, and intramuscular injection, as well as infusion injections.

In instances where parenteral administration is utilized, it may be necessary to employ somewhat bigger oligomers than those described previously, with molecular weights ranging from about 500 to 30K Daltons (e.g., having molecular weights of about 500, 1000, 2000, 2500, 3000, 5000, 7500, 10000, 15000, 20000, 25000, 30000 or even more).

The method may be used to treat any condition that may be remedied or prevented by administration of the particular conjugate. Those of ordinary skill in the art appreciate which conditions a specific conjugate may effectively treat. The actual dose to be administered may vary depend upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a therapeutically effective amount may range from about 0.001 mg to 1000 mg, preferably in doses from 0.01 mg/day to 750 mg/day, and more preferably in doses from 0.10 mg/day to 500 mg/day.

The unit dosage of any given conjugate may be administered in a variety of dosing schedules depending on the judgment of the clinician, needs of the patient, and so forth. The specific dosing schedule may be known by those of ordinary skill in the art or may be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

One advantage of administering the conjugates of the present invention is that a reduction in first pass metabolism may be achieved relative to the parent drug. Such a result is advantageous for many orally administered drugs that are substantially metabolized by passage through the gut. In this way, clearance of the conjugate can be modulated by selecting the oligomer molecular size, linkage, and position of covalent attachment providing the desired clearance properties. One of ordinary skill in the art can determine the ideal molecular size of the oligomer based upon the teachings herein. Preferred reductions in first pass metabolism for a conjugate as compared to the corresponding nonconjugated small drug molecule include: at least about 10%, at least about 20%, at least about 30; at least about 40; at least about 50%; at least about 60%, at least about 70%, at least about 80% and at least about 90%.

Thus, the invention provides a method for reducing the metabolism of an active agent. The method comprises the steps of: providing monodisperse or bimodal conjugates, each conjugate comprised of a moiety derived from a small molecule drug covalently attached by a stable linkage to a water-soluble oligomer, wherein said conjugate exhibits a reduced rate of metabolism as compared to the rate of metabolism of the small molecule drug not attached to the water-soluble oligomer; and administering the conjugate to a patient. Typically, administration is carried out via one type of administration selected from the group consisting of oral administration, transdermal administration, buccal administration, transmucosal administration, vaginal administration, rectal administration, parenteral administration, and pulmonary administration.

All articles, books, patents, patent publications and other publications referenced herein are incorporated by reference in their entireties.

EXPERIMENTAL

It is to be understood that while the invention has been described in conjunction with certain preferred and specific embodiments, the foregoing description as well as the examples that follow are intended to illustrate and not limit the scope of the invention. Other aspects, advantages and modifications within the scope of the invention will be apparent to those skilled in the art to which the invention pertains.

All chemical reagents referred to in the appended examples are commercially available unless otherwise indicated. The preparation of PEG-mers is described in, for example, U.S. Patent Application Publication No. 2005/0136031.

All NMR (nuclear magnetic resonance) data was generated by a 300 MHz NMR spectrometer manufactured by Bruker. A list of certain compounds as well as the source of the compounds is provided below.

Example 1

Synthesis of PEG-Nifedipine—"Approach A"

PEG-Nifedipine was prepared using a first approach. Schematically, the approach followed for this example is shown below (compound numbers in bold in the schematic correspond to the compound numbers provided in the text of this Example 1 alone).

Synthesis of PEG-Nifedipine—"Approach A" Schematic

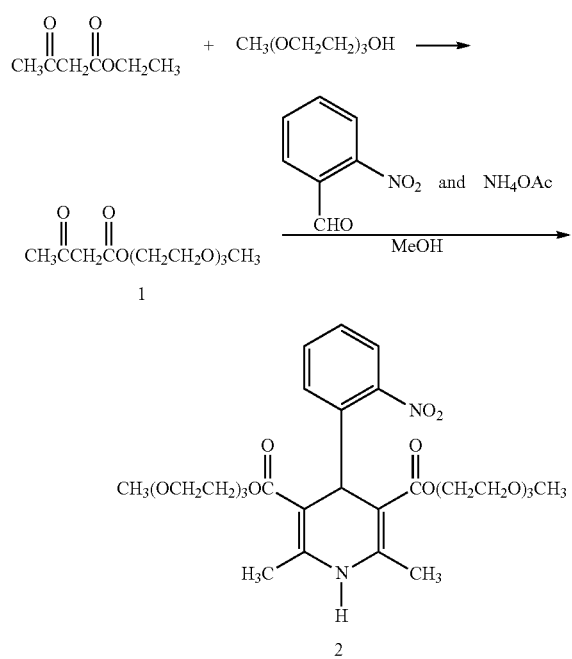

Synthesis of methyl tri(ethylene glycol)acetoacetate (1)

Tri(ethylene glycol)monomethyl ether (8.2 g, 50 mmol) and ethyl acetoacetate (9.75 g, 75 mmol) were heated to 180° C. for three hours and then ethanol and the excess ethyl acetoacetate were distilled out at 160° C. by reduced pressure distillation. The product (1) (11.16 g, yield 90%) is pure by NMR and used directly for the next step. $^1$H NMR (CDCl3): δ 4.30 (t, 2H), 3.73-3.53 (m, 10H), 3.48 (s, 2H), 3.38 (s, 3H), 2.27 (s, 3H).

Synthesis of 2,6-dimethyl 4-(2-nitrophenyl)-1,4-dihydropyridine-3,5-dicarboxylic acid dimethoxy tri(ethylene glycol)ester ("di-mPEG$_3$-nifedipine") (2)

Methyl tri(ethylene glycol)acetoacetate (1) (496 mg, 2.0 mmol), 2-nitrobenzylaldehyde (151 mg, 1.0 mmol), and ammonium acetate (77 mg, 1.0 mmol) were dissolved in methanol (10 ml). The reaction was heated to reflux for two days. The solvent was evaporated and the residue was subjected to flash chromatography (acetone/ethyl acetate=2%~4%) to obtain compound (2) (45 mg, yield 8%). $^1$H NMR (CDCl3): δ 7.72 (d, 1H), 7.51-7.45 (m, 2H), 7.26 (d, 1H), 5.90 (s, 1H), 5.84 (s, 1H), 4.27-4.21 (m, 2H), 4.10-4.05 (m, 2H), 3.66-3.52 (m, 20H), 3.38 (s, 6H), 2.32 (s, 6H). LC/MS: 628 [M+NH$_4$]$^+$, 633 [M+Na]$^+$.

Example 2

Synthesis of PEG-Nifedipine—"Approach B" Schematic

PEG-Nifedipine was prepared using a second approach. Schematically, the approach followed for this example is shown below (compound numbers in bold in the schematic correspond to the compound numbers provided in the text of this Example 2 alone).

Synthesis of PEG-Nifedipine—"Approach B" Schematic

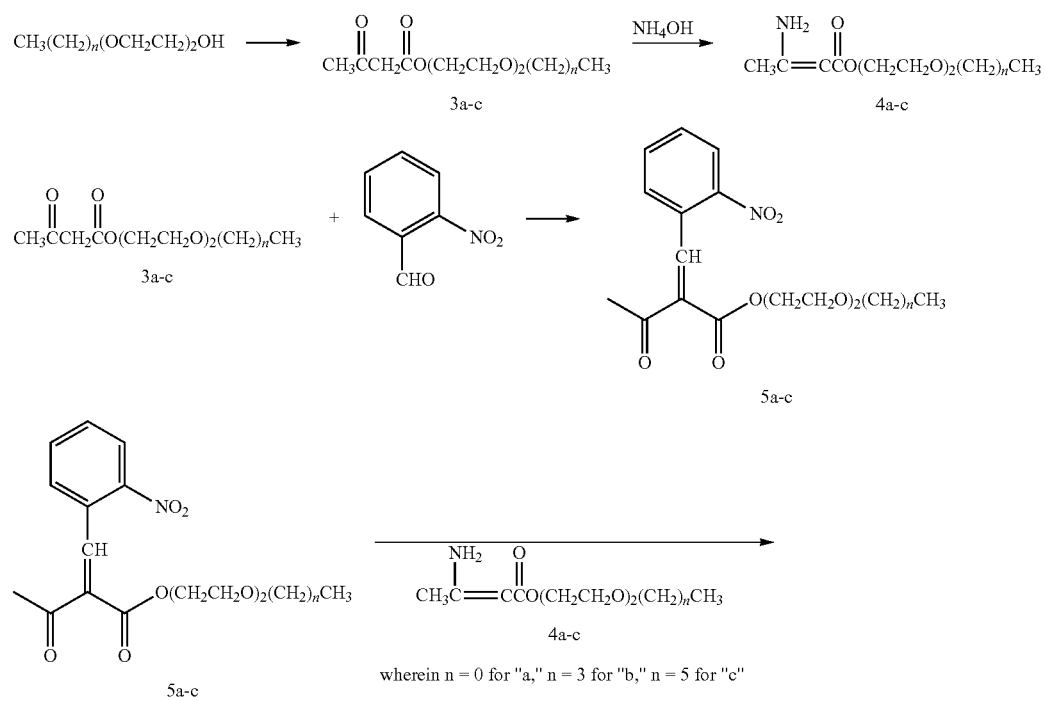

wherein n = 0 for "a," n = 3 for "b," n = 5 for "c"

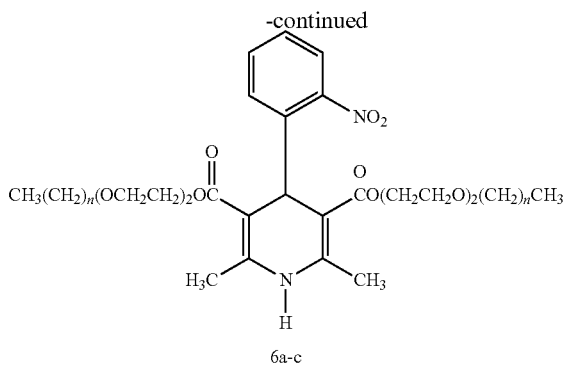

6a-c

Synthesis of methyl di(ethylene glycol)acetoacetate (3a)

Di(ethylene glycol)monomethyl ether (6.0 g, 50 mmol) and ethyl acetoacetate (9.75 g, 75 mmol) were heated to 180° C. for 3 hours and then ethanol and the excess ethyl acetoacetate were distilled out at 160° C. by reduced pressure distillation. The product (3a) (9.2 g, yield 90%) is pure by NMR and used directly for the next step. $^1$H NMR (CDCl3): δ 4.30 (t, 2H), 3.69 (t, 2H), 3.60 (t, 2H), 3.52 (t, 2H), 3.46 (s, 2H), 3.35 (s, 3H), 2.25 (s, 3H).

Synthesis of methyl di(ethylene glycol)3-aminocrotonate (4a)

Methyl di(ethylene glycol)acetoacetate (3a) (1.02 g, 5.0 mmol), ammonium hydroxide (0.78 ml, 6.0 mmol), and silica gel powder (60 mg) were mixed at room temperature. The reaction mixture was stirred at room temperature overnight. The solid was filtered off and the solvent was evaporated under reduced pressure. Toluene (20 ml) was added and distilled. The product (4a) (1.0 g, yield 99%) is pure by NMR and used directly for the next step. $^1$H NMR (CDCl3): δ 4.58 (s, 1H), 4.22 (t, 2H), 3.74 (t, 2H), 3.67 (t, 2H), 3.40 (s, 3H), 1.91 (s, 3H).

Synthesis of methyl di(ethylene glycol)2-(2-nitrobenzylidene)acetoacetate (5a)

Methyl di(ethylene glycol)acetoacetate (3a) (1.02 g, 5.0 mmol) and 2-nitrobenzylaldehyde (811 mg, 5.4 mmol) were dissolved in isopropyl alcohol (3 mL). Then, a mixture of dimethylamine (96.9 mg) and acetic acid (12.36 mg) was added. The reaction solution was stirred at 40° C. overnight. The solvent was evaporated by reduced pressure. The residue was subjected to flash chromatography (ethyl acetate/hexanes=50%~75%) to obtain the product (5a) as a mixture of geometric isomers (1.34 g, yield 80%). $^1$H NMR (CDCl3): δ 8.25-8.23 (m, 1H), 8.22 (s, 1H), 7.60 (d, 0.7H), 7.47 (d, 0.3H), 4.45 (t, 0.6H), 4.21 (t, 1.4H), 3.68-3.40 (m, 6H), 3.36 (s, 3H), 2.50 (s, 3H).

Synthesis of 2,6-dimethyl 4-(2-nitrophenyl)-1,4-dihydropyridine-3,5-dicarboxylic acid dimethoxy di(ethylene glycol)ester (6a)

Methyl di(ethylene glycol) 3-aminocrotonate (4a) (203 mg, 1.0 mmol) and methyl di(ethylene glycol) 2-(2-nitrobenzylidene)acetoacetate (5a) (337 mg, 1.0 mmol) were dissolved in methanol (5 ml). The reaction was heated to reflux for 30 hours. The solvent was evaporated and the residue was subjected to flash chromatography (acetone/ethyl acetate=2%-4%) to obtain compound (6a) (309 mg, yield 56%). $^1$H NMR (CDCl3): δ 7.72 (d, 1H), 7.51-7.45 (m, 2H), 7.26 (d, 1H), 5.85 (s, 1H), 5.68 (s, 1H), 4.27-4.25 (m, 2H), 4.10-4.07 (m, 2H), 3.662-3.52 (m, 20H), 3.38 (s, 6H), 2.32 (s, 6H). LC/MS: 523 [M+H]$^+$, 540 [M+NH$_4$]$^+$, 545 [M+Na]$^+$, 561 [M+K]$^+$.

Synthesis of butyl di(ethylene glycol)acetoacetate (3b)

Di(ethylene glycol) butyl ether (16.2 g, 100 mmol) and ethyl acetoacetate (19.5 g, 150 mmol) were heated to 180° C. for three hours and then ethanol and the excess ethyl acetoacetate were distilled out at 160° C. by reduced pressure distillation. The product (3b) (22.1 g, yield 90%) is pure by NMR and used directly for the next step. $^1$H NMR (CDCl3): δ 4.23 (t, 2H), 3.65 (t, 2H), 3.56 (t, 2H), 3.51 (t, 2H), 3.40 (s, 2H), 3.38 (t, 2H), 2.20 (s, 3H), 1.46 (m, 2H), 1.30 (m, 2H), 0.84 (t, 3H).

Synthesis of butyl di(ethylene glycol)3-aminocrotonate (4b)

Butyl di(ethylene glycol)acetoacetate (3b) (1.23 g, 5.0 mmol) and ammonium hydroxide (0.78 ml, 6.0 mmol), and silica gel powder (60 mg) were mixed at room temperature. The reaction mixture was stirred at room temperature overnight. The solid was filtered off and the solvent was evaporated under reduced pressure. Toluene (20 ml) was added and distilled. The product (1.22 g, yield 99%) is pure by NMR and used directly for the next step. $^1$H NMR (CDCl3): δ 4.58 (s, 1H), 4.23 (t, 2H), 3.74-3.59 (m, 6H), 3.49-3.45 (m, 2H), 1.92 (s, 3H), 1.58 (s, 2H), 1.35 (m, 2H), 0.93 (m, 3H).

Synthesis of methyl di(ethylene glycol)2-(2-nitrobenzylidene)acetoacetate (5b)

Butyl di(ethylene glycol)acetoacetate (3b) (1.23 g, 5.0 mmol) and 2-nitrobenzylaldehyde (811 mg, 5.4 mmol) were dissolved in isopropyl alcohol (3 mL). Then, a mixture of dimethylamine (96.9 mg) and acetic acid (12.36 mg) was added. The reaction solution was stirred at 40° C. overnight. The solvent was evaporated by reduced pressure. The residue was subjected to flash chromatography (ethyl acetate/hexanes=25%~40%) to obtain the product (5b) as a mixture of geometric isomers (1.42 g, yield 75%). $^1$H NMR (CDCl3): δ 8.25-8.23 (m, 1H), 8.22 (s, 1H), 7.69-7.51 (m, 2H), 7.48 (d, 0.7H), 7.28 (d, 0.3 H), 4.45 (t, 0.6H), 4.21 (t, 1.4H), 3.82-3.60 (m, 6H), 3.42 (t, 21-1), 2.50 (s, 3H), 1.54 (m, 2H), 1.35 (m, 2H), 0.91 (m, 3H).

Synthesis of 2,6-dimethyl 4-(2-nitrophenyl)-1,4-dihydropyridine-3,5-dicarboxylic acid dibutoxy di(ethylene glycol)ester (6b)

Butyl di(ethylene glycol) 3-aminocrotonate (4b) (245 mg, 1.0 mmol) and butyl di(ethylene glycol) 2-(2-nitrobenzylidene)acetoacetate (5b) (379 mg, 1.0 mmol) were dissolved in methanol (5 ml). The reaction was heated to reflux for three days. The solvent was evaporated and the residue was subjected to flash chromatography (ethyl acetate/hexanes=25%~40%) to obtain compound (6b) (250 mg, yield 41%). $^1$H NMR (CDCl3): δ 7.72 (d, 1H), 7.52-7.45 (m, 2H), 7.25 (d, 1H), 5.85 (s, 1H), 5.67 (s, 1H), 4.26-4.08 (m, 2H), 4.10-4.06 (m, 2H), 3.67-3.55 (m, 12H), 3.44 (t, 4H), 2.33 (s, 6H), 1.56 (m, 4H), 1.35 (m, 4H), 0.92 (t, 6H). LC/MS: 624 [M+NH$_4$]$^+$.

Synthesis of hexyl di(ethylene glycol)acetoacetate (3c)

Di(ethylene glycol) hexyl ether (19.0 g, 100 mmol) and ethyl acetoacetate (19.5 g, 150 mmol) were heated to 180° C. for three hours and then ethanol and the excess ethyl acetoacetate were distilled out at 160° C. by reduced pressure distillation. The product (3c) (24.1 g, yield 90%) is pure by NMR and used directly for the next step. $^1$H NMR (CDCl3): δ 4.30 (t, 2H), 3.72 (t, 2H), 3.64 (t, 2H), 3.61 (t, 2H), 3.48 (s, 2H), 3.44 (t, 2H), 2.27 (s, 3H), 1.56 (m, 2H), 1.29 (m, 6H), 0.88 (t, 3H).

Synthesis of hexyl di(ethylene glycol)3-aminocrotonate (4c)

Hexyl di(ethylene glycol)acetoacetate (3c) (1.37 g, 5.0 mmol) and ammonium hydroxide (0.78 ml, 6.0 mmol), and silica gel powder (60 mg) were mixed at room temperature. The reaction mixture was stirred at room temperature overnight. The solid was filtered off and the solvent was evaporated under reduced pressure. Toluene (20 ml) was added and distilled. The product (1.36 g, yield 99%) is pure by NMR and used directly for the next step. $^1$H NMR (CDCl3): δ 4.59 (s, 1H), 4.23 (t, 2H), 3.75-3.47 (m, 6H), 3.49-3.45 (m, 2H), 1.92 (s, 3H), 1.62 (s, 2H), 1.31 (m, 6H), 0.90 (t, 3H).

Synthesis of hexyl di(ethylene glycol)2-(2-nitrobenzylidene)acetoacetate (5c)

Hexyl di(ethylene glycol)acetoacetate (3c) (1.37 g, 5.0 mmol) and 2-nitrobenzylaldehyde (811 mg, 5.4 mmol) were dissolved in IPA (3 mL). Then a mixture of dimethylamine (96.9 mg) and acetic acid (12.36 mg) was added. The reaction solution was stirred at 40° C. overnight. The solvent was evaporated by reduced pressure. The residue was subjected to flash chromatography (ethyl acetate/hexanes=25%~40%) to obtain the product (5c) as a mixture of geometric isomers (1.42 g, yield 75%). $^1$H NMR (CDCl3): δ 8.26-8.23 (m, 1H), 7.69-7.61 (m, 2H), 7.56 (d, 0.7H), 7.28 (d, 0.3H), 4.46 (t, 0.6H), 4.21 (t, 1.4H), 3.83-3.41 (m, 6H), 3.42 (t, 3H), 2.51 (s, 3H), 1.57 (m, 2H), 1.31 (m, 6H), 0.90 (t, 3H).

Synthesis of 2,6-dimethyl 4-(2-nitrophenyl)-1,4-dihydropyridine-3,5-dicarboxylic acid dihexoxy di(ethylene glycol)Ester (6c)

Hexyl di(ethylene glycol) 3-aminocrotonate (4c) (273 mg, 1.0 mmol) and hexyl di(ethylene glycol) 2-(2-nitrobenzylidene)acetoacetate (5c) (407 mg, 1.0 mmol) were dissolved in methanol (5 ml). The reaction was heated to reflux for three days. The solvent was evaporated and the residue was subjected to flash chromatography (ethyl acetate/hexanes=25%~40%) to obtain compound (6c) (220 mg, yield 33%). $^1$H NMR (CDCl3): δ 7.73 (d, 1H), 7.54-7.45 (m, 2H), 7.25 (m, 1H), 5.85 (s, 1H), 5.72 (s, 1H), 4.28-4.07 (m, 2H), 4.12-4.05 (m, 2H), 3.67-3.43 (m, 12H), 3.40 (t, 4H), 2.32 (s, 6H), 1.63-1.52 (m, 4H), 1.37-1.29 (m, 12H), 0.89 (t, 6H). LC/MS: 680 [M+NH$_4$]$^+$, 685 [M+Na]$^+$.

Example 3

Calcium Channel Binding Assay

A calcium channel type L binding assay was performed having the following characteristics: $K_D$ (binding affinity)=0.20 nM; $B_{max}$ (receptor number): 166 fmol/mg tissue (wet weight). In the assay, rat cortical membranes were used as a receptor source and the radioligand [$^3$H]Nitrendipine (70-87 Ci/mmol) was used at a final ligand concentration of 0.2 nM. The non-specific determinant was nifedipine (0.1 µM) and both the reference compound and positive control was nifedipine. The reactions were carried out in 50 mM TRIS-HCl (pH 7.7) at 25° C. for 60 minutes. The reaction was terminated by rapid vacuum filtration onto glass fiber filters. Radioactivity trapped onto the filters was determined and compared to control values in order to ascertain any interactions of test compound with the nitredipine binding site (Gould, Murphy, and Snyder. Molecular Pharmacology 25, 235-241 (1984)). In the assay: nifedipine exhibited an IC$_{50}$ 1.7×10$^{-9}$ and compound (2) from Example 1 had an IC$_{50}$ of 1.6×10$^{-7}$; nifedipine exhibited an IC$_{50}$ 1.88×10$^{-9}$ and compound (6a) from Example 2 had an IC$_{50}$ of 6.74×10$^{-8}$; nifedipine exhibited an IC$_{50}$ 2.12×10$^{-9}$ and compound (6b) from Example 2 had an IC$_{50}$ of 1.55×10$^{-8}$; nifedipine exhibited an IC$_{50}$ 1.77×10$^{-9}$ and compound (6c) from Example 2 had an IC$_{50}$ of 5.56×10$^{-8}$.

Example 4

Synthesis of PEG-Verapamil—"Approach A"

PEG-Verapamil was prepared using a first approach. Schematically, the approach followed for this example is shown below (compound numbers in bold in the schematic correspond to the compound numbers provided in the text of this Example 4 alone).

Synthesis of PEG-Verapamil—"Approach A" Schematic

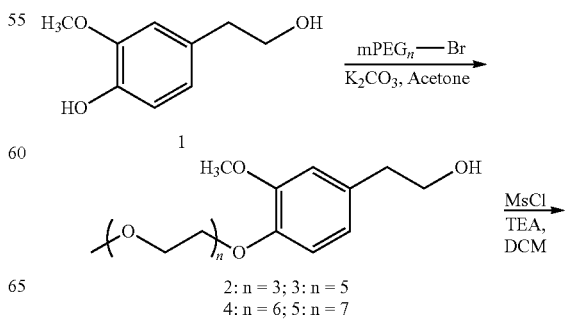

2: n = 3; 3: n = 5
4: n = 6; 5: n = 7

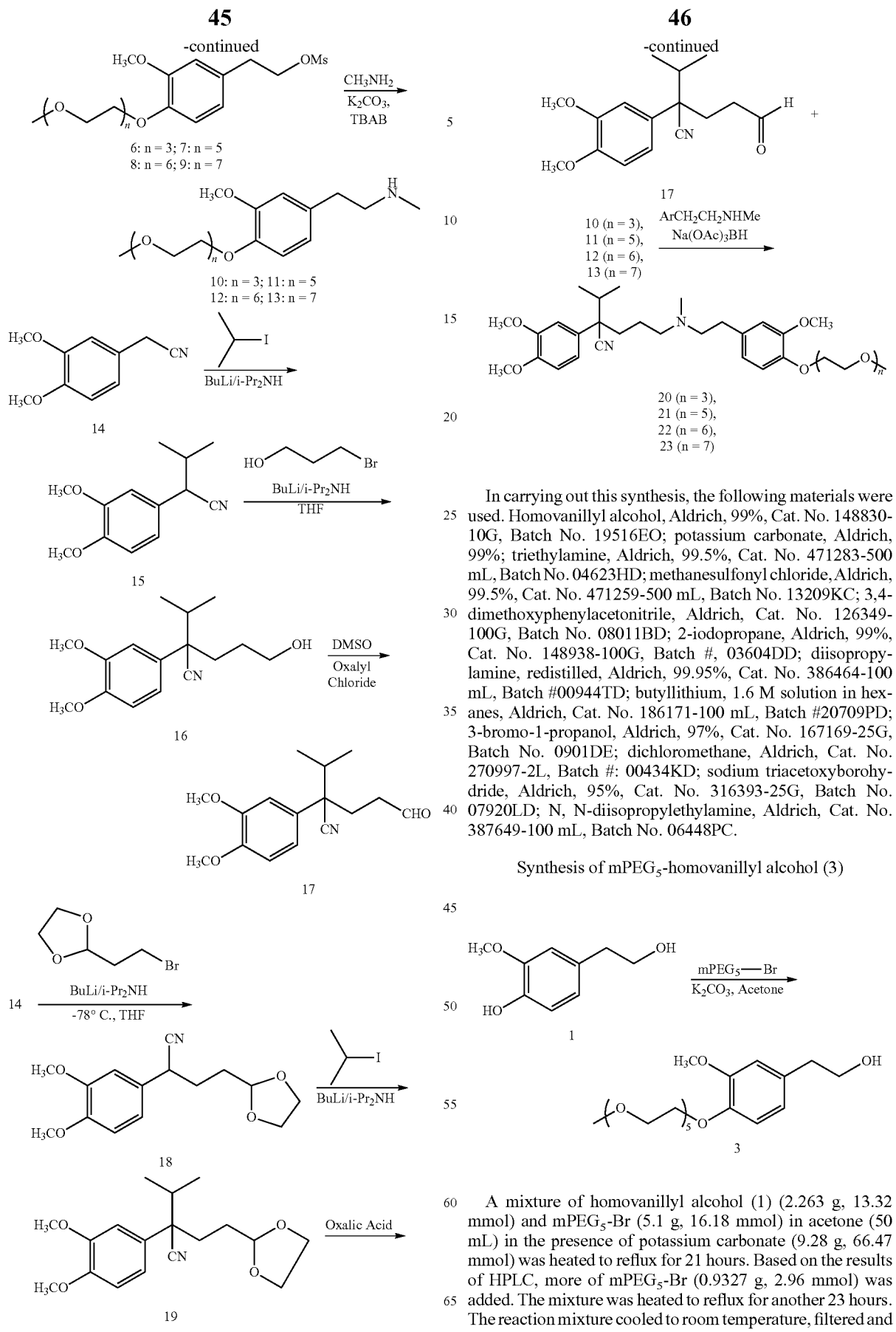

In carrying out this synthesis, the following materials were used. Homovanillyl alcohol, Aldrich, 99%, Cat. No. 148830-10G, Batch No. 19516EO; potassium carbonate, Aldrich, 99%; triethylamine, Aldrich, 99.5%, Cat. No. 471283-500 mL, Batch No. 04623HD; methanesulfonyl chloride, Aldrich, 99.5%, Cat. No. 471259-500 mL, Batch No. 13209KC; 3,4-dimethoxyphenylacetonitrile, Aldrich, Cat. No. 126349-100G, Batch No. 08011BD; 2-iodopropane, Aldrich, 99%, Cat. No. 148938-100G, Batch #, 03604DD; diisopropylamine, redistilled, Aldrich, 99.95%, Cat. No. 386464-100 mL, Batch #00944TD; butyllithium, 1.6 M solution in hexanes, Aldrich, Cat. No. 186171-100 mL, Batch #20709PD; 3-bromo-1-propanol, Aldrich, 97%, Cat. No. 167169-25G, Batch No. 0901DE; dichloromethane, Aldrich, Cat. No. 270997-2L, Batch #: 00434KD; sodium triacetoxyborohydride, Aldrich, 95%, Cat. No. 316393-25G, Batch No. 07920LD; N, N-diisopropylethylamine, Aldrich, Cat. No. 387649-100 mL, Batch No. 06448PC.

Synthesis of mPEG$_5$-homovanillyl alcohol (3)

A mixture of homovanillyl alcohol (1) (2.263 g, 13.32 mmol) and mPEG$_5$-Br (5.1 g, 16.18 mmol) in acetone (50 mL) in the presence of potassium carbonate (9.28 g, 66.47 mmol) was heated to reflux for 21 hours. Based on the results of HPLC, more of mPEG$_5$-Br (0.9327 g, 2.96 mmol) was added. The mixture was heated to reflux for another 23 hours. The reaction mixture cooled to room temperature, filtered and washed with acetone. The solvent was removed under reduced pressure to afford the crude product (3). Based on the ¹H-NMR, some mPEG₅-Br was contained in the crude mixture. The mixture was used without purification for the next step. ¹H-NMR (CDCl₃): δ 6.86-6.83 (m, 1 H), 6.73-6.70 (m, 2 H), 4.14 (t, J=4.8-5.7 Hz, 2 H), 3.86-3.80 (m, 7 H), 3.72-3.69 (m, 2 H), 3.66-3.58 (m, 12 H), 3.54-3.50 (m, 2 H), 3.35 (s, 3 H), 2.79 (t, J=6.3-6.6 Hz, 2 H). LC-MS: 403.3 (MH⁺), 425.3 (MNa⁺).

Synthesis of mPEG₅-homovanillyl mesylate (7)

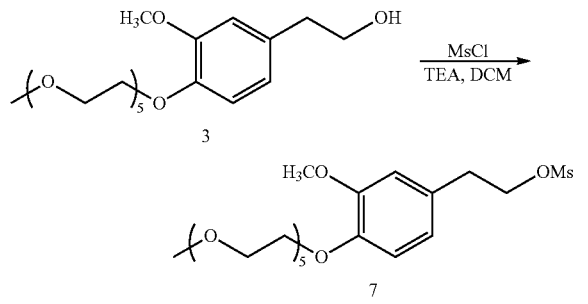

Triethylamine (4.0 ml, 28.55 mmol) was added to a stirred solution of the above crude mPEG₅-homovanillyl alcohol (3) in DCM (40 mL) at room temperature. Methanesulfonyl chloride (1.7 ml, 21.77 mmol) was then added. The resulting mixture was stirred at room temperature for 19 hours. Water was added to quench the reaction. The organic phase was separated and the aqueous phase was extracted with dichloromethane (2×30 mL). The combined organic solution was washed with brine, dried over Na₂SO₄, concentrated to afford yellow oil as the product (7). ¹H-NMR (CDCl₃): δ 6.86-6.83 (m, 1 H), 6.74-6.72 (m, 2 H), 4.37 (t, J=6.9-7.2 Hz, 2 H), 4.14 (t, J=5.1-5.4 Hz, 2 H), 3.85 (t, J=5.1 Hz, 2 H), 3.83 (s, 3 H), 3.73-3.69 (m, 2 H), 3.67-3.59 (m, 12 H), 3.55-3.52 (m, 2 H), 3.36 (s, 3 H), 2.98 (t, J=6.9-7.2 Hz, 2 H), 2.85 (s, 3 H). LC-MS: 481.4 (MO, 503.4 (MNa⁺).

Synthesis of mPEG₅-homovanillyl methylamine (11)

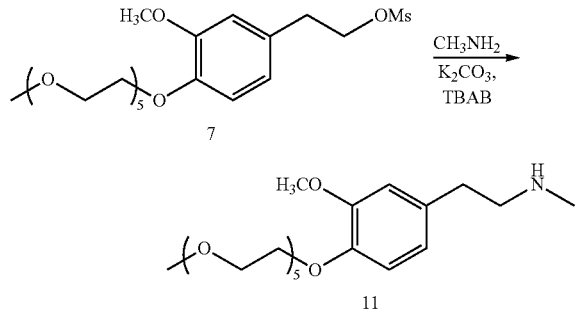

A mixture of the above mPEG₅-homovanillyl mesylate (7) (13.32 mmol), potassium carbonate (9.8678 g, 70.68 mmol) and tetrabutylammonium bromide (530 mg, 1.63 mmol) in 33 mL of methylamine solution (2.0 M in THF, 66 mmol) was stirred for 73.5 hours at room temperature. Water was added to quench the reaction and the mixture was concentrated to remove the organic solvents under reduced pressure. The aqueous solution was extracted with DCM (3×40 mL). The combined organic solution was washed with brine, dried over sodium sulfate, concentrated. The residue was purified by flash column chromatography on silica gel using MeOH/DCM (0-10%) and TEA/MeOH/DCM (1/1/9) to afford an oil as the product (11). ¹H-NMR (CDCl₃): δ 6.84-6.81 (m, 1 H), 6.72-6.69 (m, 2 H), 4.14 (t, J=4.8-5.4 Hz, 2 H), 3.84 (t, J=5.4 Hz, 2 H), 3.82 (s, 3 H), 3.72-3.70 (m, 2 H), 3.66-3.59 (m, 12 H), 3.55-3.51 (m, 2 H), 3.36 (s, 3 H), 2.85-2.73 (m, 4 H), 2.44 (s, 3 H). LC-MS: 416.4 (MH⁺), 438.4 (MNa⁺).

Synthesis of mPEG₇-homovanillyl methylamine (13)

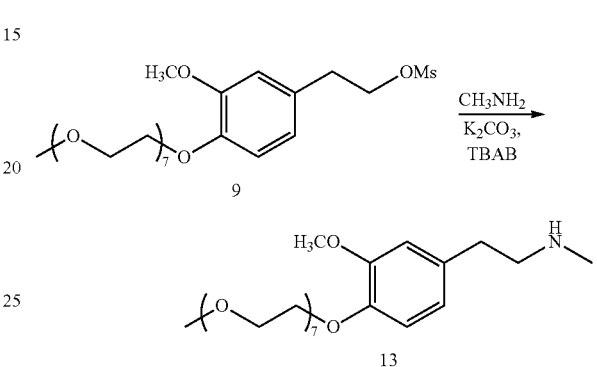

Methylamine (2.0 M solution in THF, 26 ml, 52 mmol) was added to a stirred mixture of crude mPEG₇-homovanillyl mesylate (9) (12.14 mmol) (previously prepared in a manner similar to compound (7) with the exception that mPEG₇-Br is used in place of mPEG₅-Br), potassium carbonate (8.616 g, 61.72 mmol) and tetrabutylammonium bromide (400 mg, 1.23 mmol) were added. After stirring for 24 hours, THF (15 mL) and more of methylamine solution (2.0 M solution in THF, 5.5 mL, 18 mmol) were added. The reaction mixture was stirred at room temperature for 49 hours, water was added and the mixture was concentrated to remove the organic solvents under reduced pressure. The aqueous solution was extracted with DCM (3×60 mL). The combined organic solution was washed with brine (2×100 mL), dried over sodium sulfate, concentrated. The residue was purified by flash column chromatography on silica gel using MeOH/DCM (0-10%) and TEA/MeOH/DCM (0.5/1/9) to afford an oil as the product. ¹H-NMR (CDCl₃): δ 6.84-6.82 (m, 1 H), 6.72-6.70 (m, 2 H), 4.14 (t, J=5.1-5.4 Hz, 2 H), 3.84 (t, J=5.4 Hz, 2 H), 3.82 (s, 3 H), 3.73-3.69 (m, 2 H), 3.66-3.61 (m, 20 H), 3.55-3.51 (m, 2 H), 3.36 (s, 3 H), 2.89-2.75 (m, 4 H), 2.46 (s, 3 H).

Synthesis of 2-(3,4-dimethoxy)-5-hydroxy-2-isopropyl-pentanenitrile (16)

A solution of butyllithium (1.6 M solution in hexanes, 2.5 mL, 4.0 mmol) was added via syringe to a solution of diisopropylamine (0.53 mL, 3.75 mmol) in anhydrous THF (18 mL) at −78° C. After five minutes, a solution of 2-(3,4-dimethoxyphenyl)-2-isopropylacetonitrile (15) (273 mg, 1.25 mmol) (previously prepared by reacting 2-iodopropane with 2-(3,4-dimethoxyphenyl)-acetonitrile (14) in a solution diisopropylamine to which butyllithium was added) in THF (3 mL) was added via syringe. The mixture was stirred at −78° C. for ten minutes and then 3-brom-1-propanol (246 mg, 1.70 mmol) was added. The mixture was stirred for 21 hours. During this period, the temperature was changed from −78°

C. to room temperature. Saturated NH₄Cl solution (5 mL) was added to quench the reaction and extracted with ether (3×20 mL). After washing with brine and drying with sodium sulfate, the solvent was removed under reduced pressure and the residue was purified by flash column chromatography on SiO₂ using EtOAc/hexanes (0-30%) to afford the product (16) (111.7 mg) in 34% yield. ¹H-NMR (CDCl₃): δ 6.90-6.86 (m, 1 H), 6.81-6.79 (m, 1 H), 3.84 (s, 3 H), 3.83 (s, 3 H), 3.53 (m, 2 H), 2.24-2.17 (m, 1 H), 2.08-1.99 (m, 1 H), 1.92-1.82 (m, 1 H), 1.60-1.50 (m, 1 H), 1.25-1.87 (m, 1 H), 1.14 (d, J=6.9 Hz, 3 H), 0.75 (d, J=6.6 Hz, 3 H). LC-MS: 278.1 (MH⁺), 295.1 (M+H₂O)⁺, 300.2 (MNa⁺).

A second run, following a similar procedure, was performed. Briefly, a solution of butyllithium (1.6 M solution in hexanes, 8.0 mL, 12.80 mmol) was added via syringe to a solution of diisopropylamine (1.8 mL, 12.73 mmol) in anhydrous THF (8 mL) at −78° C. After five minutes, a solution of 2-(3,4-dimethoxyphenyl)-2-isopropylacetonitrile (15) (1.145 g, 5.22 mmol) (previously prepared by reacting 2-iodopropane with 2-(3,4-dimethoxyphenyl)-acetonitrile (14) in a solution diisopropylamine to which butyllithium was added) in THF (5 mL) was added via syringe and then followed by an addition of 3-brom-1-propanol (0.45 mL, 4.99 mmol). The resulting solution was stirred at −78° C. for four hours, at room temperature for 23.5 hours. Saturated NH₄Cl solution (10 mL) was added to quench the reaction and extracted with ether (3×50 mL). After washing with brine, drying with sodium sulfate, the solvent was removed under reduced pressure and the residue was purified by flash column chromatography on SiO₂ using EtOAc/hexanes (0-50%) to afford the product (16) (1.2239 g) in 85% yield.

Synthesis of 2-(3,4-dimethoxyphenyl)-2-isopropyl-5-oxopentanenitrile (17)

DMSO (0.07 mL, 0.987 mmol) in dichloromethane (3 mL) was added to a solution of oxalyl chloride (2.0 M solution in dichloromethane, 0.3 mL, 0.6 mmol) in dichloromethane (5 mL) at −78° C. The solution was stirred at −78° C. for 3 minutes and 2-(3,4-dimethoxy)-5-hydroxy-2-isopropyl-pentanenitrile (16) (110 mg, 0.397 mmol) in dichloromethane (3.5 mL) was added. The mixture was stirred at −78° C. for ten minutes and triethylamine (0.5 mL) was added. The resulting reaction mixture was stirred at −78° C. for three hours, and then the dry ice-acetone bath was removed, the mixture was warmed up to room temperature. The reaction mixture was stirred at room temperature for 2.5 hours. Saturated sodium chloride solution (5 mL) was added to quench the reaction. The organic solution was separated and the aqueous solution was extracted with dichloromethane (3×20 mL). The combined organic solution was washed with brine (60 mL), dried over sodium sulfate, concentrated to afford the crude product (109 mg), which was used in the next reaction without further purification. Based on the results of HPLC, the purity of the product was over 96%. ¹H-NMR (CDCl₃): δ 9.68 (s, 1 H), 6.92-6.80 (m, 3 H), 3.874 (s, 3 H), 3.869 (s, 3 H), 2.67-2.55 (m, 1 H), 2.48-2.39 (m, 1 H), 2.23-2.03 (m, 3 H), 1.16 (d, J=6.9 Hz, 3 H), 0.79 (d, J=6.6 Hz, 3 H). LC-MS: 276.2 (MH⁺), 293.2 (M+H₂O)⁺, 298.2 (MNa⁺).

A second run, following the same procedure, was followed, using the alcohol (16) (1.2239 g, 4.413 mmol), DMSO (1.0 mL, 14.10 mmol), oxalyl chloride (2.0 M solution in dichloromethane, 7.0 mL, 14.0 mmol), triethylamine (4 mL) and dichloromethane (28 mL). The crude product was 1.537 g.

Synthesis of 2-cyano-2-(3,4-dimethoxyphenyl)-2-isopropylethyl-1,3-dioxolane (19)

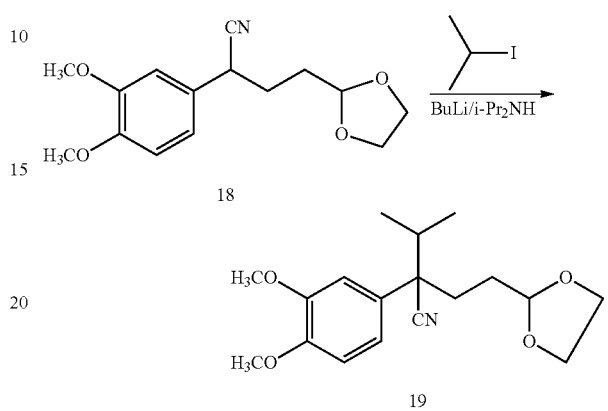

A solution of butyllithium (1.6 M solution in hexanes, 7.0 mL, 11.2 mmol) was added via syringe to a solution of diisopropylamine (1.5 mL, 10.61 mmol) in anhydrous THF (25 mL) at −78° C. And then a solution of 2-(3,4-dimethoxyphenyl)-4-(1,3)-dioxolan-2-yl-butyronitrile (18) (709 mg, 2.56 mmol) (previously prepared by reacting 2-(2-bromoethyl)-1,3-dioxolane with 2-(3,4-dimethoxyphenyl)-acetonitrile (14) in a solution diisopropylamine to which butyllithium was added) in THF (10 mL) was added via syringe. The mixture was stirred at −78° C. for five minutes and then 2-iodopropane (0.4 mL, 3.96 mmol) was added. The mixture was stirred at −78° C. for five hours and then at room temperature for 17.5 hours. Saturated NH₄Cl solution (10 mL) was added to quench the reaction. Ethyl ether (60 mL) was added and the etheral solution was isolated. The aqueous solution was extracted with ether (2×20 mL). After washing with brine, drying with sodium sulfate, the solvent was removed under reduced pressure and the residue was purified by flash column chromatography on SiO₂ using EtOAc/hexanes (0-30%) to afford the product (19) (397 mg) in 49% yield. ¹H-NMR (CDCl₃): δ 6.86-6.82 (m, 3 H), 4.80 (t, J=4.2-4.8 Hz, 1 H), 3.95-3.77 (m, 4 H), 3.878 (s, 3 H), 3.867 (s, 3 H), 2.24 (dt, J=3.9-4.2 Hz, J=12.9-13.2 Hz, 1 H), 2.11-2.02 (m, 1 H), 1.91 (dt, 1=3.9 Hz, J=12.6 Hz, 1 H), 1.72 (tt, J=3.9-4.2 Hz, J=12.6-13.2 Hz, 1 H), 1.37-1.24 (m, 1 H), 1.16 (d, J=6.6 Hz, 3 H), 0.80 (d, J=6.9 Hz, 3 H). LC-MS: 342.083 (MNa⁺).

Synthesis of 2-(3,4-dimethoxyphenyl)-2-isopropyl-5-oxopentanenitrile (17)

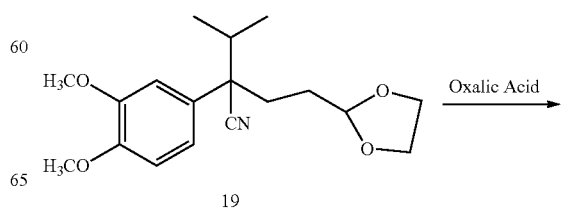

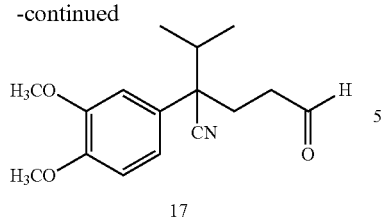

17

Oxalic acid dehydrate (504.6 mg, 3.96 mmol) was added to a solution of the acetal (19) (372 mg, 1.16 mmol) in acetone (10 mL) and water (10 mL). The resulting mixture was stirred at 80° C. for four hours. The reaction mixture was cooled to room temperature. Potassium carbonate (1.3 g) was added to quench the reaction. The mixture was extracted with ethyl ether (3×20 mL). The organic solution was washed with brine, dried over sodium sulfate, concentrated to afford the crude product (17) (293 mg), which was used in the next step without further purification. The product was confirmed by H-NMR spectra.

Synthesis of O-mPEG$_3$-verapamil (20)

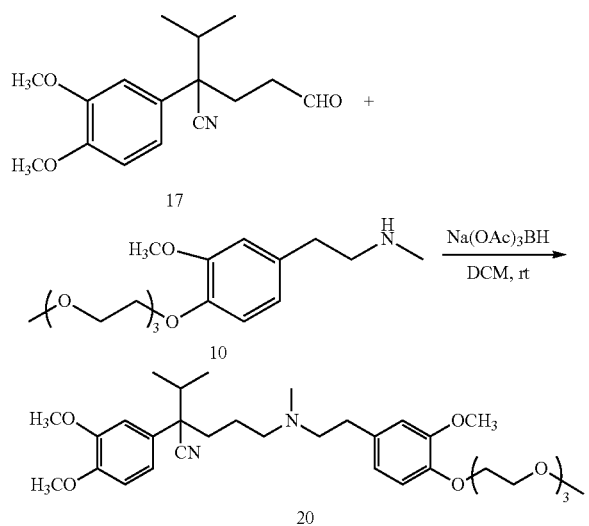

Sodium triacetoxyborohydride (178.6 mg, 0.801 mmol) was added to a stirred solution of 2-(3,4-dimethoxyphenyl)-2-isopropyl-5-oxo-pentanenitrile (17) (106 mg, 0.385 mmol) and mPEG$_3$-homovanillyl methylamine (10) (134 mg, 0.409 mmol) in dichloromethane (6 mL) at room temperature. The resulting reaction mixture was stirred at room temperature for three hours. Water was added to quench the reaction. The organic solution was separated and the aqueous solution was extracted with dichloromethane (2×20 mL). The combined organic solution was washed with brine, dried over sodium sulfate, concentrated. The residue was purified by flash column chromatography on SiO$_2$ using EtOAC/hexanes (0-100%) and MeOH/Et$_3$N/EtOAc (1/1/9) to afford the product (134 mg, 59% yield), with 2-(3,4-dimethoxy)-5-hydroxy-2-isopropyl-pentanenitrile (16) (27 mg, 26% yield). $^1$H-NMR of (20) (CDCl$_3$): δ 6.88-6.77 (m, 4 H), 6.64-6.60 (m, 2 H), 4.10 (t, J=4.8-5.4 Hz, 2 H), 3.84-3.79 (m, 11 H), 3.70-3.67 (m, 2 H), 3.64-3.59 (m, 4 H), 3.51-3.48 (m, 2 H), 3.33 (s, 3 H), 2.63-2.80 (m, 2 H), 2.49-2.42 (m, 2 H), 2.38-2.23 (m, 2 H), 2.13 (s, 3 H), 2.10-1.97 (m, 2 H), 1.79 (dt, J=4.2 Hz, J=12.3 Hz, 2 H), 1.57-1.45 (m, 1 H), 1.50-1.05 (m, 1 H), 1.14 (d, J=6.6 Hz, 3 H), 0.74 (d, J=6.6 Hz, 3 H). LC-MS: 357.4 (MH).

Synthesis of O-mPEG$_5$-verapamil (21)

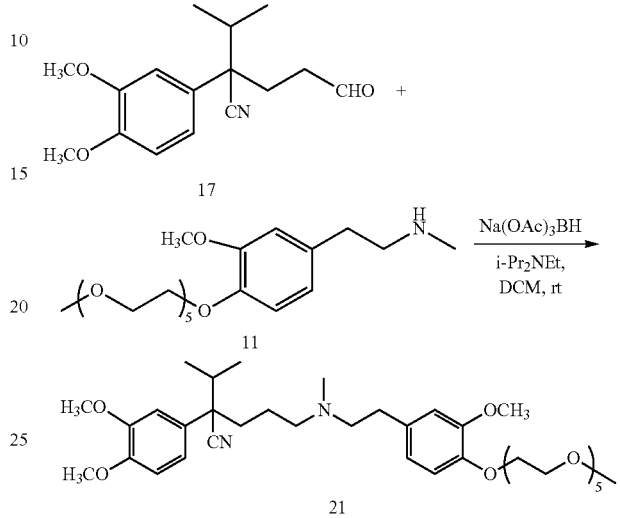

A mixture of mPEG$_5$-homovanillyl methylamine (11) (123 mg, 0.447 mmol) and 2-(3,4-dimethoxyphenyl)-2-isopropyl-5-oxo-pentanenitrile (17) (210 mg, 0.505 mmol) was stirred for ten minutes and then i-Pr$_2$NEt (0.02 mL) was added. After ten minutes at room temperature, sodium triacetoxyborohydride (138 mg, 0.619 mmol) was added. After 25 minutes, more of Na(OAc)$_3$BH (90 mg, 0.403 mmol) was added. The resulting reaction mixture was stirred at room temperature for 5.5 hours. Water was added to quench the reaction. The organic solution was separated and the aqueous solution was extracted with dichloromethane (2×20 mL). The combined organic solution was washed with brine (60 mL), dried over sodium sulfate, concentrated. The residue was purified by flash column chromatography on SiO$_2$ using EtOAC/hexanes (30-100%) and Et$_3$N/EtOAc (1/20) to afford the product (125 mg, 42% yield). $^1$H-NMR (CDCl$_3$): δ 6.84-6.79 (m, 4 H), 6.66-6.62 (m, 2 H), 4.12 (t, J=4.8-5.1 Hz, 2 H), 3.86-3.81 (m, 11 H), 3.72-3.68 (m, 2 H), 3.66-3.59 (m, 12 H), 3.55-3.51 (m, 2 H), 3.35 (s, 3 H), 2.65-2.61 (m, 2 H), 2.49-2.44 (m, 2 H), 2.37-2.29 (m, 2 H), 2.15 (s, 3 H), 2.13-1.99 (m, 2 H), 1.81 (dt, J=4.2 Hz, J-=12.3 Hz, 2 H), 1.54 (m, 1 H), 1.16 (d, J=6.6 Hz, 3 H), 1.12 (m, 1 H), 0.77 (d, J=6.6 Hz, 3 H). LC-MS: 675.5 (MO, 697.5 (MNa$^+$).

Synthesis of O-mPEG$_6$-verapamil (22)

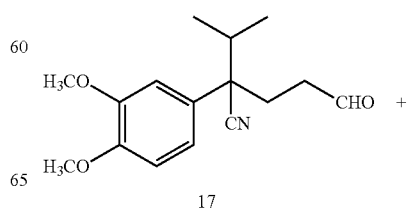

17

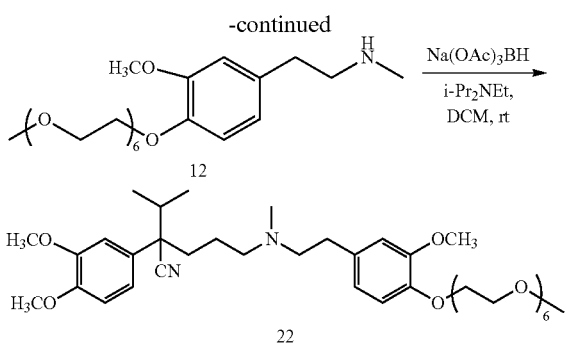

A mixture of mPEG₆-homovanillyl methylamine (12) (306 mg, 0.67 mmol) and 2-(3,4-dimethoxyphenyl)-2-isopropyl-5-oxo-pentanenitrile (17) (170 mg, 0.62 mmol) was stirred for 5 minutes and then i-Pr₂NEt (0.03 mL, 0.17 mmol) was added. After five minutes at room temperature, sodium triacetoxyborohydride (296 mg, 1.33 mmol) was added. The resulting reaction mixture was stirred at room temperature for 23 hours. Water was added to quench the reaction. The organic solution was separated and the aqueous solution was extracted with dichloromethane (2×30 mL). The combined organic solution was washed with brine (60 mL), dried over sodium sulfate, concentrated. The residue was purified by flash column chromatography on SiO₂ to afford the product (195 mg, 44% yield). ¹H-NMR (CDCl₃): δ 6.82-6.77 (m, 4 H), 6.65-6.60 (m, 2 H), 4.10 (t, J=5.1-5.4 Hz, 2 H), 3.84-3.79 (m, 11 H), 3.70-3.66 (m, 2 H), 3.64-3.57 (m, 16 H), 3.53-3.49 (m, 2 H), 3.33 (s, 3 H), 2.65-2.61 (m, 2 H), 2.51-2.46 (m, 2 H), 2.39-2.29 (m, 2 H), 2.16 (s, 3 H), 2.13-1.98 (m, 2 H), 1.82 (dt, J=4.2 Hz, J=12.3 Hz, 2 H), 1.54-1.48 (m, 1 H), 1.14 (d, J=6.6 Hz, 3 H), 1.11 (m, 1 H), 0.75 (d, J=6.6 Hz, 3 H). LC-MS: 719.5 (MO, 741.5 (MNa⁺).

Synthesis of O-mPEG₇-verapamil (23)

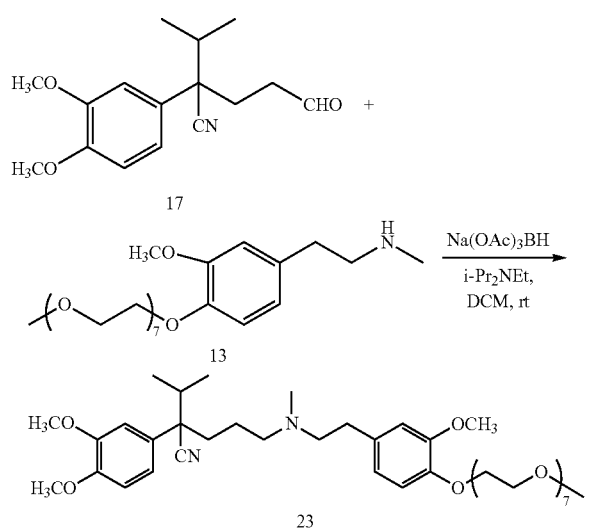

i-Pr₂NEt (0.03 mL) was added to a stirred mixture of mPEG₇-homovanillyl methylamine (13) (290 mg, 0.576 mmol) and 2-(3,4-dimethoxyphenyl)-2-isopropyl-5-oxo-pentanenitrile (17) (167 mg, 0.607 mmol). After five min at room temperature, sodium triacetoxyborohydride (260 mg, 1.104 mmol) was added. The resulting reaction mixture was stirred at room temperature for 5.5 hours. Water was added to quench the reaction. The organic solution was separated and the aqueous solution was extracted with dichloromethane (2×20 mL). The combined organic solution was washed with brine, dried over sodium sulfate, concentrated. The residue was purified by flash column chromatography on SiO₂ using EtOAC/hexanes (30-100%) and Et₃N/MeOH/EtOAc (0.5/1/25) to afford the product (302 mg, 69% yield). ¹H-NMR (CDCl₃): δ 6.83-6.79 (m, 4 H), 6.67-6.62 (m, 2 H), 4.12 (t, J=5.1-5.4 Hz, 2 H), 3.86-3.81 (m, 11 H), 3.72-3.68 (m, 2 H), 3.66-3.59 (m, 20 H), 3.55-3.51 (m, 2 H), 3.35 (s, 3 H), 2.65-2.60 (m, 2 H), 2.49-2.44 (m, 2 H), 2.36-2.01 (m, 2 H), 2.15 (s, 3 H), 2.13-2.01 (m, 2 H), 1.81 (dt, J=4.2 Hz, J=12.3 Hz, 2 H), 1.53 (m, 1 H), 1.16 (d, J=6.6 Hz, 3 H), 1.12 (m, 1 H), 0.77 (d, J=6.6 Hz, 3 H). LC-MS: 763.5.5 (MO, 785.5 (MNa⁺).

Example 5

Synthesis of PEG-Verapamil—"Approach B"

PEG-Verapamil was prepared using a second approach. Schematically, the approach followed for this example is shown below (compound numbers in bold in the schematic correspond to the compound numbers provided in the text of this Example 5 alone).

Synthesis of PEG-Verapamil—"Approach B" Schematic

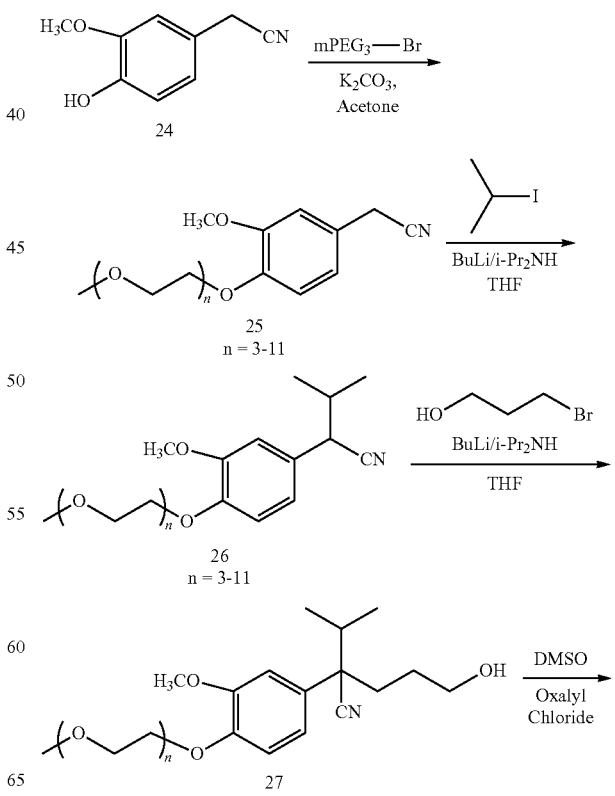

-continued

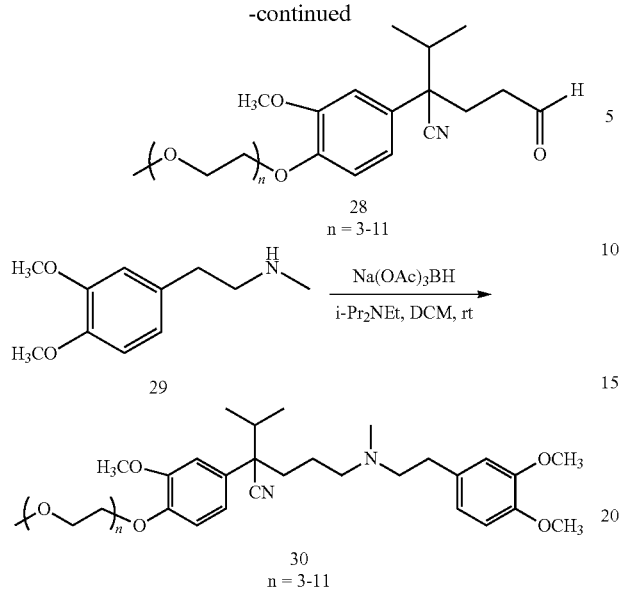

In carrying out this synthesis, the following materials were used. Homovanillyl alcohol, Aldrich, 99%, Cat. No. 148830-10G, Batch No. 19516EO; potassium carbonate, Aldrich, 99%; triethylamine, Aldrich, 99.5%, Cat. No. 471283-500 mL, Batch No. 04623HD; methanesulfonyl chloride, Aldrich, 99.5%, Cat. No. 471259-500 mL, Batch No. 13209KC; 3,4-dimethoxyphenylacetonitrile, Aldrich, Cat. No. 126349-100G, Batch No. 0801 IBD; 2-iodopropane, Aldrich, 99%, Cat. No. 148938-100G, Batch #, 03604DD; diisopropylamine, redistilled, Aldrich, 99.95%, Cat. No. 386464-100 mL, Batch #00944TD; butyllithium, 1.6 M solution in hexanes, Aldrich, Cat. No. 186171-100 mL, Batch #20709PD; 3-bromo-1-propanol, Aldrich, 97%, Cat. No. 167169-25G, Batch No. 0901DE; dichloromethane, Aldrich, Cat. No. 270997-2L, Batch #: 00434KD; sodium triacetoxyborohydride, Aldrich, 95%, Cat. No. 316393-25G, Batch No. 07920LD; N, N-diisopropylethylamine, Aldrich, Cat. No. 387649-100 mL, Batch No. 06448PC; N-methylhomoveratrylamine, Aldrich, Cat. No. 334774, Batch No. 10421EO.

Synthesis of 4-mPEG$_3$-3-methoxyphenylacetonitrile (25)

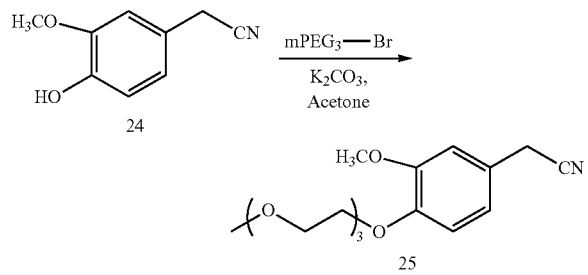

A mixture of 4-hydroxy-3-methoxyphenylacetonitrile (24) (503 mg, 3.05 mmol) and mPEG$_3$-Br (830 mg, 3.65 mmol, 1.2 eq) in the presence of potassium carbonate (2.35 g, 16.83 mmol) in acetone (15 mL) was heated to reflux for 17 hours. The mixture was cooled to room temperature, filtered and washed with acetone and DCM. The solution was concentrated. The residue was purified by column chromatography on silica gel using MeOH/DCM (0-2%) to afford pure product (25) (738 mg) and a mixture of the product and mPEG$_3$-Br (277 mg). No attempt was made to further purify the mixture.

A second run, following a similar procedure, was performed. A mixture of 4-hydroxy-3-methoxyphenylacetonitrile (24) (1.81 g, 10.98 mmol) and mPEG$_3$-Br (2.505 g, 11.03 mmol, 1.005 eq) in the presence of potassium carbonate (6.693 g, 47.94 mmol) in acetone (35 mL) was heated to reflux for 20.5 hours. The mixture was cooled to room temperature, filtered and washed with acetone. The solution was concentrated. The residue was purified by column chromatography on silica gel using EtOAc/hexanes (0-50%) to afford pure product (25) (2.826 g, 83%). Note: Based on the results of HPLC and TLC, a small amount of the starting nitrile material (24) was observed. No mPEG$_3$-Br was isolated and observed in the NMR spectra. $^1$H-NMR (CDCl$_3$): δ 6.92-6.89 (m, 1 H), 6.82-6.79 (m, 2 H), 4.16 (t, =5.1-5.7 Hz, 2 H), 3.88-3.85 (m, 5 H), 3.74-3.70 (m, 2 H), 3.67-3.62 (m, 6 H), 3.54-3.51 (m, 2 H), 3.36 (s, 3 H). LC-MS: 310.2 (MH$^+$).

Synthesis of 2-(3-methoxy-4-mPEG$_3$-phenyl)-3-methylbutyronitrile (26)

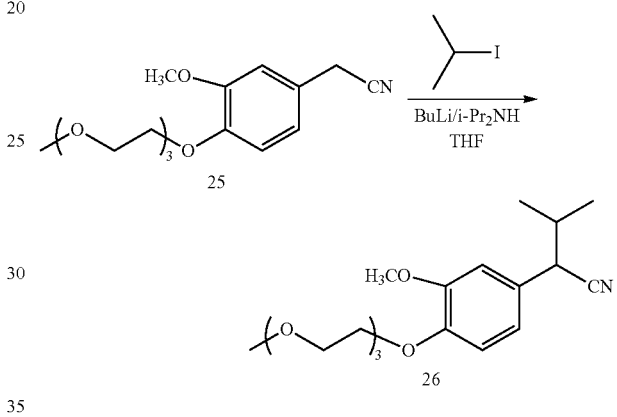

Butyllithium solution (1.6 M in hexanes, 5 mL, 8.0 mmol) was added to a stirred solution of i-Pr$_2$NH (1.13 mL, 7.99 mmol) in anhydrous THF (10 mL) at −78° C. After five minutes, 4-mPEG$_3$-3-methoxyphenylacetonitrile (25) (2.450 g, 7.92 mmol) in THF (20 mL) was added, followed by an addition of 2-iodopropane (0.8 mL, 7.92 mmol). The resulting mixture was stirred at −78° C. for five hours. The dry-acetone bath was removed. The reaction mixture was warmed up to room temperature and stirred at room temperature for 16 hours. Saturated NH$_4$Cl solution was added to quench the reaction. The solution was extracted with ethyl ether (3×20 mL). The combined organic solution was washed with brine, dried over sodium sulfate, concentrated. The residue was separated by column chromatography on silica gel using EtOAc/hexane (0-50%) to afford the product (26) (1.7656 g, 74%), along with 0.3629 g of starting material. $^1$H-NMR (CDCl$_3$): δ 6.88-6.85 (m, 1 H), 6.79-6.76 (m, 2 H), 4.15 (t, J=4.8-5.4 Hz, 2 H), 3.87-3.84 (m, 5 H), 3.73-3.70 (m, 2 H), 3.66-3.61 (m, 4 H), 3.55-3.50 (m, 3 H), 3.35 (s, 3 H), 2.12-1.77 (m, 1 H), 1.01 (d, J=6.6 Hz, 6 H). LC-MS: 352.3 (MH$^+$).

Synthesis of 3-hydroxy-2-(3-methoxy-4-mPEG$_3$-phenyl)-2-isopropyl-1-pentanenitrile (27)

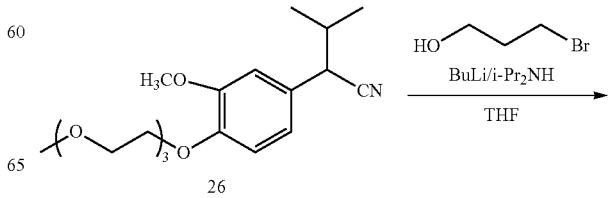

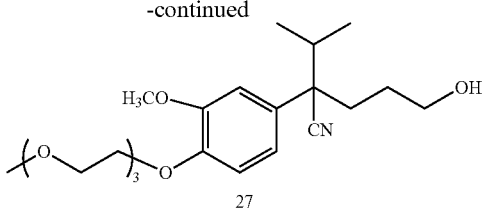

Butyllithium (1.6 M solution in hexanes, 8.0 mL, 12.80 mmol) was added to a solution of diisopropylamine (1.8 mL, 12.73 mmol) in THF (6 mL) at −78° C. Then, a solution of 2-(3-methoxy-4-mPEG$_3$-phenyl)-3-methylbutyronitrile (26) (1.76 g, 5.01 mmol) in THF (9 mL) was added. The resulting mixture was stirred for ten minutes and 3-bromo-1-propanol (0.55 mL, 6.10 mmol) was added. The resulting mixture was stirred at −78° C. for three hours and then at room temperature for three hours. Saturated NH$_4$Cl (10 mL) was added to quench the reaction. The mixture was extracted with ethyl ether (4×40 mL). The combined organic solution was washed with brine (100 mL), dried over sodium sulfate, concentrated. The residue was purified by flash column chromatography on silica gel using EtOAc/hexanes (30%, 50% and 100%) to afford 1.73 g of the product (27) in 84% yield. $^1$H-NMR (CDCl$_3$): δ 6.87-6.85 (m, 3 H), 4.17 (t, J=4.8-5.4 Hz, 2 H), 3.89-3.85 (m, 5 H), 3.74-3.71 (m, 2 H), 3.67-3.62 (m, 4 H), 3.61-3.57 (m, 2H), 3.54-3.51 (m, 2 H), 3.36 (s, 3 H), 2.24-2.14 (m, 1 H), 2.10-2.03 (m, 1 H), 1.95-1.85 (m, 1 H), 1.64-1.55 (m, 1 H), 1.26-1.16 (m, 1 H), 1.17 (d, J=6.6 Hz, 2 H), 0.78 (d, J=6.6 Hz, 6 H). LC-MS: 410.3 (MO, 432.3 (MNa$^+$).

Synthesis of 2-(3-methoxy-4-mPEG$_3$-phenyl)-2-isopropyl-5-oxo-pentanenitrile (28)

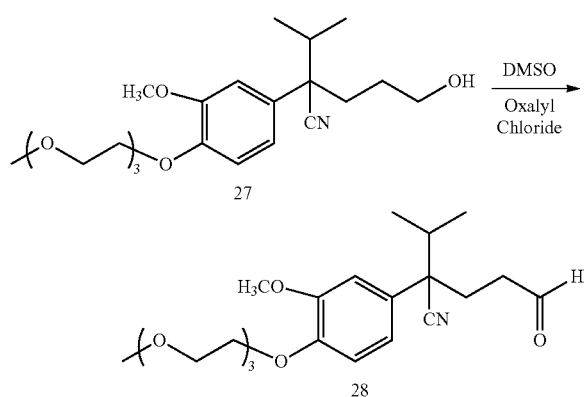

Oxalyl chloride (2.0 m solution in dichloromethane, 5.4 mL, 10.80 mmol) was added to dichloromethane (6 mL) at −78° C. Then a solution of DMSO (4.0 mL, 11.28 mmol) in DCM (4 mL) was added. After about five minutes, a solution of the alcohol (27) (1.415 g, 3.46 mmol) in DCM (10 mL) was added. After 15 minutes at −78° C., triethylamine (3.5 mL) was added. The resulting mixture was stirred for 16.5 hours. During the period, the temperature was allowed to reach room temperature. The bath was removed, and the mixture was stirred at room temperature for another hour. Saturated ammonium chloride was added to quench the reaction, extracted with ethyl ether (3×60 mL). The combined organic solution was washed with brine (2×100 mL), dried over sodium sulfate, concentrated to afford the crude product (28), which was used in the next step without further purification.

$^1$H-NMR (CDCl$_3$): δ 9.65 (s, 1 H), 6.89-6.80 (m, 3 H), 4.16 (t, J=5.1 Hz, 2 H), 3.89-3.86 (t, J=5.1 Hz, 2 H), 3.85 (s, 3 H), 3.74-3.71 (m, 2 H), 3.68-3.60 (m, 4 H), 3.55-3.52 (m, 2 H), 3.36 (s, 3 H), 2.66-2.54 (m, 1 H), 2.48-2.38 (m, 1 H), 2.21-2.03 (m, 3 H), 1.41 (m, 1 H), 1.2 (d, J=6.6 Hz, 2 H), 0.79 (d, J=6.6 Hz, 6 H). LC-MS: 408.3 (MO, 430.3 (MNa$^+$).

Synthesis of O-mPEG$_3$-verapmil (30)

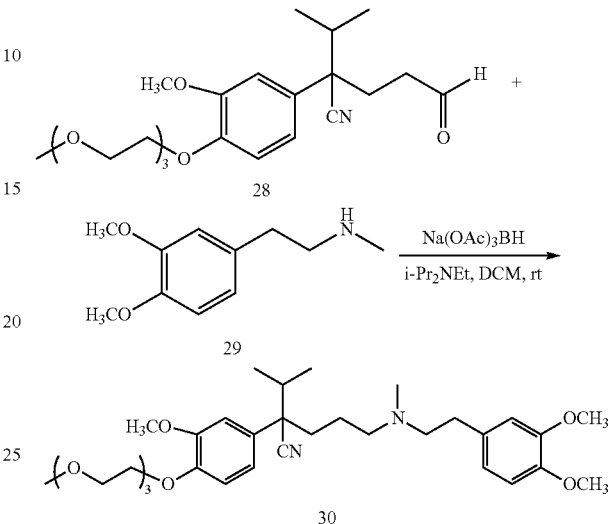

i-Pr$_2$NEt (0.02 mL, 0.11 mmol) was added to a stirred solution of 2-(3-methoxy-4-mPEG$_3$-phenyl)-2-isopropyl-5-oxo-pentanenitrile (28) (145 mg, 0.36 mmol) and N-methyl-homoveratrylamine (29) (119 mg, 0.59 mmol) in dichloromethane (6 mL). Sodium triacetoxyborohydride (182 mg, 0.82 mmol) was added. The mixture was stirred at room temperature for six hours. Water was added to quench the reaction. The organic solution was separated and the aqueous solution was extracted with dichloromethane (4×15 mL). The combined organic solution was washed with brine, dried over sodium sulfate, concentrated. The residue was purified by flash column chromatography on SiO$_2$ using EtOAC/hexanes (30-100%) and MeOH/Et$_3$N/EtOAc (2/1/20) to afford the product (30) (171 mg, 76% yield). The purity was >94% based on HPLC. The product was purified again with preparative TLC and flash column chromatography on silica gel using MeOH/DCM (0-5%) to afford 130 mg of the final product. $^1$H-NMR (CDCl$_3$): δ 6.85-6.84 (m, 3H), 6.78-6.75 (m, 1 H), 6.69-6.67 (m, 2 H), 4.10 (t, J=4.8-5.4 Hz, 2 H), 3.87-3.83 (m, 11 H), 3.74-3.71 (m, 2 H), 3.68-3.62 (m, 4 H), 3.55-3.52 (m, 2 H), 3.36 (s, 3 H), 2.67-2.62 (m, 2 H), 2.51-2.45 (m, 2 H), 2.36-2.27 (m, 2 H), 2.15 (s, 3 H), 2.12-2.00 (m, 2 H), 1.85-1.75 (m, 1 H), 1.49 (m, 1 H), 1.24 (m, 1 H), 1.16 (d, J=6.6 Hz, 3 H), 0.76 (d, J=6.6 Hz, 3H). LC-MS: 587.4 (MH$^+$).

Example 6

Synthesis of PEG-Verapamil—"Approach C"

PEG-Verapamil was prepared using a third approach. Schematically, the approach followed for this example is shown below (compound numbers in bold in the schematic correspond to the compound numbers provided in the text of this Example 5 alone).

Synthesis of PEG-Verapamil—"Approach C" Schematic

PEG-Verapamil was prepared using a third approach. Schematically, the approach followed for this example is shown below (unless otherwise stated, compound numbers in bold in the schematic correspond to the compound numbers provided in the text of this Example 6 alone).

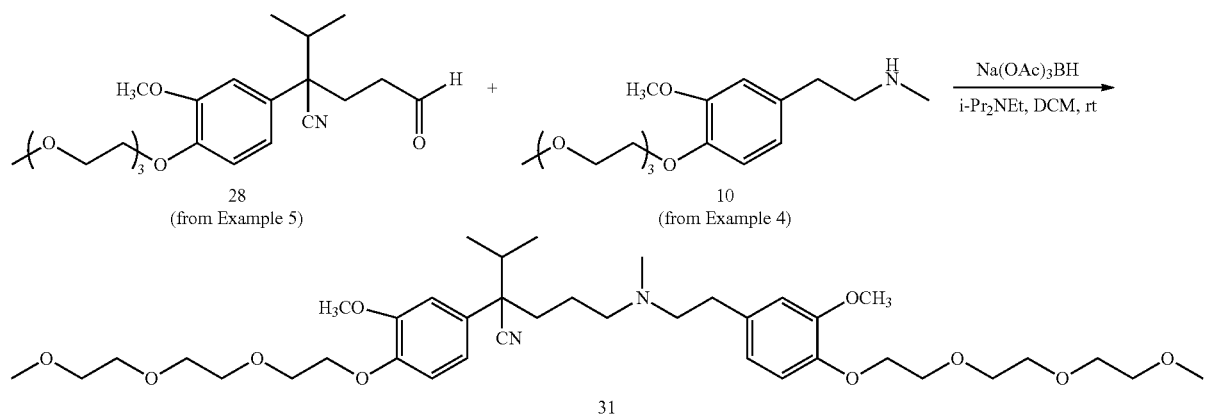

Synthesis of O,O'-di-mPEG$_3$-verapamil (31)

i-Pr$_2$NEt (0.02 mL, 0.11 mmol) was added to a stirred solution of 2-(3-methoxy-4-mPEG$_3$-phenyl)-2-isopropyl-5-oxo-pentanenitrile (28) (176 mg, 0.43 mmol) (prepared in accordance with the procedure provided in Example 5 and the mPEG$_3$ methylamine 10 (148 mg, 0.45 mmol) (prepared in accordance with the procedure provided in Example 4 in dichloromethane (6 mL). Sodium triacetoxyborohydride (225 mg, 1.01 mmol) was added. The mixture was stirred at room temperature for six hours. Water was added to quench the reaction. The organic solution was separated and the aqueous solution was extracted with dichloromethane (4×15 mL). The combined organic solution was washed with brine, dried over sodium sulfate, concentrated. The residue was purified by flash column chromatography on SiO$_2$ using EtOAC/hexanes (30-100%) and MeOH/EtOAc (0-10%) and TEA/MeOH/EtOAc (1/2/25) to afford 244 mg of the product 31 in 79% yield. $^1$H-NMR (CDCl$_3$): δ 6.85-6.79 (m, 4 H), 6.67-6.62 (m, 2 H), 4.17-4.11 (m, 4 H), 3.88-3.81 (m, 10 H), 3.74-3.70 (m, 4 H), 3.67-3.61 (m, 8 H), 3.55-3.52 (m, 4 H), 3.36 (s, 6 H), 2.66-2.61 (m, 2 H), 2.50-2.45 (m, 2 H), 2.33-2.27 (m, 2 H), 2.14 (s, 3 H), 2.05-2.00 (m, 2 H), 1.85-1.75 (m, 1 H), 1.49 (m, 1 H), 1.22 (m, 1 H), 1.15 (d, J=6.6 Hz, 3 H), 0.76 (d, J=6.6 Hz, 3 H). LC-MS: 719.5 (MH$^+$), 741.5 (MNa$^+$).

Example 7

Synthesis of PEG-Verapamil—"Approach D"

PEG-Verapamil was prepared using a fourth approach. Schematically, the approach followed for this example is shown below (compound numbers in bold in the schematic correspond to the compound numbers provided in the text of this Example 7 alone).

Synthesis of PEG-Verapamil—"Approach D" Schematic

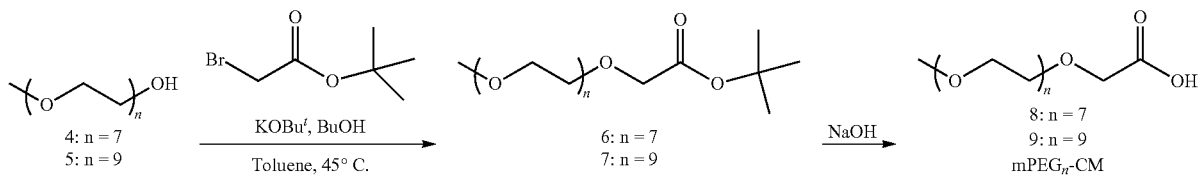

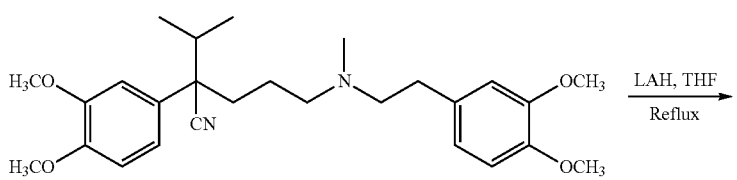

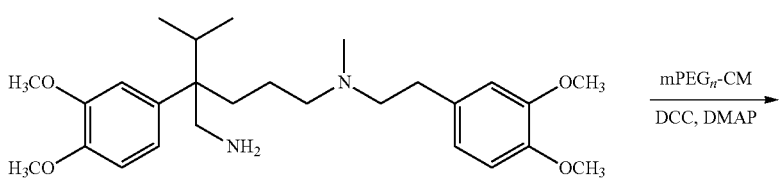

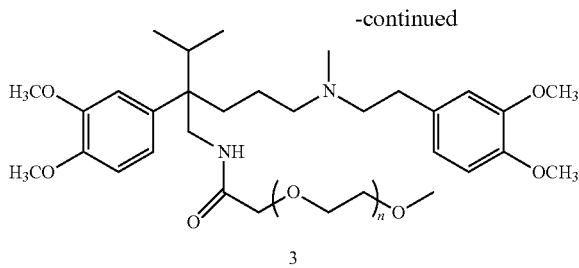

3

Synthesis of mPEG$_7$-CM (8)

mPEG$_7$-OH (4) (3.86 g, 11.34 mmol) was dissolved in toluene (125 mL), and then about 80 mL of toluene was removed under reduced pressure. t-Butanol (5 mL) was added. The mixture was heated at 45° C., then 15 mL (0.15 mmol) of 1 M potassium t-butoxide solution in 2-methyl-propanol was added. After about ten minutes at 45° C., t-butyl bromoacetate (2.5 mL, 16.58 mmol) was added. The resulting mixture was stirred at 45° C. for 22.5 hours, cooled to room temperature, and concentrated to remove the solvent. The residue was dissolved in water (50 mL), extracted with dichloromethane (3×50 mL). The combined organic solution was washed with brine (60 mL), dried over Na$_2$SO$_4$, concentrated. The residue was purified by column chromatography on silica gel using 0-10% of methanol in dichloromethane to afford 4.8852 g of mPEG$_7$ t-butyl ester (6). $^1$H-NMR (CDCl$_3$): δ 4.00 (s, 2 H), 3.74-3.52 (m, 28 H), 3.36 (s, 3 H), 1.45 (s, 9 H).

The ester was dissolved in di H$_2$O (80 mL), and 1 N NaOH was added to adjust the PH to 12. The mixture was stirred at room temperature for one day, and then 1 N HCl was added to adjust the PH to 1.8. The mixture was extracted with dichloromethane (3×50 mL). The combined organic solution was washed with brine (60 mL), dried over sodium sulfate, concentrated to afford 3.5 g of the product mPEG$_7$-CM (8). The total yield was 77%. $^1$H-NMR (CDCl$_3$): δ 4.15 (s, 2 H), 3.76-3.52 (m, 28 H), 3.36 (s, 3 H).

Synthesis of mPEG$_9$-CM (9)

mPEG$_9$-OH (5) (4.02 g, 9.38 mmol) was dissolved in toluene (250 mL), and then about 150 mL of toluene was removed under reduced pressure. t-Butanol (4 mL) was added. The mixture was heated at 45° C., and then 14 mL (0.14 mmol) of 1 M potassium t-butoxide solution in 2-methyl-propanol was added. After about ten minutes at 45° C., t-butyl bromoacetate (2.2 mL, 14.59 mmol) was added. The resulting mixture was stirred at 45° C. for 20 hours, cooled to room temperature, and concentrated to remove the solvent. The residue was dissolved in water (50 mL), extracted with dichloromethane (3×40 mL). The combined organic solution was washed with brine (60 mL), dried over Na$_2$SO$_4$, concentrated. The residue was purified twice by column chromatography on silica gel using 0-10% of methanol in dichloromethane to afford 1.843 g of mPEG$_9$ t-butyl ester (7) in 36% yield. $^1$H-NMR (CDCl$_3$): δ 3.99 (s, 2 H), 3.70-3.51 (m, 36 H), 3.35 (s, 3 H), 1.45 (s, 9 H).

The ester was dissolved in di H$_2$O (60 mL), and 1 N NaOH was added to adjust the PH to 12. The mixture was stirred at room temperature for 19 hours, and then 1 N HCl was added to adjust the PH to 1.3. The mixture was extracted with dichloromethane (3×30 mL). The combined organic solution was washed with brine (50 mL), dried over sodium sulfate, concentrated to afford 1.455 g of the product mPEG$_7$-CM (9) in 88% yield. $^1$H-NMR (CDCl$_3$): δ 4.15 (s, 2 H), 3.76-3.52 (m, 36 H), 3.36 (s, 3 H).

Synthesis of verapamil-NH$_2$ (2)

Lithium aluminum hydride (1.0 M THF solution) (55 mL, 55 mmol) was added dropwise to a stirred suspension of (±)-verapamil (1) hydrochloride (5.91 g, 11.91 mmol) in dry THF (400 mL) at room temperature. After the addition, the mixture was heated to reflux for 42.5 hours. The mixture was cooled to 0° C., Na$_2$SO$_4$.10H$_2$O was added slowly to quench the reaction. The mixture was stirred at room temperature for one day, filtered to remove the solid and the solid was washed with DCM and ethyl acetate. The combined organic solutions were concentrated. The resulting residue was dissolved in DCM (200 mL), washed with 5% aqueous NaHCO$_3$ (100 mL), water (50 mL) and brine (100 mL), dried over sodium sulfate, concentrated. The residue was dried under high vacuum to afford 5.633 g of crude product (2), which was analyzed by $^1$H-NMR and HPLC. The majority (66%) is the product based on the HPLC analysis of the crude product.

Synthesis of mPEG$_3$-NH-verapamil [(3), n=3]

Verapamil-NH$_2$ (2) (136 mg, 0.296 mmol), mPEG$_3$-OCH$_2$COOH (66 mg, 0.297 mmol) and DMAP (28 mg, 0.229 mmol) were dissolved in DCM (5 mL) at room temperature. Then, 1 M DCM solution of DCC (0.6 mL, 0.6 mmol) was added. The reaction mixture was stirred at room temperature for 18 hours. The mixture was filtered and washed with DCM. The organic solution was concentrated. The residue was separated by preparative TLC using 10% MeOH in DCM to afford 73.9 mg of the desired mPEG$_3$-NH-verapamil [(3), n=3]. $^1$H-NMR (CDCl$_3$): δ 6.76-6.66 (m, 6 H), 6.56 (br, 1 H), 3.88 (s, 2 H), 3.82-3.80 (m, 12H), 3.57-3.46 (m, 12 H), 3.33 (s, 3 H), 2.70-2.65 (m, 2 H), 2.56-2.51 (m, 2 H), 2.40-2.35 (t, J=6.9-7.2 Hz, 3 H), 2.22 (s, 3 H), 1.95-1.78 (m, 1 H), 1.71 (t, J=7.8-8.1 Hz, 2 H) 1.43-1.30 (m, 2 H), 0.77 (t, 6 H). MS 663.4 (MH$^+$).

Synthesis of mPEG$_7$-NH-verapamil [(3), n=7]

Verapamil-NH$_2$ (2) (280 mg, 0.611 mmol), mPEG$_7$-OCH$_2$COOH (302 mg, 0.758 mmol) and DMAP (105 mg, 0.859 mmol) were dissolved in DCM (8 mL) at room temperature. Then, 1 M DCM solution of DCC (1.25 mL, 1.25 mmol) was added and the reaction mixture was stirred at room temperature for 24 hours. The mixture was filtered and washed with DCM. The organic solution was concentrated. The residue was separated by preparative TLC and column chromatography on silica gel using 0-10% MeOH in DCM to afford 225.7 mg of the desired mPEG$_7$-NH-verapamil [(3), n=7] in 44% yield. $^1$H-NMR (CDCl$_3$): δ 6.81-6.67 (m, 6 H), 6.56 (br, 1 H), 3.89 (s, 2 H), 3.83-3.81 (m, 12 H), 3.62-3.46 (m, 28 H), 3.34 (s, 3 H), 2.70-2.65 (m, 2 H), 2.56-2.51 (m, 2 H), 2.39-2.35 (m, 2 H), 2.23 (s, 3 H), 1.93-1.84 (m, 1 H), 1.72 (t, J=7.5 Hz, 2 H) 1.38 (m, 2 H), 0.78 (t, J=6.6 Hz, 6 H). MS 839.5 (MH$^+$), 861.5 (MNa$^+$).

Synthesis of mPEG$_9$-NH-verapamil [(3), n=9]

Verapamil-NH$_2$ (2) (280 mg, 0.611 mmol), mPEG$_9$-OCH$_2$COOH (466 mg, 0.958 mmol) and DMAP (107 mg, 0.876 mmol) were dissolved in DCM (8 mL) at room temperature. Then, 1 M DCM solution of DCC (1.3 mL, 1.3 mmol) was added and the reaction mixture was stirred at room temperature for 66 h. The mixture was filtered and washed with DCM. The organic solution was concentrated. The residue was separated by column chromatography on silica gel using 10% MeOH in DCM, and purified again with preparative TLC with 10% MeOH/CH$_2$Cl$_2$ to afford the mPEG$_9$-NH-VERAPAMIL product. The product was dissolved in DCM (50 mL), washed with 5% aq. sodium bicarbonate (40 mL), brine (50 mL), dried over anhydrous sodium sulfate, concentrated to afford 319 mg of mPEG$_9$-NH-verapamil [(3), n=9] in 56% yield. $^1$H-NMR (CDCl$_3$): δ 6.82-6.69 (m, 6 H), 6.58 (br, 1 H), 3.90 (s, 2 H), 3.85-3.83 (m, 12 H), 3.63-3.48 (m, 36 H), 3.36 (s, 3 H), 2.69 (m, 2H), 2.57 (m, 2 H), 2.39 (m, 2 H), 2.26 (s, 3 H), 1.93-1.86 (m, 1 H), 1.73 (t, J=6.9-7.8 Hz, 2H) 1.40 (m, 2 H), 0.80 (t, J=6.6 Hz, 6 H). MS 928.3 (MO.

Example 8

Calcium Channel Binding Assay

A binding assay was performed similar to that set forth in Example 3, except that $^3$[H]-diltiazem is used as the competing radioligand. The results are shown below (mPEG$_6$-O-Verapamil was run separately wherein the diltiazem control had an IC$_{50}$=3.21×10-7).

TABLE 1

Results from Binding Assay Experiment 1

| Drug | IC$_{50}$ (M) |
|---|---|
| Diltiazem | 3.45 × 10−8 |
| Verapamil | 2.98 × 10−8 |
| Verapamil-amine [compound (2) from Example 7] | 1.37 × 10−6 |
| mPEG$_3$-NH-Verapamil [compound (3) from Example 7] | 2.99 × 10−6 |

TABLE 2

Results from Binding Assay No. 2

| Drug | IC$_{50}$ (M) |
|---|---|
| Diltiazem | 2.89 × 10−8 |
| Verapamil | 2.98 × 10−8 |
| mPEG$_3$-O-Verapamil [compound (20) from Example 4] | 5.41 × 10−7 |
| mPEG$_5$-O-Verapamil [compound (21) from Example 4] | 8.52 × 10−7 |
| mPEG$_6$-O-Verapamil [compound (22) from Example 4] | 3.49 × 10−7* |
| mPEG$_7$-O-Verapamil [compound (23) from Example 4] | 1.13 × 10−6 |

Example 9

Synthesis of PEG-Amlodipine—"stable PEG linkage"

PEG-Amlodopine was prepared in accordance with the schematic provided below (wherein the linkage between the PEG and the amlodipine is substantially stable, i.e., substantially non-hydrolyzable), using methods, reagents and intermediates known to those of ordinary skill in the art. In the schematic, n=3, 5, 7, and so on.

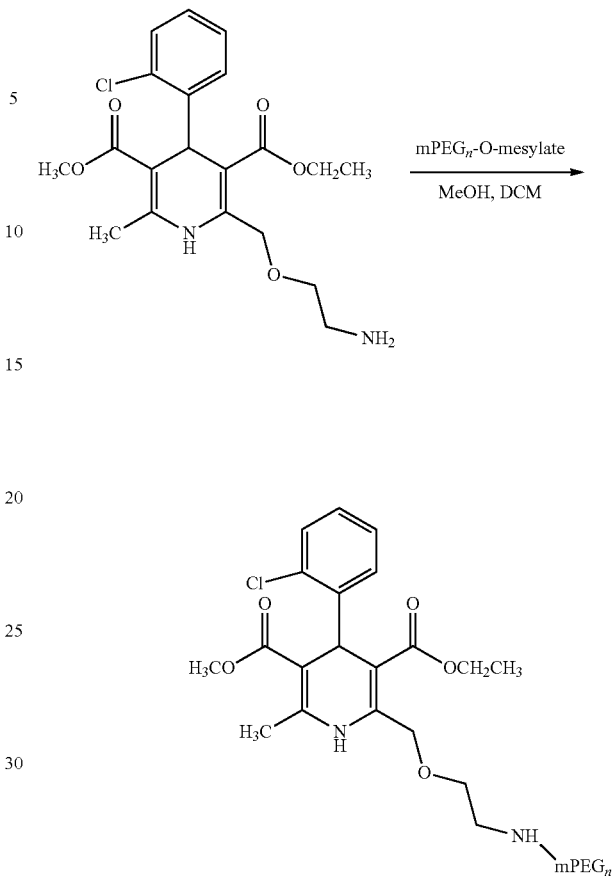

Example 10

Synthesis of PEC-Amlodipine—"hydrolyzable PEG linkage"

PEG-Amlodopine was prepared in accordance with the schematic provided below (wherein the linkage between the PEG and the amlodipine is substantially stable), using methods, reagents and intermediates known to those of ordinary skill in the art. In the schematic, n=3, 5, 7, and so on.

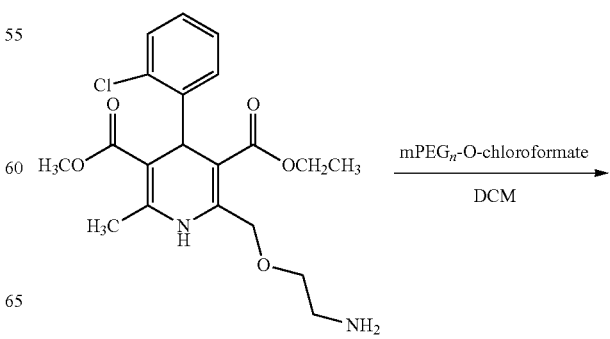

-continued

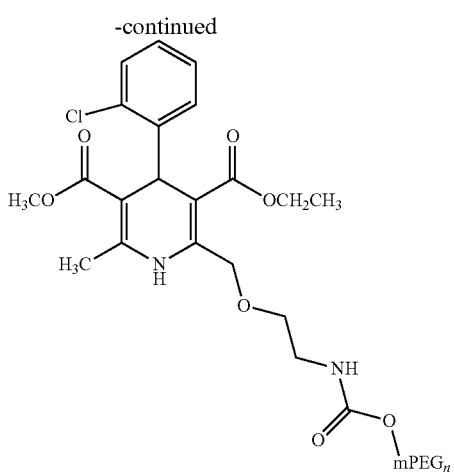

What is claimed is:

1. A compound having the structure:

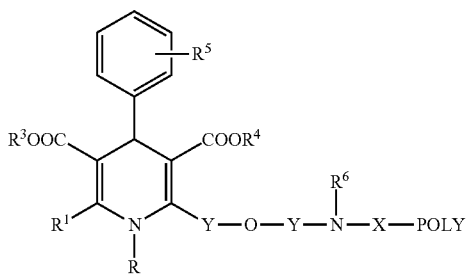

wherein:
R is hydrogen or lower alkyl;
R$^1$ is selected from the group consisting of hydrogen, substituted lower alkyl, unsubstituted lower alkyl and —YOYNR$^6$R$^7$, where each Y is independently lower alkylene and R$^6$ and R$^7$ are each independently selected from group consisting of hydrogen, unsubstituted lower alkyl, substituted lower alkyl, cycloalkyl, aryl and alkylaryl;
each Y is independently lower alkylene;
R$^3$ and R$^4$ are independently selected from the group consisting of hydrogen, unsubstituted lower alkyl, substituted lower alkyl, and —YNR$^6$R$^7$, where Y is lower alkylene and R$^6$ and R$^7$ are each independently selected from group consisting of hydrogen, unsubstituted lower alkyl, substituted lower alkyl, cycloalkyl, aryl and alkylaryl;
R$^5$ is independently selected from group consisting of hydrogen, unsubstituted lower alkyl, substituted lower alkyl, chloro, fluoro and nitro;
R$^6$ is selected from group consisting of hydrogen, unsubstituted lower alkyl, substituted lower alkyl, cycloalkyl, aryl and alkylaryl;
X is a spacer moiety; and
POLY is a water-soluble oligomer wherein the number of monomers has a number between 2 and 30.

2. The compound of claim 1, wherein the water-soluble, non-peptidic oligomer is a poly(alkylene oxide).

3. The compound of claim 2, wherein the poly(alkylene oxide) is a poly(ethylene oxide).

4. The compound of claim 2, wherein the poly(alkylene oxide) includes an alkoxy or hydroxy end-capping moiety.

5. The compound of claim 1, having the structure:

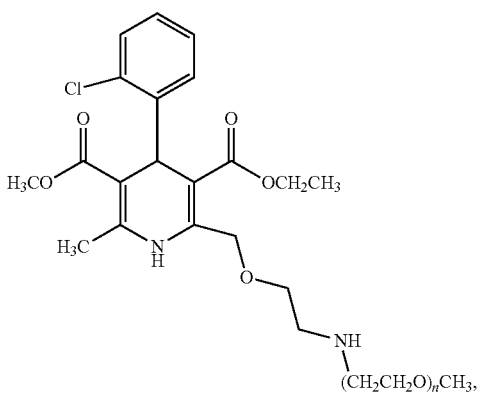

wherein n is an integer of from 2 to 10.

6. The compound of claim 1, having the structure:

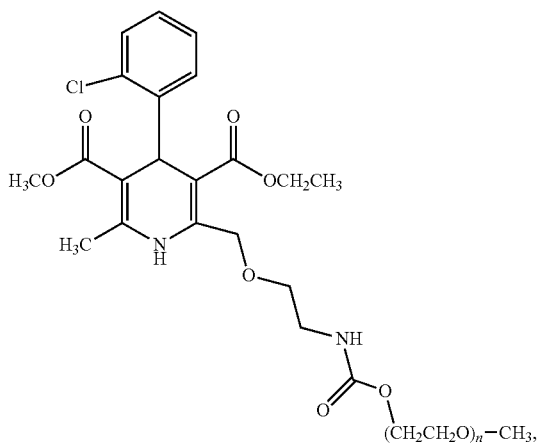

wherein n is an integer of from 2 to 10.

* * * * *